(12) United States Patent
Bianchi et al.

(10) Patent No.: US 11,918,445 B2
(45) Date of Patent: *Mar. 5, 2024

(54) ABSORBENT ARTICLE WITH IMPROVED CORE-TO-BACKSHEET ADHESIVE

(71) Applicant: The Procter & Gamble Company, Cincinnati, OH (US)

(72) Inventors: Ernesto Gabriel Bianchi, Oberursel (DE); José Mauricio Berrizbeitia, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 470 days.

This patent is subject to a terminal disclaimer.

(21) Appl. No.: 16/921,974

(22) Filed: Jul. 7, 2020

(65) Prior Publication Data
US 2020/0337915 A1    Oct. 29, 2020

Related U.S. Application Data

(63) Continuation of application No. 15/152,583, filed on May 12, 2016, now Pat. No. 10,736,795.
(Continued)

(51) Int. Cl.
*A61F 13/15* (2006.01)
*A61F 13/514* (2006.01)
(Continued)

(52) U.S. Cl.
CPC ...... *A61F 13/539* (2013.01); *A61F 13/15577* (2013.01); *A61F 13/514* (2013.01);
(Continued)

(58) Field of Classification Search
CPC .............. A61F 13/539; A61F 13/15577; A61F 13/514; A61F 2013/51409; A61F 2013/530481; A61F 2013/53908
See application file for complete search history.

(56) References Cited

U.S. PATENT DOCUMENTS

| | | |
|---|---|---|
| 1,733,997 A | 10/1929 | Marr |
| 1,734,499 A | 11/1929 | Marinsky |

(Continued)

FOREIGN PATENT DOCUMENTS

| | | |
|---|---|---|
| CA | 2001370 | 4/1990 |
| CA | 2291997 | 6/2000 |

(Continued)

OTHER PUBLICATIONS

All Office Actions; U.S. Appl. No. 15/152,583.
International Search Report and Written Opinion; Application Ser. No. PCT/US2016/032062; dated Jul. 21, 2016, 11 pages.

*Primary Examiner* — Jacqueline F Stephens
(74) *Attorney, Agent, or Firm* — Daniel S. Albrecht; Wednesday G. Shipp; Sarah M. DeCristofaro

(57) ABSTRACT

An absorbent article for personal hygiene comprising: a topsheet, a backsheet, an absorbent core, the backsheet comprising a plastic film having a longitudinal tear strength measured in N/cm; the absorbent core being partially attached to the plastic film of the backsheet by a first glue wherein at least a continuous area of 10 mm in longitudinal direction and 25 mm in transversal direction of the bottom side of the core is unattached to the backsheet by the first glue or by any other means of attachment. In the first glue application area, the absorbent article has a core-to-backsheet peel strength measured in N/cm, such that the core-to-backsheet peel strength ranges from 10% to 40% of the longitudinal tear strength of the plastic film.

13 Claims, 12 Drawing Sheets

Related U.S. Application Data

(60) Provisional application No. 62/160,226, filed on May 12, 2015.

(51) Int. Cl.
  *A61F 13/53* (2006.01)
  *A61F 13/539* (2006.01)

(52) U.S. Cl.
  CPC .... *A61F 13/53* (2013.01); *A61F 2013/51409* (2013.01); *A61F 2013/530481* (2013.01); *A61F 2013/53908* (2013.01)

(56) References Cited

U.S. PATENT DOCUMENTS

| | | |
|---|---|---|
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,003 A | 4/1957 | Morin |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,071,138 A | 1/1963 | Gustavo |
| 3,180,335 A | 4/1965 | Duncan et al. |
| 3,207,158 A | 9/1965 | Yoshitake et al. |
| 3,227,160 A | 1/1966 | Joy |
| 3,386,442 A | 6/1968 | Sabee |
| 3,561,446 A | 2/1971 | Jones |
| 3,572,342 A | 3/1971 | Lindquist et al. |
| 3,572,432 A | 3/1971 | Burton |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 10/1974 | Sabee |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,079,739 A | 3/1978 | Whitehead |
| 4,084,592 A | 4/1978 | Tritsch |
| 4,100,922 A | 7/1978 | Hernandez |
| 4,232,674 A | 11/1980 | Melican |
| 4,257,418 A | 3/1981 | Hessner |
| 4,259,220 A | 3/1981 | Bunnelle et al. |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,360,021 A | 11/1982 | Stima |
| 4,381,783 A | 5/1983 | Elias |
| 4,388,075 A | 6/1983 | Mesek et al. |
| 4,410,571 A | 10/1983 | Korpman |
| 4,461,621 A | 7/1984 | Karami et al. |
| 4,463,045 A | 7/1984 | Ahr et al. |
| 4,469,710 A | 9/1984 | Rielley et al. |
| 4,475,912 A | 10/1984 | Coates |
| 4,490,148 A | 12/1984 | Beckeström |
| 4,507,438 A | 3/1985 | Obayashi et al. |
| 4,515,595 A | 5/1985 | Kievet et al. |
| 4,527,990 A | 7/1985 | Sigl |
| 4,541,871 A | 9/1985 | Obayashi et al. |
| 4,551,191 A | 11/1985 | Kock et al. |
| 4,573,986 A | 3/1986 | Minetola et al. |
| 4,578,072 A | 3/1986 | Lancaster |
| 4,578,702 A | 3/1986 | Campbell |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman et al. |
| 4,623,342 A | 11/1986 | Ito et al. |
| 4,624,666 A | 11/1986 | Derossett |
| 4,629,643 A | 12/1986 | Curro et al. |
| 4,636,207 A | 1/1987 | Buell |
| 4,641,381 A | 2/1987 | Heran et al. |
| 4,646,510 A | 3/1987 | McIntyre |
| 4,662,875 A | 5/1987 | Hirotsu et al. |
| 4,666,983 A | 5/1987 | Tsubakimoto et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,710,189 A | 12/1987 | Lash |
| 4,720,321 A | 1/1988 | Smith |
| 4,731,066 A | 3/1988 | Korpman |
| 4,731,070 A | 3/1988 | Koci |
| RE32,649 E | 4/1988 | Brandt et al. |
| 4,741,941 A | 5/1988 | Englebert et al. |
| 4,747,846 A | 5/1988 | Boland et al. |
| 4,753,648 A | 6/1988 | Jackson |
| 4,773,905 A | 9/1988 | Molee |
| 4,784,892 A | 11/1988 | Storey et al. |

(56) References Cited

U.S. PATENT DOCUMENTS

| | | |
|---|---|---|
| 4,785,996 A | 11/1988 | Ziecker et al. |
| 4,787,896 A | 11/1988 | Houghton et al. |
| 4,795,454 A | 1/1989 | Dragoo |
| 4,800,102 A | 1/1989 | Takada |
| 4,802,884 A | 2/1989 | Fröidh et al. |
| 4,806,408 A | 2/1989 | Pierre et al. |
| 4,806,598 A | 2/1989 | Morman |
| 4,808,176 A | 2/1989 | Kielpikowski |
| 4,808,178 A | 2/1989 | Aziz |
| 4,826,880 A | 5/1989 | Lesniak et al. |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,848,815 A | 7/1989 | Molloy |
| 4,861,652 A | 8/1989 | Lippert et al. |
| 4,869,724 A | 9/1989 | Scripps |
| 4,886,697 A | 12/1989 | Perdelwitz, Jr. et al. |
| 4,888,231 A | 12/1989 | Angstadt |
| 4,892,528 A | 1/1990 | Suzuki et al. |
| 4,892,535 A | 1/1990 | Bjornberg |
| 4,892,536 A | 1/1990 | DesMarais et al. |
| 4,894,060 A | 1/1990 | Nestegard |
| 4,894,277 A | 1/1990 | Akasaki |
| 4,904,251 A | 2/1990 | Igaue et al. |
| 4,900,317 A | 3/1990 | Buell |
| 4,909,802 A | 3/1990 | Ahr et al. |
| 4,909,803 A | 3/1990 | Aziz et al. |
| 4,936,839 A | 6/1990 | Molee |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson et al. |
| 4,966,809 A | 10/1990 | Tanaka et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen et al. |
| 5,071,414 A | 8/1991 | Elliott |
| 5,072,687 A | 12/1991 | Mitchell |
| 5,085,654 A | 2/1992 | Buell |
| 5,087,255 A | 2/1992 | Sims et al. |
| 5,092,861 A | 3/1992 | Nomura et al. |
| 5,102,597 A | 4/1992 | Roe et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger |
| 5,147,345 A | 9/1992 | Young et al. |
| 5,149,334 A | 9/1992 | Roe et al. |
| 5,149,335 A | 9/1992 | Kellenberger et al. |
| 5,151,091 A | 9/1992 | Glaug |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,175,046 A | 12/1992 | Nguyen |
| 5,180,622 A | 1/1993 | Berg et al. |
| 5,190,563 A | 3/1993 | Herron et al. |
| 5,190,606 A | 3/1993 | Merkatoris et al. |
| 5,204,997 A | 4/1993 | Suzuki et al. |
| 5,213,817 A | 5/1993 | Pelley |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola et al. |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | Desmarais et al. |
| 5,269,775 A | 12/1993 | Freeland et al. |
| 5,281,683 A | 1/1994 | Yano et al. |
| H1298 H | 4/1994 | Ahr |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | LaVon et al. |
| 5,366,782 A | 11/1994 | Curro et al. |
| 5,382,610 A | 1/1995 | Harada et al. |
| 5,387,207 A | 2/1995 | Dyer et al. |
| 5,387,208 A | 2/1995 | Ashton et al. |
| 5,387,209 A | 2/1995 | Yamamoto et al. |
| 5,389,095 A | 2/1995 | Suzuki |
| 5,397,316 A | 3/1995 | Lavon et al. |
| 5,397,317 A | 3/1995 | Thomas |
| 5,399,175 A | 3/1995 | Glaug |
| 5,401,792 A | 3/1995 | Babu et al. |
| 5,409,771 A | 4/1995 | Dahmen et al. |
| H1440 H | 5/1995 | New et al. |
| 5,411,497 A | 5/1995 | Tanzer et al. |
| 5,415,644 A | 5/1995 | Enloe |
| 5,425,725 A | 6/1995 | Tanzer et al. |
| 5,429,630 A | 7/1995 | Beal et al. |
| 5,433,715 A | 7/1995 | Tanzer et al. |
| 5,451,219 A | 9/1995 | Suzuki |
| 5,451,442 A | 9/1995 | Pieniak |
| 5,460,622 A | 10/1995 | Dragoo et al. |
| 5,460,623 A | 10/1995 | Emenaker et al. |
| 5,462,541 A | 10/1995 | Bruemmer et al. |
| 5,476,458 A | 12/1995 | Glaug et al. |
| 5,486,166 A | 1/1996 | Bishop et al. |
| 5,486,167 A | 1/1996 | Dragoo et al. |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell et al. |
| 5,507,736 A | 4/1996 | Clear et al. |
| 5,507,895 A | 4/1996 | Suekane |
| 5,509,915 A | 4/1996 | Hanson et al. |
| 5,514,104 A | 5/1996 | Cole |
| 5,518,801 A | 5/1996 | Chappell et al. |
| 5,520,674 A | 5/1996 | Hines et al. |
| 5,522,810 A | 6/1996 | Allen, Jr. |
| 5,527,300 A | 6/1996 | Sauer |
| 5,531,730 A | 7/1996 | Dreier |
| 5,532,323 A | 7/1996 | Yano et al. |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe et al. |
| 5,559,335 A | 9/1996 | Zing et al. |
| 5,560,878 A | 10/1996 | Dragoo et al. |
| 5,562,634 A | 10/1996 | Flumene et al. |
| 5,562,646 A | 10/1996 | Goldman et al. |
| 5,569,234 A | 10/1996 | Buell et al. |
| 5,571,096 A | 11/1996 | Dobrin et al. |
| 5,574,121 A | 11/1996 | Irie et al. |
| 5,575,783 A | 11/1996 | Clear et al. |
| 5,580,411 A | 12/1996 | Nease et al. |
| 5,584,829 A | 12/1996 | Lavash et al. |
| 5,586,979 A | 12/1996 | Thomas |
| 5,591,152 A | 1/1997 | Buell et al. |
| 5,591,155 A | 1/1997 | Nishikawa et al. |
| 5,593,399 A | 1/1997 | Tanzer et al. |
| 5,599,335 A | 2/1997 | Goldman et al. |
| 5,601,542 A | 2/1997 | Melius et al. |

(56) References Cited

U.S. PATENT DOCUMENTS

| | | |
|---|---|---|
| 5,607,414 A | 3/1997 | Richards et al. |
| 5,607,537 A | 3/1997 | Johnson et al. |
| 5,607,760 A | 3/1997 | Roe |
| 5,609,587 A | 3/1997 | Roe |
| 5,609,588 A | 3/1997 | DiPalma et al. |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur |
| 5,624,424 A | 4/1997 | Saisaka et al. |
| 5,625,222 A | 4/1997 | Yoneda et al. |
| 5,607,416 A | 5/1997 | Yamamoto et al. |
| 5,626,571 A | 5/1997 | Young et al. |
| 5,628,741 A | 5/1997 | Buell et al. |
| 5,628,845 A | 5/1997 | Murray et al. |
| 5,635,191 A | 6/1997 | Roe et al. |
| 5,635,271 A | 6/1997 | Zafiroglu |
| 5,637,106 A | 6/1997 | Mitchell |
| 5,643,238 A | 7/1997 | Baker |
| 5,643,243 A | 7/1997 | Klemp |
| 5,643,588 A | 7/1997 | Roe et al. |
| 5,649,914 A | 7/1997 | Glaug |
| 5,650,214 A | 7/1997 | Anderson |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,662,758 A | 9/1997 | Hamilton et al. |
| 5,669,894 A | 9/1997 | Goldman et al. |
| 5,674,215 A | 10/1997 | Ronnberg |
| 5,681,300 A | 10/1997 | Ahr |
| 5,683,374 A | 11/1997 | Yamamoto |
| 5,685,874 A | 11/1997 | Buell et al. |
| 5,690,624 A | 11/1997 | Sasaki et al. |
| 5,690,627 A | 11/1997 | Clear et al. |
| 5,691,035 A | 11/1997 | Chappell et al. |
| 5,691,036 A | 11/1997 | Chappell et al. |
| 5,695,488 A | 12/1997 | Sosalla |
| 5,700,254 A | 12/1997 | McDowall et al. |
| 5,702,376 A | 12/1997 | Glaug |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | Mcfall et al. |
| H1732 H | 6/1998 | Johnson |
| 5,762,641 A | 6/1998 | Bewick et al. |
| 5,766,388 A | 6/1998 | Pelley |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura et al. |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka |
| 5,830,202 A | 11/1998 | Bogdanski et al. |
| 5,833,678 A | 11/1998 | Ashton et al. |
| 5,837,789 A | 11/1998 | Stockhausen et al. |
| 5,840,404 A | 11/1998 | Graff |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mitzutani |
| 5,855,572 A | 1/1999 | Schmidt |
| 5,858,013 A | 1/1999 | Kling |
| 5,858,515 A | 1/1999 | Stokes et al. |
| 5,865,823 A | 2/1999 | Curro |
| 5,865,824 A | 2/1999 | Chen |
| 5,873,868 A | 2/1999 | Nakahata |
| 5,876,391 A | 3/1999 | Roe et al. |
| 5,879,751 A | 3/1999 | Bogdanski |
| 5,891,118 A | 4/1999 | Toyoshima |
| 5,891,544 A | 4/1999 | Chappell et al. |
| 5,897,545 A | 4/1999 | Kline et al. |
| 5,904,673 A | 5/1999 | Roe et al. |
| 5,925,439 A | 7/1999 | Haubach |
| 5,928,184 A | 7/1999 | Etheredge |
| 5,931,825 A | 8/1999 | Kuen et al. |
| 5,938,648 A | 8/1999 | Lavon et al. |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,957,908 A | 9/1999 | Kline et al. |
| 5,968,025 A | 10/1999 | Roe et al. |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka |
| 6,054,631 A | 4/2000 | Gent |
| 6,056,732 A | 5/2000 | Fujioka et al. |
| 6,060,115 A | 5/2000 | Borowski et al. |
| 6,068,620 A | 5/2000 | Chmielewski |
| 6,080,909 A | 6/2000 | Osterdahl et al. |
| 6,083,210 A | 7/2000 | Young et al. |
| 6,090,994 A | 7/2000 | Chen |
| 6,091,336 A | 7/2000 | Zand |
| 6,093,474 A | 7/2000 | Sironi |
| 6,099,515 A | 8/2000 | Sugito |
| 6,102,892 A | 8/2000 | Putzer et al. |
| 6,103,814 A | 8/2000 | Van Drongelen et al. |
| 6,107,537 A | 8/2000 | Elder et al. |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak |
| 6,143,821 A | 11/2000 | Houben |
| 6,152,908 A | 11/2000 | Widlund |
| 6,156,023 A | 12/2000 | Yoshioka |
| 6,156,424 A | 12/2000 | Taylor |
| 6,160,197 A | 12/2000 | Lassen |
| 6,165,160 A | 12/2000 | Suzuki et al. |
| 6,174,302 B1 | 1/2001 | Kumasaka |
| 6,177,606 B1 | 1/2001 | Etheredge |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Rönnberg |
| 6,254,294 B1 | 7/2001 | Muhar |
| 6,258,996 B1 | 7/2001 | Goldman |
| 6,265,488 B1 | 7/2001 | Fujino et al. |
| 6,290,686 B1 | 9/2001 | Tanzer et al. |
| 6,302,872 B1 | 10/2001 | Teranishi |
| 6,306,122 B1 | 10/2001 | Narawa et al. |
| 6,315,765 B1 | 11/2001 | Datta |

(56) References Cited

U.S. PATENT DOCUMENTS

| | | |
|---|---|---|
| 6,319,239 B1 | 11/2001 | Daniels et al. |
| 6,322,552 B1 | 11/2001 | Blenke et al. |
| 6,325,787 B1 | 12/2001 | Roe et al. |
| 6,326,525 B1 | 12/2001 | Hamajima |
| 6,330,735 B1 | 12/2001 | Hahn et al. |
| 6,334,858 B1 | 1/2002 | Rönnberg et al. |
| 6,336,922 B1 | 1/2002 | Van Gompel et al. |
| 6,340,611 B1 | 1/2002 | Shimizu |
| 6,342,715 B1 | 1/2002 | Shimizu |
| 6,402,731 B1 | 1/2002 | Suprise et al. |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin et al. |
| 6,383,960 B1 | 5/2002 | Everett et al. |
| 6,394,989 B2 | 5/2002 | Mizutani |
| 6,403,857 B1 | 6/2002 | Gross et al. |
| 6,406,467 B1 | 6/2002 | Dilnik et al. |
| 6,409,883 B1 | 6/2002 | Makolin |
| 6,410,820 B1 | 6/2002 | McFall et al. |
| 6,410,822 B1 | 6/2002 | Mizutani |
| 6,402,729 B1 | 7/2002 | Boberg et al. |
| 6,413,248 B1 | 7/2002 | Mizutani |
| 6,413,249 B1 | 7/2002 | Turi et al. |
| 6,414,214 B1 | 7/2002 | Engelhardt et al. |
| 6,416,502 B1 | 7/2002 | Connelly et al. |
| 6,416,697 B1 | 7/2002 | Venturino et al. |
| 6,419,667 B1 | 7/2002 | Avalon et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline et al. |
| 6,432,099 B2 | 8/2002 | Rönnberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry et al. |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,034 B1 | 10/2002 | Schaefer et al. |
| 6,461,342 B2 | 10/2002 | Tanji et al. |
| 6,461,343 B1 | 10/2002 | Schaefer et al. |
| 6,472,478 B1 | 10/2002 | Funk et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler |
| 6,506,961 B1 | 1/2003 | Levy |
| 6,515,195 B1 | 2/2003 | Lariviere |
| 6,517,525 B1 | 2/2003 | Berthou |
| 6,518,479 B1 | 2/2003 | Graef |
| 6,520,947 B1 | 2/2003 | Tilly et al. |
| 6,521,811 B1 | 2/2003 | Lassen |
| 6,521,812 B1 | 2/2003 | Graef |
| 6,524,294 B1 | 2/2003 | Hilston et al. |
| 6,525,240 B1 | 2/2003 | Graef |
| 6,528,698 B2 | 3/2003 | Mizutani et al. |
| 6,529,860 B1 | 3/2003 | Strumolo et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld |
| 6,585,713 B1 | 7/2003 | LaMahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,630,054 B1 | 10/2003 | Graef |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya |
| 6,667,424 B1 | 12/2003 | Hamilton |
| 6,670,522 B1 | 12/2003 | Graef |
| 6,673,982 B1 | 1/2004 | Chen |
| 6,673,983 B1 | 1/2004 | Graef |
| 6,673,985 B2 | 1/2004 | Mizutani |
| 6,682,515 B1 | 1/2004 | Mizutani et al. |
| 6,682,516 B2 | 1/2004 | Johnston |
| 6,689,115 B1 | 2/2004 | Popp et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen |
| 6,705,465 B2 | 3/2004 | Ling et al. |
| 6,706,129 B2 | 3/2004 | Ando et al. |
| 6,706,943 B2 | 3/2004 | Onishi |
| 6,710,224 B2 | 3/2004 | Chmielewski et al. |
| 6,710,225 B1 | 3/2004 | Everett et al. |
| 6,716,205 B2 | 4/2004 | Popp et al. |
| 6,716,441 B1 | 4/2004 | Roe et al. |
| 6,717,029 B2 | 4/2004 | Baker |
| 6,726,668 B2 | 4/2004 | Underhill et al. |
| 6,726,792 B1 | 4/2004 | Johnson et al. |
| 6,730,387 B2 | 5/2004 | Rezai et al. |
| 6,734,335 B1 | 5/2004 | Graef |
| 6,790,798 B1 | 9/2004 | Suzuki et al. |
| 6,802,834 B2 | 10/2004 | Melius et al. |
| 6,809,158 B2 | 10/2004 | Ikeuchi et al. |
| 6,811,642 B2 | 11/2004 | Ochi |
| 6,818,083 B2 | 11/2004 | Mcamish et al. |
| 6,818,166 B2 | 11/2004 | Edwardson et al. |
| 6,830,800 B2 | 12/2004 | Curro et al. |
| 6,832,905 B2 | 12/2004 | Delzer et al. |
| 6,840,929 B2 | 1/2005 | Kurata |
| 6,846,374 B2 | 1/2005 | Popp |
| 6,858,771 B2 | 2/2005 | Yoshimasa |
| 6,863,933 B2 | 3/2005 | Cramer et al. |
| 6,863,960 B2 | 3/2005 | Curro et al. |
| 6,867,345 B2 | 3/2005 | Shimoe et al. |
| 6,867,346 B1 | 3/2005 | Dopps |
| 6,878,433 B2 | 4/2005 | Curro et al. |
| 6,878,647 B1 | 4/2005 | Rezai |
| 6,880,211 B2 | 4/2005 | Jackson et al. |
| 6,891,080 B2 | 5/2005 | Minato |
| 6,904,865 B2 | 6/2005 | Klofta |
| 6,911,574 B1 | 6/2005 | Mizutani |
| 6,923,797 B2 | 8/2005 | Shinohara et al. |
| 6,923,926 B2 | 8/2005 | Walter et al. |
| 6,926,703 B2 | 8/2005 | Sugito |
| 6,929,629 B2 | 8/2005 | Drevik et al. |
| 6,939,914 B2 | 9/2005 | Qin et al. |
| 6,946,585 B2 | 9/2005 | Brown |
| 6,953,451 B2 | 10/2005 | Berba |
| 6,955,733 B2 | 10/2005 | Henry et al. |
| 6,962,578 B1 | 11/2005 | Lavon |
| 6,962,645 B2 | 11/2005 | Graef |
| 6,965,058 B1 | 11/2005 | Raidel |
| 6,969,781 B2 | 11/2005 | Graef |
| 6,972,010 B2 | 12/2005 | Pesce et al. |

(56) References Cited

U.S. PATENT DOCUMENTS

| | | |
|---|---|---|
| 6,972,011 B2 | 12/2005 | Maeda et al. |
| 6,979,564 B2 | 12/2005 | Glucksmann et al. |
| 6,982,052 B2 | 1/2006 | Daniels et al. |
| 7,001,167 B2 | 2/2006 | Venturino |
| 7,014,632 B2 | 3/2006 | Takino et al. |
| 7,015,370 B2 | 3/2006 | Watanabe |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita |
| 7,067,711 B2 | 6/2006 | Kinoshita et al. |
| 7,073,373 B2 | 7/2006 | La Fortune |
| 7,078,583 B2 | 7/2006 | Kudo |
| 7,090,665 B2 | 8/2006 | Ohashi |
| 7,108,759 B2 | 9/2006 | You |
| 7,108,916 B2 | 9/2006 | Ehrnsperger et al. |
| 7,112,621 B2 | 9/2006 | Rohrbaugh et al. |
| 7,122,713 B2 | 10/2006 | Komatsu |
| 7,125,470 B2 | 10/2006 | Graef |
| 7,132,585 B2 | 11/2006 | Kudo |
| 7,147,628 B2 | 12/2006 | Drevik |
| 7,150,729 B2 | 12/2006 | Shimada |
| 7,154,019 B2 | 12/2006 | Mishima et al. |
| 7,160,281 B2 | 1/2007 | Leminh et al. |
| 7,163,528 B2 | 1/2007 | Christon et al. |
| 7,166,190 B2 | 1/2007 | Graef |
| 7,169,136 B2 | 1/2007 | Otsubo |
| 7,183,360 B2 | 2/2007 | Daniel et al. |
| 7,189,888 B2 | 3/2007 | Wang et al. |
| 7,196,241 B2 | 3/2007 | Kinoshita |
| 7,199,211 B2 | 4/2007 | Popp et al. |
| 7,204,830 B2 | 4/2007 | Mishima |
| 7,207,978 B2 | 4/2007 | Takino |
| 7,219,403 B2 | 5/2007 | Miyamoto et al. |
| 7,220,251 B2 | 5/2007 | Otsubo et al. |
| 7,241,280 B2 | 7/2007 | Christen et al. |
| 7,250,481 B2 | 7/2007 | Jaworek et al. |
| 7,252,657 B2 | 8/2007 | Mishima |
| 7,265,258 B2 | 9/2007 | Hamilton |
| 7,270,651 B2 | 9/2007 | Adams et al. |
| 7,285,178 B2 | 10/2007 | Mischler et al. |
| RE39,919 E | 11/2007 | Dodge, II et al. |
| 7,306,582 B2 | 12/2007 | Adams et al. |
| 7,311,696 B2 | 12/2007 | Christen et al. |
| 7,311,968 B2 | 12/2007 | Ehrnsperger et al. |
| 7,312,372 B2 | 12/2007 | Miyama |
| 7,318,820 B2 | 1/2008 | LaVon et al. |
| 7,329,244 B2 | 2/2008 | Otsubo |
| 7,329,246 B2 | 2/2008 | Kinoshita |
| 7,335,810 B2 | 2/2008 | Yoshimasa et al. |
| 7,377,914 B2 | 5/2008 | LaVon |
| 7,429,689 B2 | 9/2008 | Chen |
| 7,435,244 B2 | 10/2008 | Schroer et al. |
| 7,465,373 B2 | 12/2008 | Graef |
| 7,500,969 B2 | 3/2009 | Mishima |
| 7,504,552 B2 | 3/2009 | Tamura |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi |
| 7,550,646 B2 | 6/2009 | Tamura |
| 7,563,257 B2 | 7/2009 | Nakajima |
| 7,588,561 B2 | 9/2009 | Kenmochi |
| 7,594,904 B2 | 9/2009 | Rosenfeld |
| 7,598,428 B2 | 10/2009 | Gustavsson et al. |
| 7,625,363 B2 | 12/2009 | Yoshimasa |
| 7,641,642 B2 | 1/2010 | Murai et al. |
| 7,648,490 B2 | 1/2010 | Kuroda |
| 7,652,111 B2 | 1/2010 | Hermeling et al. |
| 7,666,173 B2 | 2/2010 | Mishima |
| 7,666,174 B2 | 2/2010 | Kawakami et al. |
| 7,686,790 B2 | 3/2010 | Rasmussen et al. |
| 7,687,596 B2 | 3/2010 | Hermeling et al. |
| 7,695,461 B2 | 4/2010 | Rosenfeld |
| 7,696,402 B2 | 4/2010 | Nishikawa |
| 7,708,725 B2 | 5/2010 | Tamagawa |
| 7,717,150 B2 | 5/2010 | Manabe |
| 7,718,844 B2 | 5/2010 | Olson |
| 7,722,587 B2 | 5/2010 | Suzuki et al. |
| 7,722,590 B2 | 5/2010 | Tsuji |
| 7,727,217 B2 | 6/2010 | Hancock-Cooke |
| 7,736,351 B2 | 6/2010 | Nigam |
| 7,737,324 B2 | 6/2010 | LaVon et al. |
| 7,744,576 B2 | 6/2010 | Busam et al. |
| 7,744,578 B2 | 6/2010 | Tanio et al. |
| 7,750,203 B2 | 7/2010 | Busam et al. |
| 7,754,822 B2 | 7/2010 | Daniel et al. |
| 7,754,940 B2 | 7/2010 | Brisebois |
| 7,759,540 B2 | 7/2010 | Litvay et al. |
| 7,763,004 B2 | 7/2010 | Beck |
| 7,767,875 B2 | 8/2010 | Olson |
| 7,767,876 B2 | 8/2010 | Davis et al. |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld |
| 7,825,291 B2 | 11/2010 | Elfsberg et al. |
| 7,838,722 B2 | 11/2010 | Blessing et al. |
| 7,850,672 B2 | 12/2010 | Guidotti et al. |
| 7,851,667 B2 | 12/2010 | Becker et al. |
| 7,855,314 B2 | 12/2010 | Hanao |
| 7,857,797 B2 | 12/2010 | Kudo |
| 7,858,842 B2 | 12/2010 | Komatsu |
| 7,884,259 B2 | 2/2011 | Hanao |
| 7,888,549 B2 | 2/2011 | Jansson et al. |
| 7,910,797 B2 | 3/2011 | Nandrea |
| 7,931,636 B2 | 4/2011 | LaVon et al. |
| 7,935,207 B2 | 5/2011 | Zhao |
| 7,935,861 B2 | 5/2011 | Suzuki |
| 7,938,813 B2 | 5/2011 | Wang et al. |
| 7,942,858 B2 | 5/2011 | Francoeur |
| 7,951,126 B2 | 5/2011 | Nanjyo |
| 7,959,620 B2 | 6/2011 | Miura et al. |
| 7,982,091 B2 | 7/2011 | Konawa |
| 7,993,319 B2 | 8/2011 | Sperl |
| 8,017,827 B2 | 9/2011 | Hundorf et al. |
| 8,029,486 B2 | 10/2011 | Nakajima |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe |
| 8,124,828 B2 | 2/2012 | Kline et al. |
| 8,133,212 B2 | 3/2012 | Takada |
| 8,148,598 B2 | 4/2012 | Tsang et al. |
| 8,163,124 B2 | 4/2012 | Moriura et al. |
| 8,167,862 B2 | 5/2012 | Digiacomantonio et al. |
| 8,173,858 B2 | 5/2012 | Kuroda |
| 8,178,747 B2 | 5/2012 | Venturino et al. |
| 8,183,430 B2 | 5/2012 | Hakansson et al. |
| 8,186,296 B2 | 5/2012 | Brown et al. |
| 8,187,239 B2 | 5/2012 | LaVon et al. |
| 8,187,240 B2 | 5/2012 | Busam et al. |
| 8,198,506 B2 | 6/2012 | Venturino et al. |
| 8,211,815 B2 | 7/2012 | Baker |
| 8,236,715 B2 | 8/2012 | Schmidt et al. |
| 8,237,012 B2 | 8/2012 | Miyama |
| 8,246,594 B2 | 8/2012 | Sperl |
| 8,258,367 B2 | 9/2012 | Lawson et al. |
| 8,268,424 B1 | 9/2012 | Suzuki |
| 8,273,943 B2 | 9/2012 | Noda |
| 8,282,617 B2 | 10/2012 | Kaneda |
| 8,283,516 B2 | 10/2012 | Litvay |
| 8,317,766 B2 | 11/2012 | Naoto |
| 8,317,768 B2 | 11/2012 | Larsson |
| 8,319,005 B2 | 11/2012 | Becker et al. |
| 8,343,123 B2 | 1/2013 | Noda |
| 8,343,296 B2 | 1/2013 | Blessing et al. |
| 8,360,977 B2 | 1/2013 | Marttila |
| 8,361,047 B2 | 1/2013 | Mukai |
| 8,377,025 B2 | 2/2013 | Nakajima |
| 8,450,555 B2 | 5/2013 | Nahn et al. |
| 8,496,637 B2 | 7/2013 | Hundorf et al. |

(56) References Cited

U.S. PATENT DOCUMENTS

| | | |
|---|---|---|
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,566 B2 | 10/2013 | Jackels et al. |
| 8,569,571 B2 | 10/2013 | Kline et al. |
| 8,581,019 B2 | 11/2013 | Carlucci et al. |
| 8,603,058 B2 | 12/2013 | Sprerl et al. |
| 8,604,270 B2 | 12/2013 | Venturino et al. |
| 8,633,347 B2 | 1/2014 | Bianco et al. |
| 8,664,468 B2 | 3/2014 | Lawson et al. |
| 8,674,170 B2 | 3/2014 | Busam et al. |
| 8,734,417 B2 | 5/2014 | LaVon et al. |
| 8,766,031 B2 | 7/2014 | Becker et al. |
| 8,772,570 B2 | 7/2014 | Kawakami et al. |
| 8,784,594 B2 | 7/2014 | Blessing et al. |
| 8,785,715 B2 | 7/2014 | Wright et al. |
| 8,791,318 B2 | 7/2014 | Becker et al. |
| 8,936,584 B2 | 1/2015 | Zander et al. |
| 9,056,034 B2 | 6/2015 | Akiyama |
| 9,326,896 B2 | 5/2016 | Schaefer et al. |
| 2001/0007065 A1 | 7/2001 | Blanchard |
| 2001/0008964 A1 | 7/2001 | Kurata et al. |
| 2001/0016548 A1 | 8/2001 | Kugler et al. |
| 2001/0020157 A1 | 9/2001 | Mizutani |
| 2001/0037101 A1 | 11/2001 | Allan et al. |
| 2001/0044610 A1 | 11/2001 | Kim |
| 2002/0007167 A1 | 1/2002 | Dan |
| 2002/0007169 A1 | 1/2002 | Graef et al. |
| 2002/0016579 A1 | 2/2002 | Stenberg |
| 2002/0045881 A1 | 4/2002 | Kusibojoska et al. |
| 2002/0056516 A1 | 5/2002 | Ochi |
| 2002/0058919 A1 | 5/2002 | Hamilton et al. |
| 2002/0062112 A1 | 5/2002 | Mizutani |
| 2002/0062115 A1 | 5/2002 | Wada et al. |
| 2002/0062116 A1 | 5/2002 | Mizutani et al. |
| 2002/0065498 A1 | 5/2002 | Ohashi |
| 2002/0072471 A1 | 6/2002 | Ikeuchi et al. |
| 2002/0082575 A1 | 6/2002 | Dan |
| 2002/0087139 A1 | 7/2002 | Popp et al. |
| 2002/0095127 A1 | 7/2002 | Fish et al. |
| 2002/0102392 A1 | 8/2002 | Fish et al. |
| 2002/0115969 A1 | 8/2002 | Maeda et al. |
| 2002/0123728 A1 | 9/2002 | Graef et al. |
| 2002/0123848 A1 | 9/2002 | Schneiderman et al. |
| 2002/0151634 A1 | 10/2002 | Rohrbaugh et al. |
| 2002/0151861 A1 | 10/2002 | Klemp et al. |
| 2002/0173767 A1 | 11/2002 | Popp et al. |
| 2002/0016122 A1 | 12/2002 | Curro et al. |
| 2002/0192366 A1 | 12/2002 | Cramer et al. |
| 2002/0197695 A1 | 12/2002 | Glucksmann et al. |
| 2003/0036741 A1 | 2/2003 | Abba et al. |
| 2003/0078553 A1 | 4/2003 | Wada |
| 2003/0084983 A1 | 5/2003 | Rangachari et al. |
| 2003/0088223 A1 | 5/2003 | Vogt et al. |
| 2003/0105190 A1 | 6/2003 | Diehl et al. |
| 2003/0109839 A1 | 6/2003 | Costae et al. |
| 2003/0114811 A1 | 6/2003 | Christen et al. |
| 2003/0114816 A1 | 6/2003 | Underhill |
| 2003/0114818 A1 | 6/2003 | Benecke et al. |
| 2003/0115969 A1 | 6/2003 | Koyano et al. |
| 2003/0120235 A1 | 6/2003 | Boulanger |
| 2003/0120249 A1 | 6/2003 | Wulz et al. |
| 2003/0233082 A1 | 6/2003 | Kline et al. |
| 2003/0135176 A1 | 7/2003 | Delzer et al. |
| 2003/0135181 A1 | 7/2003 | Chen et al. |
| 2003/0135182 A1 | 7/2003 | Woon et al. |
| 2003/0139712 A1 | 7/2003 | Dodge |
| 2003/0139715 A1 | 7/2003 | Dodge |
| 2003/0139718 A1 | 7/2003 | Graef |
| 2003/0144642 A1 | 7/2003 | Dopps |
| 2003/0144644 A1 | 7/2003 | Murai et al. |
| 2003/0148684 A1 | 8/2003 | Cramer et al. |
| 2003/0148694 A1 | 8/2003 | Ghiam |
| 2003/0158530 A1 | 8/2003 | Diehl et al. |
| 2003/0158531 A1 | 8/2003 | Chmielewski |
| 2003/0158532 A1 | 8/2003 | Magee et al. |
| 2003/0167045 A1 | 9/2003 | Graef |
| 2003/0171727 A1 | 9/2003 | Graef |
| 2003/0208175 A1 | 11/2003 | Gross |
| 2003/0225385 A1 | 12/2003 | Glaug |
| 2003/0236512 A1 | 12/2003 | Baker |
| 2004/0019338 A1 | 1/2004 | Litvay et al. |
| 2004/0022998 A1 | 2/2004 | Miyamoto et al. |
| 2004/0033750 A1 | 2/2004 | Everett |
| 2004/0063367 A1 | 4/2004 | Dodge |
| 2004/0064113 A1 | 4/2004 | Erdman |
| 2004/0064115 A1 | 4/2004 | Arora |
| 2004/0064116 A1 | 4/2004 | Arora |
| 2004/0064125 A1 | 4/2004 | Justmann et al. |
| 2004/0065420 A1 | 4/2004 | Graef |
| 2004/0082928 A1 | 4/2004 | Pesce et al. |
| 2004/0097895 A1 | 5/2004 | Busam et al. |
| 2004/0122411 A1 | 6/2004 | Hancock-Cooke |
| 2004/0127131 A1 | 7/2004 | Potnis |
| 2004/0127871 A1 | 7/2004 | Odorzynski |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko et al. |
| 2004/0162536 A1 | 8/2004 | Becker et al. |
| 2004/0167486 A1 | 8/2004 | Busam et al. |
| 2004/0167489 A1 | 8/2004 | Kellenberger et al. |
| 2004/0170813 A1 | 9/2004 | Digiacomantonio et al. |
| 2004/0193127 A1 | 9/2004 | Hansson |
| 2004/0215160 A1 | 10/2004 | Chmielewski |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0236455 A1 | 11/2004 | Woltman et al. |
| 2004/0249355 A1 | 12/2004 | Tanio et al. |
| 2004/0260259 A1 | 12/2004 | Baker |
| 2005/0001929 A1 | 1/2005 | Waksmundzki et al. |
| 2005/0004543 A1 | 1/2005 | Schroer et al. |
| 2005/0004548 A1 | 1/2005 | Otsubo et al. |
| 2005/0008839 A1 | 1/2005 | Cramer et al. |
| 2005/0018258 A1 | 1/2005 | Miyagi |
| 2005/0038401 A1 | 2/2005 | Suzuki et al. |
| 2005/0070867 A1 | 3/2005 | Beruda et al. |
| 2005/0085784 A1 | 4/2005 | LeMinh et al. |
| 2005/0090789 A1 | 4/2005 | Graef |
| 2005/0101929 A1 | 5/2005 | Waksmundzki et al. |
| 2005/0137543 A1 | 6/2005 | Underhill et al. |
| 2005/0148258 A1 | 7/2005 | Chakravarty |
| 2005/0148961 A1 | 7/2005 | Sosalla et al. |
| 2005/0148990 A1 | 7/2005 | Shimoe |
| 2005/0154363 A1 | 7/2005 | Minato |
| 2005/0159720 A1 | 7/2005 | Gentilcore |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | LaVon et al. |
| 2005/0215752 A1 | 9/2005 | Popp et al. |
| 2005/0217791 A1 | 10/2005 | Costello et al. |
| 2005/0229543 A1 | 10/2005 | Tippey |
| 2005/0234414 A1 | 10/2005 | Liu et al. |
| 2005/0245684 A1 | 11/2005 | Daniel et al. |
| 2005/0288645 A1 | 12/2005 | LaVon |
| 2005/0288646 A1 | 12/2005 | LaVon |
| 2006/0004334 A1 | 1/2006 | Schlinz et al. |
| 2006/0021695 A1 | 2/2006 | Blessing et al. |
| 2006/0024433 A1 | 2/2006 | Blessing et al. |
| 2006/0069367 A1 | 3/2006 | Waksmundzki et al. |
| 2006/0069371 A1 | 3/2006 | Ohashi et al. |
| 2006/0073969 A1 | 4/2006 | Torli et al. |
| 2006/0081348 A1 | 4/2006 | Graef |
| 2006/0129114 A1 | 6/2006 | Mason et al. |
| 2006/0142724 A1 | 6/2006 | Watanabe |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt et al. |
| 2006/0178071 A1 | 8/2006 | Schmidt et al. |

(56) References Cited

U.S. PATENT DOCUMENTS

| | | |
|---|---|---|
| 2006/0184146 A1 | 8/2006 | Suzuki |
| 2006/0184149 A1 | 8/2006 | Kasai et al. |
| 2006/0189954 A1 | 8/2006 | Kudo |
| 2006/0202380 A1 | 9/2006 | Bentley |
| 2006/0206091 A1 | 9/2006 | Cole |
| 2006/0211828 A1 | 9/2006 | Daniel et al. |
| 2006/0240229 A1 | 10/2006 | Ehrnsperger et al. |
| 2006/0264860 A1 | 11/2006 | Beck |
| 2006/0264861 A1 | 11/2006 | Lavon et al. |
| 2006/0271010 A1 | 11/2006 | LaVon et al. |
| 2007/0049892 A1 | 1/2007 | Lord et al. |
| 2007/0027436 A1 | 2/2007 | Nakagawa et al. |
| 2007/0032770 A1 | 2/2007 | Lavon et al. |
| 2007/0043191 A1 | 2/2007 | Hermeling et al. |
| 2007/0043330 A1 | 2/2007 | Lankhof et al. |
| 2007/0044903 A1 | 3/2007 | Wisneski et al. |
| 2007/0049897 A1 | 3/2007 | LaVon et al. |
| 2007/0073253 A1 | 3/2007 | Miyama |
| 2007/0078422 A1 | 4/2007 | Glaug |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto |
| 2007/0118087 A1 | 5/2007 | Flohr et al. |
| 2007/0123834 A1 | 5/2007 | McDowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug |
| 2007/0219521 A1 | 9/2007 | Hird et al. |
| 2007/0219523 A1 | 9/2007 | Bruun |
| 2007/0244455 A1 | 10/2007 | Hansson et al. |
| 2007/0246147 A1 | 10/2007 | Venturino et al. |
| 2007/0255245 A1 | 11/2007 | Asp et al. |
| 2007/0282288 A1 | 12/2007 | Noda |
| 2007/0282290 A1 | 12/2007 | Cole |
| 2007/0282291 A1 | 12/2007 | Cole |
| 2008/0027402 A1 | 1/2008 | Schmidt et al. |
| 2008/0091159 A1 | 4/2008 | Carlucci et al. |
| 2008/0119810 A1 | 5/2008 | Kuroda |
| 2008/0125735 A1 | 5/2008 | Busam et al. |
| 2008/0132864 A1 | 6/2008 | Lawson et al. |
| 2008/0208154 A1 | 8/2008 | Oetjen et al. |
| 2008/0221538 A1 | 9/2008 | Zhao |
| 2008/0221539 A1 | 9/2008 | Zhao |
| 2008/0228158 A1 | 9/2008 | Sue et al. |
| 2008/0262459 A1 | 10/2008 | Kamoto |
| 2008/0268194 A1 | 10/2008 | Kim et al. |
| 2008/0274227 A1 | 11/2008 | Boatman et al. |
| 2008/0281287 A1 | 11/2008 | Marcelo |
| 2008/0294140 A1 | 11/2008 | Ecker et al. |
| 2008/0032035 A1 | 12/2008 | Schmidt et al. |
| 2008/0312617 A1 | 12/2008 | Hundorf et al. |
| 2008/0312618 A1 | 12/2008 | Hundorf et al. |
| 2008/0312619 A1 | 12/2008 | Hundorf et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312627 A1 | 12/2008 | Takeuchi |
| 2008/0312628 A1 | 12/2008 | Hundorf et al. |
| 2009/0023848 A1 | 1/2009 | Ahmed et al. |
| 2009/0056867 A1 | 3/2009 | Moriura et al. |
| 2009/0062760 A1 | 3/2009 | Wright et al. |
| 2009/0112173 A1 | 4/2009 | Bissah |
| 2009/0112175 A1 | 4/2009 | Bissah et al. |
| 2009/0157022 A1 | 6/2009 | Macdonald |
| 2009/0192035 A1 | 7/2009 | Stueven et al. |
| 2009/0240220 A1 | 9/2009 | Macdonald |
| 2009/0058994 A1 | 10/2009 | Stueven et al. |
| 2009/0247977 A1 | 10/2009 | Takeuchi |
| 2009/0258994 A1 | 10/2009 | Stueven et al. |
| 2009/0270825 A1 | 10/2009 | Wciorka et al. |
| 2009/0298963 A1 | 12/2009 | Matsumoto et al. |
| 2009/0299312 A1 | 12/2009 | Macdonald |
| 2009/0306618 A1 | 12/2009 | Kudo |
| 2009/0318884 A1 | 12/2009 | Meyer et al. |
| 2009/0326494 A1 | 12/2009 | Uchida et al. |
| 2010/0051166 A1 | 3/2010 | Hundorf et al. |
| 2010/0062165 A1 | 3/2010 | Suzuki |
| 2010/0062934 A1 | 3/2010 | Suzuki |
| 2010/0063470 A1 | 3/2010 | Suzuki |
| 2010/0068520 A1 | 3/2010 | Stueven et al. |
| 2010/0100065 A1 | 4/2010 | Bianco |
| 2010/0115237 A1 | 5/2010 | Brewer et al. |
| 2010/0121296 A1 | 5/2010 | Noda |
| 2010/0137773 A1 | 6/2010 | Gross |
| 2010/0137823 A1 | 6/2010 | Corneliusson |
| 2010/0198179 A1 | 8/2010 | Noda |
| 2010/0228210 A1 | 9/2010 | Busam et al. |
| 2010/0241096 A1 | 9/2010 | LaVon et al. |
| 2010/0241097 A1 | 9/2010 | Nigam et al. |
| 2010/0262099 A1 | 10/2010 | Klofta |
| 2010/0262104 A1 | 10/2010 | Carlucci et al. |
| 2010/0274208 A1 | 10/2010 | Gabrielii |
| 2010/0274210 A1 | 10/2010 | Noda |
| 2010/0312208 A1 | 12/2010 | Bond et al. |
| 2010/0324521 A1 | 12/2010 | Mukai |
| 2010/0324523 A1 | 12/2010 | Mukai |
| 2011/0041999 A1 | 2/2011 | Hundorf et al. |
| 2011/0060301 A1 | 3/2011 | Nishikawa et al. |
| 2011/0060303 A1 | 3/2011 | Bissah |
| 2011/0066127 A1 | 3/2011 | Kuwano |
| 2011/0071486 A1 | 3/2011 | Harada |
| 2011/0092944 A1 | 4/2011 | Sagisaka |
| 2011/0112498 A1 | 5/2011 | Nhan et al. |
| 2011/0125120 A1 | 5/2011 | Nishitani |
| 2011/0130732 A1 | 6/2011 | Jackels et al. |
| 2011/0130737 A1 | 6/2011 | Sagisaka |
| 2011/0137276 A1 | 6/2011 | Yoshikawa |
| 2011/0144602 A1 | 6/2011 | Long |
| 2011/0144604 A1 | 6/2011 | Noda |
| 2011/0144606 A1 | 6/2011 | Nandrea |
| 2011/0152813 A1 | 6/2011 | Ellingson |
| 2011/0166540 A1 | 7/2011 | Yang et al. |
| 2011/0172630 A1 | 7/2011 | Nomoto |
| 2011/0174430 A1 | 7/2011 | Zhao |
| 2011/0196330 A1 | 8/2011 | Hammons et al. |
| 2011/0208147 A1 | 8/2011 | Kawakami et al. |
| 2011/0250413 A1 | 10/2011 | Lu et al. |
| 2011/0268932 A1 | 11/2011 | Catalan et al. |
| 2011/0274834 A1 | 11/2011 | Brown et al. |
| 2011/0288513 A1 | 11/2011 | Hundorf et al. |
| 2011/0288514 A1 | 11/2011 | Kuroda |
| 2011/0295222 A1 | 12/2011 | Becker et al. |
| 2011/0319846 A1 | 12/2011 | Rinnert et al. |
| 2011/0319848 A1 | 12/2011 | McKiernan et al. |
| 2011/0319851 A1 | 12/2011 | Kudo |
| 2012/0004633 A1 | 1/2012 | R Marcelo |
| 2012/0016326 A1 | 1/2012 | Brennan et al. |
| 2012/0022479 A1 | 1/2012 | Cotton |
| 2012/0035566 A1 | 2/2012 | Sagisaka |
| 2012/0035576 A1 | 2/2012 | Ichikawa |
| 2012/0064792 A1 | 3/2012 | Bauduin |
| 2012/0071848 A1 | 3/2012 | Zhang |
| 2012/0165771 A1 | 6/2012 | Ruman et al. |
| 2012/0165776 A1 | 6/2012 | Rinnert et al. |
| 2012/0175056 A1 | 7/2012 | Tsang |
| 2012/0184934 A1 | 7/2012 | Venturino |
| 2012/0232514 A1 | 9/2012 | Baker |
| 2012/0238977 A1 | 9/2012 | Oku |
| 2012/0253306 A1 | 10/2012 | Otsubo |
| 2012/0256750 A1 | 10/2012 | Novak |
| 2012/0271262 A1 | 10/2012 | Venturino |
| 2012/0170779 A1 | 12/2012 | Rosati et al. |
| 2012/0312491 A1 | 12/2012 | Jackels et al. |
| 2012/0316046 A1 | 12/2012 | Jackels et al. |
| 2012/0316523 A1 | 12/2012 | Hippe et al. |
| 2012/0316526 A1 | 12/2012 | Rosati et al. |
| 2012/0316527 A1 | 12/2012 | Rosati et al. |

(56) References Cited

U.S. PATENT DOCUMENTS

| | | |
|---|---|---|
| 2012/0316528 A1 | 12/2012 | Kreuzer et al. |
| 2012/0316529 A1 | 12/2012 | Kreuzer et al. |
| 2012/0323195 A1 | 12/2012 | Ehrnsperger et al. |
| 2012/0323201 A1 | 12/2012 | Bissah |
| 2012/0323202 A1 | 12/2012 | Bissah |
| 2013/0035656 A1 | 2/2013 | Moriya et al. |
| 2013/0041334 A1 | 2/2013 | Prioleau |
| 2013/0178811 A1 | 7/2013 | Kikuchi et al. |
| 2013/0211354 A1 | 8/2013 | Tsuji et al. |
| 2013/0211358 A1 | 8/2013 | Kikkawa et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van De Maele |
| 2013/0310784 A1 | 11/2013 | Bryant et al. |
| 2014/0005622 A1 | 1/2014 | Wirtz et al. |
| 2014/0005623 A1 | 1/2014 | Wirtz et al. |
| 2014/0027066 A1 | 1/2014 | Jackels et al. |
| 2014/0039437 A1 | 2/2014 | Van De Maele |
| 2014/0045683 A1 | 2/2014 | Loick et al. |
| 2014/0102183 A1 | 4/2014 | Agami et al. |
| 2014/0121623 A1 | 5/2014 | Kirby et al. |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehrnsperger et al. |
| 2014/0163502 A1 | 6/2014 | Arizti et al. |
| 2014/0163503 A1 | 6/2014 | Arizti et al. |
| 2014/0163506 A1 | 6/2014 | Roe et al. |
| 2014/0163511 A1 | 6/2014 | Roe et al. |
| 2014/0171893 A1 | 6/2014 | Lawson et al. |
| 2014/0318694 A1 | 10/2014 | Blessing et al. |
| 2014/0324007 A1 | 10/2014 | Hundorf et al. |
| 2014/0324008 A1 | 10/2014 | Hundorf et al. |
| 2015/0065981 A1 | 3/2015 | Roe et al. |
| 2015/0065986 A1 | 3/2015 | Blessing et al. |
| 2015/0080837 A1 | 3/2015 | Rosati et al. |
| 2015/0080839 A1 | 3/2015 | Tapp et al. |
| 2015/0173967 A1 | 6/2015 | Kreuzer et al. |
| 2015/0173968 A1 | 6/2015 | Joseph |
| 2015/0250662 A1 | 9/2015 | Isele et al. |
| 2016/0331602 A1 | 11/2016 | Bianchi et al. |

FOREIGN PATENT DOCUMENTS

| | | |
|---|---|---|
| CA | 2308961 | 11/2000 |
| CA | 2487027 | 12/2003 |
| CA | 2561521 | 3/2007 |
| CA | 2630713 | 11/2008 |
| CA | 2636673 | 1/2009 |
| CA | 2712563 | 8/2010 |
| CA | 2702001 | 10/2010 |
| CN | 1238171 A | 12/1999 |
| CN | 2362468 Y | 2/2000 |
| CN | 1371671 | 2/2001 |
| CN | 2527254 Y | 12/2002 |
| CN | 2535020 Y | 2/2003 |
| CN | 2548609 Y | 5/2003 |
| CN | 1539391 | 10/2004 |
| CN | 1939242 | 4/2007 |
| CN | 101292930 | 10/2008 |
| CN | 201263750 | 7/2009 |
| CN | 201591689 | 9/2010 |
| CN | 201855366 U | 6/2011 |
| DE | 3205931 C2 | 9/1983 |
| DE | 3608114 A1 | 9/1987 |
| DE | 19732499 | 2/1999 |
| DE | 10204937 A1 | 8/2003 |
| EP | 083022 | 7/1983 |
| EP | 149880 | 7/1985 |
| EP | 0149880 A2 | 7/1985 |
| EP | 203289 | 12/1986 |
| EP | 0203289 A2 | 12/1986 |
| EP | 0206208 | 12/1986 |
| EP | 209561 B1 | 1/1987 |
| EP | 297411 B1 | 1/1989 |
| EP | 304957 | 3/1989 |
| EP | 374542 | 6/1990 |
| EP | 394274 | 10/1990 |
| EP | 0403832 | 12/1990 |
| EP | 481322 B1 | 4/1992 |
| EP | 530438 | 3/1993 |
| EP | 547847 | 6/1993 |
| EP | 555346 | 8/1993 |
| EP | 559476 | 9/1993 |
| EP | 591647 B2 | 4/1994 |
| EP | 597273 B1 | 5/1994 |
| EP | 601610 B2 | 6/1994 |
| EP | 632068 | 1/1995 |
| EP | 0640330 A1 | 3/1995 |
| EP | 0668066 | 9/1995 |
| EP | 685214 | 12/1995 |
| EP | 687453 | 12/1995 |
| EP | 0689817 | 1/1996 |
| EP | 0691133 | 1/1996 |
| EP | 0700673 | 3/1996 |
| EP | 0394274 | 7/1996 |
| EP | 724418 | 8/1996 |
| EP | 725613 | 8/1996 |
| EP | 725615 | 8/1996 |
| EP | 725616 | 8/1996 |
| EP | 758543 | 2/1997 |
| EP | 0761194 | 3/1997 |
| EP | 769284 | 4/1997 |
| EP | 0781537 | 7/1997 |
| EP | 783877 B1 | 7/1997 |
| EP | 787472 | 8/1997 |
| EP | 788874 B1 | 8/1997 |
| EP | 796068 | 9/1997 |
| EP | 799004 | 10/1997 |
| EP | 822794 B1 | 2/1998 |
| EP | 826351 | 3/1998 |
| EP | 844861 | 6/1998 |
| EP | 0737055 | 8/1998 |
| EP | 863733 | 9/1998 |
| EP | 971751 | 9/1998 |
| EP | 0875224 | 11/1998 |
| EP | 875224 A1 | 11/1998 |
| EP | 880955 | 12/1998 |
| EP | 891758 | 1/1999 |
| EP | 0893115 | 1/1999 |
| EP | 0724418 | 3/1999 |
| EP | 0725613 | 3/1999 |
| EP | 0725616 | 3/1999 |
| EP | 904755 | 3/1999 |
| EP | 0916327 | 5/1999 |
| EP | 925769 A2 | 6/1999 |
| EP | 933074 | 8/1999 |
| EP | 937736 | 8/1999 |
| EP | 941157 | 9/1999 |
| EP | 947549 | 10/1999 |
| EP | 951887 B1 | 10/1999 |
| EP | 0951890 | 10/1999 |
| EP | 2295493 | 10/1999 |
| EP | 2305749 | 10/1999 |
| EP | 2330152 | 10/1999 |
| EP | 953326 | 11/1999 |
| EP | 0978263 A1 | 2/2000 |
| EP | 985397 B1 | 3/2000 |
| EP | 0778762 | 4/2000 |
| EP | 1005847 | 6/2000 |
| EP | 1008333 | 6/2000 |
| EP | 1013252 B1 | 6/2000 |
| EP | 1018999 | 7/2000 |
| EP | 1019002 B1 | 7/2000 |
| EP | 1019003 B1 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1088537 A2 | 4/2001 |
| EP | 0796068 | 5/2001 |

(56) References Cited

FOREIGN PATENT DOCUMENTS

| | | | |
|---|---|---|---|
| EP | 752892 | | 7/2001 |
| EP | 1116479 | A2 | 7/2001 |
| EP | 0790839 | | 8/2001 |
| EP | 1132069 | | 9/2001 |
| EP | 1173128 | | 1/2002 |
| EP | 1175194 | B1 | 1/2002 |
| EP | 1184018 | | 3/2002 |
| EP | 1192312 | B1 | 4/2002 |
| EP | 1196122 | B2 | 4/2002 |
| EP | 1199059 | | 4/2002 |
| EP | 1199327 | | 4/2002 |
| EP | 1208824 | | 5/2002 |
| EP | 0793469 | | 6/2002 |
| EP | 1210925 | | 6/2002 |
| EP | 1224922 | | 7/2002 |
| EP | 1225857 | | 7/2002 |
| EP | 1253231 | | 10/2002 |
| EP | 1262531 | A1 | 12/2002 |
| EP | 1263374 | B1 | 12/2002 |
| EP | 0737056 | | 1/2003 |
| EP | 1275358 | | 1/2003 |
| EP | 1275361 | | 1/2003 |
| EP | 1293187 | | 3/2003 |
| EP | 1304986 | B1 | 5/2003 |
| EP | 1332742 | B1 | 8/2003 |
| EP | 1339368 | | 9/2003 |
| EP | 1374817 | | 1/2004 |
| EP | 1388334 | | 2/2004 |
| EP | 1402863 | | 3/2004 |
| EP | 962208 | | 8/2004 |
| EP | 1447066 | | 8/2004 |
| EP | 1447067 | | 8/2004 |
| EP | 1460987 | | 9/2004 |
| EP | 963749 | | 11/2004 |
| EP | 1495739 | | 1/2005 |
| EP | 1524955 | | 4/2005 |
| EP | 1920743 | | 4/2005 |
| EP | 1541103 | | 6/2005 |
| EP | 1551344 | | 7/2005 |
| EP | 1586289 | | 10/2005 |
| EP | 1588723 | | 10/2005 |
| EP | 1605882 | | 12/2005 |
| EP | 1609448 | | 12/2005 |
| EP | 1621166 | | 2/2006 |
| EP | 1621167 | | 2/2006 |
| EP | 1632206 | | 3/2006 |
| EP | 1642556 | | 4/2006 |
| EP | 1403419 | | 5/2006 |
| EP | 1656162 | | 5/2006 |
| EP | 1669046 | | 6/2006 |
| EP | 1688114 | | 8/2006 |
| EP | 2314265 | | 8/2006 |
| EP | 1723939 | | 11/2006 |
| EP | 1738727 | | 1/2007 |
| EP | 1754461 | | 2/2007 |
| EP | 1787611 | | 5/2007 |
| EP | 1813238 | | 8/2007 |
| EP | 2008626 | | 12/2008 |
| EP | 2055279 | A1 | 5/2009 |
| EP | 2093049 | | 8/2009 |
| EP | 2130522 | | 12/2009 |
| EP | 1621165 | | 4/2010 |
| EP | 2444046 | | 4/2012 |
| EP | 2532328 | | 12/2012 |
| EP | 2532329 | A1 | 12/2012 |
| EP | 2532332 | A1 | 12/2012 |
| EP | 2679210 | A1 | 1/2014 |
| EP | 2740449 | | 6/2014 |
| EP | 2740450 | | 6/2014 |
| EP | 2740452 | | 6/2014 |
| ES | 2213491 | | 8/2004 |
| FR | 2566631 | | 1/1986 |
| FR | 2583377 | | 12/1986 |
| FR | 2612770 | | 9/1988 |
| FR | 2810234 | | 12/2001 |
| GB | 1333081 | A | 8/1971 |
| GB | 1307441 | | 2/1973 |
| GB | 1513055 | | 6/1978 |
| GB | 2101468 | | 1/1983 |
| GB | 2170108 | | 7/1986 |
| GB | 2262873 | | 7/1993 |
| GB | 2288540 | A | 6/1994 |
| GB | 2354449 | | 3/2001 |
| GB | 2452260 | A | 10/2007 |
| GR | 851769 | | 11/1985 |
| IN | 0984/KOL/1999 | | 10/2005 |
| IN | 212479 | B | 3/2007 |
| IN | 208543 | B | 8/2007 |
| IN | 0980/MUM/2009 | | 6/2009 |
| JP | 5572928 | U | 5/1980 |
| JP | 598322 | U | 1/1984 |
| JP | 630148323 | U | 9/1988 |
| JP | 2107250 | | 4/1990 |
| JP | 03224481 | B2 | 10/1991 |
| JP | 04122256 | | 4/1992 |
| JP | 04341368 | | 11/1992 |
| JP | 06191505 | | 7/1994 |
| JP | 06269475 | A | 9/1994 |
| JP | 07124193 | | 5/1995 |
| JP | 08215629 | | 8/1996 |
| JP | H10295728 | | 11/1998 |
| JP | 10328232 | | 12/1998 |
| JP | 11033056 | A | 2/1999 |
| JP | 11318980 | | 11/1999 |
| JP | 11320742 | | 11/1999 |
| JP | 2000232985 | | 8/2000 |
| JP | 2000238161 | | 9/2000 |
| JP | 2001037810 | | 2/2001 |
| JP | 2001046435 | A | 2/2001 |
| JP | 2001120597 | | 5/2001 |
| JP | 2001158074 | | 6/2001 |
| JP | 2001178768 | A | 7/2001 |
| JP | 2001198157 | | 7/2001 |
| JP | 2001224626 | A | 8/2001 |
| JP | 2001277394 | | 10/2001 |
| JP | 03420481 | B2 | 11/2001 |
| JP | 2001321397 | | 11/2001 |
| JP | 2001353174 | A | 12/2001 |
| JP | 2002052042 | A | 2/2002 |
| JP | 2002065718 | | 3/2002 |
| JP | 2002113800 | A | 4/2002 |
| JP | 2002165832 | | 6/2002 |
| JP | 2002165836 | | 6/2002 |
| JP | 2002178429 | | 6/2002 |
| JP | 2002272769 | A | 9/2002 |
| JP | 2002320641 | | 11/2002 |
| JP | 2002325792 | A | 11/2002 |
| JP | 2002325799 | A | 11/2002 |
| JP | 2002369841 | A | 12/2002 |
| JP | 2003126140 | | 5/2003 |
| JP | 2003153955 | A | 5/2003 |
| JP | 2003265523 | | 9/2003 |
| JP | 2003265524 | A | 9/2003 |
| JP | 2003275237 | | 9/2003 |
| JP | 2003325563 | | 11/2003 |
| JP | 2004089269 | | 3/2004 |
| JP | 03566012 | B2 | 6/2004 |
| JP | 03568146 | B2 | 6/2004 |
| JP | 03616077 | B2 | 11/2004 |
| JP | 2004337314 | A | 12/2004 |
| JP | 2004337385 | A | 12/2004 |
| JP | 2004350864 | | 12/2004 |
| JP | 03640475 | B2 | 1/2005 |
| JP | 2005000312 | A | 1/2005 |
| JP | 03660816 | B2 | 3/2005 |
| JP | 03676219 | B2 | 5/2005 |
| JP | 03688403 | B2 | 6/2005 |
| JP | 03705943 | B2 | 8/2005 |
| JP | 03719819 | B2 | 9/2005 |
| JP | 03724963 | B2 | 9/2005 |
| JP | 03725008 | B2 | 9/2005 |
| JP | 03737376 | B2 | 11/2005 |
| JP | 2006014792 | A | 1/2006 |
| JP | 03781617 | B2 | 3/2006 |

(56) References Cited

FOREIGN PATENT DOCUMENTS

| | | |
|---|---|---|
| JP | 2006110329 | 4/2006 |
| JP | 2006513824 T | 4/2006 |
| JP | 03801449 B2 | 5/2006 |
| JP | 2006116036 A | 5/2006 |
| JP | 03850102 B2 | 9/2006 |
| JP | 03850207 B2 | 9/2006 |
| JP | 03856941 B2 | 9/2006 |
| JP | 03868628 B2 | 10/2006 |
| JP | 03874499 B2 | 11/2006 |
| JP | 03877702 B2 | 11/2006 |
| JP | 2006325639 A | 12/2006 |
| JP | 2006346021 | 12/2006 |
| JP | 03904356 B2 | 1/2007 |
| JP | 2007007455 A | 1/2007 |
| JP | 2007007456 A | 1/2007 |
| JP | 03926042 B2 | 3/2007 |
| JP | 03934855 B2 | 3/2007 |
| JP | 2007089906 A | 4/2007 |
| JP | 2007105198 A | 4/2007 |
| JP | 2007152033 A | 6/2007 |
| JP | 03986210 B2 | 7/2007 |
| JP | 03986222 B2 | 7/2007 |
| JP | 2007167453 | 7/2007 |
| JP | 2007175515 A | 7/2007 |
| JP | 2007195665 A | 8/2007 |
| JP | 2007267763 A | 10/2007 |
| JP | 2007275491 A | 10/2007 |
| JP | 04035341 B2 | 11/2007 |
| JP | 04058281 B2 | 12/2007 |
| JP | 04061086 B2 | 12/2007 |
| JP | 04092319 B2 | 3/2008 |
| JP | 2008080150 A | 4/2008 |
| JP | 2008093289 A | 4/2008 |
| JP | 04124322 B2 | 5/2008 |
| JP | 2008119081 A | 5/2008 |
| JP | 2008136739 A | 6/2008 |
| JP | 2008136877 A | 6/2008 |
| JP | 04148594 B2 | 7/2008 |
| JP | 04148620 B2 | 7/2008 |
| JP | 2008154606 A | 7/2008 |
| JP | 04162609 B2 | 8/2008 |
| JP | 04162637 B2 | 8/2008 |
| JP | 04166923 B2 | 8/2008 |
| JP | 04167406 B2 | 8/2008 |
| JP | 04173723 B2 | 8/2008 |
| JP | 04190675 B2 | 9/2008 |
| JP | 04190693 B2 | 9/2008 |
| JP | 04208338 B2 | 10/2008 |
| JP | 2008246089 | 10/2008 |
| JP | 4177770 B2 | 11/2008 |
| JP | 04230971 B2 | 12/2008 |
| JP | 2008295475 A | 12/2008 |
| JP | 2008295713 A | 12/2008 |
| JP | 04261593 B2 | 2/2009 |
| JP | 2009112590 | 5/2009 |
| JP | 04322228 B2 | 6/2009 |
| JP | 2009136601 | 6/2009 |
| JP | 2009142401 A | 7/2009 |
| JP | 2009201878 A | 9/2009 |
| JP | 04392936 B2 | 10/2009 |
| JP | 2009232987 A | 10/2009 |
| JP | 2009261777 A | 11/2009 |
| JP | 2009291473 A | 12/2009 |
| JP | 2009297048 A | 12/2009 |
| JP | 2010017342 | 1/2010 |
| JP | 04458702 B2 | 2/2010 |
| JP | 04459013 B2 | 2/2010 |
| JP | 2010022560 | 2/2010 |
| JP | 04481325 B2 | 3/2010 |
| JP | 2010051654 A | 3/2010 |
| JP | 2010063814 A | 3/2010 |
| JP | 2010063944 A | 3/2010 |
| JP | 04492957 B2 | 4/2010 |
| JP | 2010068954 A | 4/2010 |
| JP | 2010075462 A | 4/2010 |
| JP | 2010082059 A | 4/2010 |
| JP | 2010104545 A | 5/2010 |
| JP | 2010104547 A | 5/2010 |
| JP | 2010110535 A | 5/2010 |
| JP | 2010119454 A | 6/2010 |
| JP | 2010119605 A | 6/2010 |
| JP | 2010119743 A | 6/2010 |
| JP | 2010131131 A | 6/2010 |
| JP | 2010131132 A | 6/2010 |
| JP | 2010131206 | 6/2010 |
| JP | 2010131297 A | 6/2010 |
| JP | 2010136917 A | 6/2010 |
| JP | 2010136973 A | 6/2010 |
| JP | 04540563 B2 | 7/2010 |
| JP | 04587947 B2 | 9/2010 |
| JP | 2010194124 A | 9/2010 |
| JP | 2010201093 | 9/2010 |
| JP | 2010221067 | 10/2010 |
| JP | 4577766 B2 | 11/2010 |
| JP | 04620299 B2 | 11/2010 |
| JP | 04627472 B2 | 11/2010 |
| JP | 04627473 B2 | 11/2010 |
| JP | 04638087 B2 | 12/2010 |
| JP | 04652626 B2 | 12/2010 |
| JP | 2010273842 A | 12/2010 |
| JP | 2010284418 A | 12/2010 |
| JP | 2011000480 A | 1/2011 |
| JP | 2011030700 | 2/2011 |
| JP | 04693574 B2 | 3/2011 |
| JP | 2011067484 A | 4/2011 |
| JP | 2011072720 A | 4/2011 |
| JP | 2011104014 | 6/2011 |
| JP | 2011104122 A | 6/2011 |
| JP | 2011120661 A | 6/2011 |
| JP | 2011125360 A | 6/2011 |
| JP | 2011125537 | 6/2011 |
| JP | 04776516 B2 | 7/2011 |
| JP | 2011130797 A | 7/2011 |
| JP | 2011130799 A | 7/2011 |
| JP | 2011156032 A | 8/2011 |
| JP | 2011156070 A | 8/2011 |
| JP | 2011156254 | 8/2011 |
| JP | 04824882 B2 | 9/2011 |
| JP | 4850272 B2 | 10/2011 |
| JP | 04855533 B2 | 11/2011 |
| JP | 2011239858 | 12/2011 |
| JP | 04931572 B2 | 2/2012 |
| JP | 04937225 B2 | 3/2012 |
| JP | 04953618 B2 | 3/2012 |
| JP | 04969437 B2 | 4/2012 |
| JP | 04969640 B2 | 4/2012 |
| JP | 4971491 B2 | 4/2012 |
| JP | 04974524 B2 | 4/2012 |
| JP | 04979780 B2 | 4/2012 |
| JP | 05016020 B2 | 6/2012 |
| JP | 05027364 B2 | 6/2012 |
| JP | 2012115378 | 6/2012 |
| JP | 05031082 B2 | 7/2012 |
| JP | 05042351 B2 | 7/2012 |
| JP | 05043569 B2 | 7/2012 |
| JP | 05043591 B2 | 7/2012 |
| JP | 05046488 B2 | 7/2012 |
| JP | 2012125452 | 7/2012 |
| JP | 2012125625 A | 7/2012 |
| JP | 05053765 B2 | 8/2012 |
| JP | 05070275 B2 | 8/2012 |
| JP | 05079931 B1 | 9/2012 |
| JP | 05080189 B2 | 9/2012 |
| JP | 05084442 B2 | 9/2012 |
| JP | 05084476 B2 | 9/2012 |
| JP | 5085770 B2 | 9/2012 |
| JP | 05089269 B2 | 9/2012 |
| JP | 2012179286 | 9/2012 |
| JP | 05113146 B2 | 10/2012 |
| JP | 05129536 B2 | 11/2012 |
| JP | 05105884 B2 | 12/2012 |
| JP | 5715806 B2 | 5/2015 |
| KR | 20010005620 | 1/2001 |
| KR | 20020035634 | 5/2002 |

(56) References Cited

FOREIGN PATENT DOCUMENTS

| | | |
|---|---|---|
| KR | 20080028771 | 4/2008 |
| SE | 9400916 | 3/1994 |
| SE | 9704893 | 12/1997 |
| WO | WO9015830 | 12/1990 |
| WO | WO9219198 | 11/1992 |
| WO | WO9321237 | 10/1993 |
| WO | WO9321879 | 11/1993 |
| WO | WO9510996 | 4/1995 |
| WO | WO9511652 | 5/1995 |
| WO | WO9514453 | 6/1995 |
| WO | WO9515139 | 6/1995 |
| WO | WO9516424 | 6/1995 |
| WO | WO9516746 | 6/1995 |
| WO | WO9519753 | 7/1995 |
| WO | WO9521596 | 8/1995 |
| WO | WO9524173 | 9/1995 |
| WO | WO9526209 | 10/1995 |
| WO | WO9529657 | 11/1995 |
| WO | WO9532698 | 12/1995 |
| WO | WO9534329 | 12/1995 |
| WO | WO9616624 | 6/1996 |
| WO | WO9619173 | 6/1996 |
| WO | WO96029967 | 10/1996 |
| WO | WO9711659 | 4/1997 |
| WO | WO9717922 | 5/1997 |
| WO | WO9724096 | 7/1997 |
| WO | WO9816179 | 4/1998 |
| WO | WO9816180 | 4/1998 |
| WO | WO9843684 | 10/1998 |
| WO | WO9913813 | 3/1999 |
| WO | WO9934841 | 7/1999 |
| WO | WO9951178 | 10/1999 |
| WO | WO200000235 | 1/2000 |
| WO | WO200032145 | 6/2000 |
| WO | WO200059430 | 10/2000 |
| WO | WO200115647 | 3/2001 |
| WO | WO200126596 | 4/2001 |
| WO | WO200135886 | 5/2001 |
| WO | WO200207663 | 1/2002 |
| WO | WO200232962 | 4/2002 |
| WO | WO2002064877 | 8/2002 |
| WO | WO2002067809 | 9/2002 |
| WO | WO2003009794 | 2/2003 |
| WO | WO2003039402 | 5/2003 |
| WO | WO2003053297 | 7/2003 |
| WO | WO03079946 | 10/2003 |
| WO | WO03101622 | 12/2003 |
| WO | WO2003105738 | 12/2003 |
| WO | WO2004021946 | 3/2004 |
| WO | WO2004049995 | 6/2004 |
| WO | WO2004071539 | 8/2004 |
| WO | WO2004084784 | 10/2004 |
| WO | WO2004105664 | 12/2004 |
| WO | WO2005/018694 | 3/2005 |
| WO | WO2005087164 | 9/2005 |
| WO | WO2005/102237 | 11/2005 |
| WO | WO2006104024 | 5/2006 |
| WO | WO2006059922 | 6/2006 |
| WO | WO2006062258 | 6/2006 |
| WO | WO2006066029 | 6/2006 |
| WO | WO2006083584 | 8/2006 |
| WO | WO2006134904 | 12/2006 |
| WO | WO2006134906 | 12/2006 |
| WO | WO2007000315 | 1/2007 |
| WO | WO2007046052 | 4/2007 |
| WO | WO2007047598 | 4/2007 |
| WO | WO2007049725 | 5/2007 |
| WO | WO2007061035 | 5/2007 |
| WO | WO2007141744 | 12/2007 |
| WO | WO2007142145 | 12/2007 |
| WO | WO2007148502 | 12/2007 |
| WO | WO2008018922 | 2/2008 |
| WO | WO2008065945 | 6/2008 |
| WO | WO2008146749 | 12/2008 |
| WO | WO2008155699 | 12/2008 |
| WO | WO2009004941 | 1/2009 |
| WO | WO2009005431 | 1/2009 |
| WO | WO2009139248 | 1/2009 |
| WO | WO2009139255 | 1/2009 |
| WO | WO2009041223 | 4/2009 |
| WO | WO2009096108 | 8/2009 |
| WO | WO2009107435 | 9/2009 |
| WO | WO2009122830 | 10/2009 |
| WO | WO2009152018 | 12/2009 |
| WO | WO2009155264 | 12/2009 |
| WO | WO2009155265 | 12/2009 |
| WO | WO2010071508 | 6/2010 |
| WO | WO2010074319 | 7/2010 |
| WO | WO2010107096 | 9/2010 |
| WO | WO2010114052 | 10/2010 |
| WO | WO2010117015 | 10/2010 |
| WO | WO2010118272 | 10/2010 |
| WO | WO2011053044 | 5/2011 |
| WO | WO2011118725 | 9/2011 |
| WO | WO2011118842 | 9/2011 |
| WO | WO2011145653 | 11/2011 |
| WO | WO2011150955 | 12/2011 |
| WO | WO2011163582 | 12/2011 |
| WO | WO2012002252 | 1/2012 |
| WO | WO2012014436 | 2/2012 |
| WO | WO2012042908 | 4/2012 |
| WO | WO2012043077 | 4/2012 |
| WO | WO2012043078 | 4/2012 |
| WO | WO2012052172 | 4/2012 |
| WO | WO2012043082 | 5/2012 |
| WO | WO2012067216 | 5/2012 |
| WO | WO2012073499 | 6/2012 |
| WO | WO2012074466 | 6/2012 |
| WO | WO201291016 | 7/2012 |
| WO | WO2012090508 | 7/2012 |
| WO | WO2012101934 | 8/2012 |
| WO | WO2012102034 | 8/2012 |
| WO | WO2012117764 | 9/2012 |
| WO | WO2012117824 | 9/2012 |
| WO | WO2012132460 | 10/2012 |
| WO | WO2012170778 | 12/2012 |
| WO | WO2012170779 | 12/2012 |
| WO | WO2012170781 | 12/2012 |
| WO | WO2012170808 | 12/2012 |
| WO | WO2012174026 | 12/2012 |
| WO | WO2012177400 | 12/2012 |
| WO | WO2013001788 | 1/2013 |
| WO | WO2013046701 | 4/2013 |
| WO | WO2013060733 | 5/2013 |
| WO | WO2014073636 | 5/2014 |
| WO | WO2014078247 | 5/2014 |

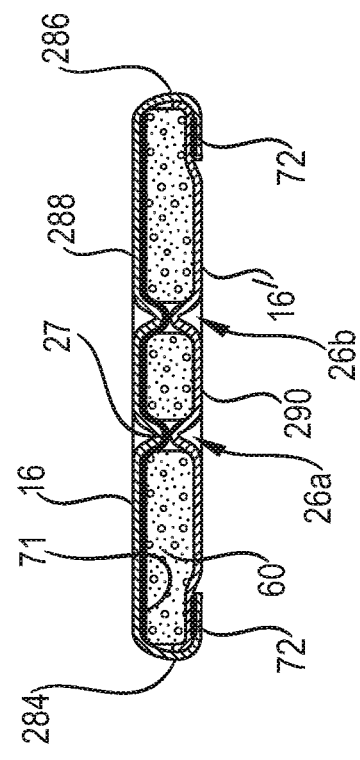
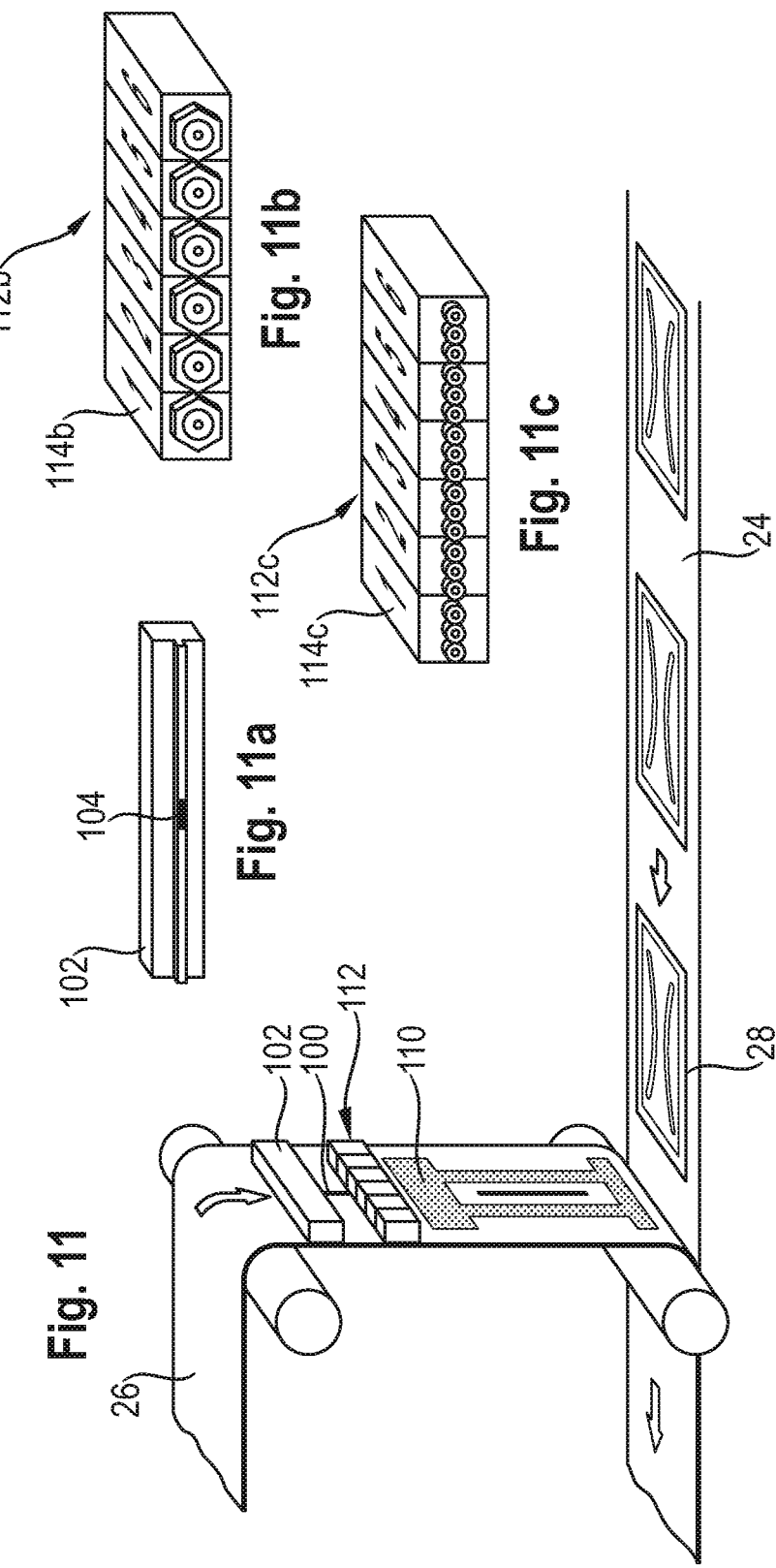

ABSORBENT ARTICLE WITH IMPROVED CORE-TO-BACKSHEET ADHESIVE

FIELD OF THE INVENTION

The invention relates to personal hygiene absorbent articles of the type worn in the crotch region of an individual to absorb body exudates. The absorbent articles may in particular be baby and toddler diapers (including training pants), feminine sanitary pads and/or adult incontinence articles. The present invention relates more particularly to the attachment of the absorbent core to the backsheet of these articles.

BACKGROUND OF THE INVENTION

Absorbent articles for personal hygiene of the type indicated above are designed to absorb and contain body exudates, in particular large quantity of urine. These absorbent articles comprise several layers providing different functions, for example a wearer-facing liquid permeable topsheet, a garment-facing liquid impermeable backsheet and in-between an absorbent core, among other layers. The function of the absorbent core is typically to absorb and retain the exudates for a prolonged amount of time, minimize re-wet to keep the wearer dry and avoid soiling of clothes or bed sheets.

The majority of currently marketed absorbent articles comprise as absorbent material a blend of comminuted wood pulp with superabsorbent polymers (SAP) in particulate form, also called absorbent gelling materials (AGM), see for example U.S. Pat. No. 5,151,092 (Buell). Cores having an absorbent material consisting essentially of SAP (so called "airfelt-free" cores) have also been proposed, see for example WO95/11652 (Tanzer), U.S. Pat. No. 6,790,798 (Suzuki), WO2008/155699 (Hundorf), or WO2012/052172 (Van Malderen). Absorbent cores with slits or grooves have also been proposed, typically to increase the fluid acquisition properties of the core or to act as a folding guide. WO2012/170778 (Rosati et al., see also WO2012/170779, WO2012/170781 and WO2012/170808) discloses absorbent structures that comprise superabsorbent polymers, optionally a cellulosic material, and at least a pair of substantially longitudinally extending channels.

The various components of an article are typically attached to another so that they stay in place before and during usage. Typical attachment means are gluing, heat and/or pressure bonding, ultrasonic bonding. The attachment means will be chosen by the manufacturer to balance costs of the equipment, cost of the glue material and performance required. Absorbent cores are typically attached to the backsheet by gluing, in particular by spraying the whole or most of the area between the core and the backsheet with a melt blow type adhesive. In presence of absorbent cores with slits or grooves, it may be beneficial to leave unglued areas between the absorbent core and backsheet components.

Alternative core-to-backsheet gluing methods have been proposed. WO2012/170341A1 (Hippe) discloses a diaper having a reduced core-to-backsheet gluing area. In Hippe, the absorbent core is attached to the backsheet only in certain, limited, areas to reduce the formation of buckles and wrinkles in the backsheet during usage, as well as the see-through of urine stains from the absorbent core through the backsheet. In particular, these unglued areas between absorbent core and backsheet are beneficial especially when the absorbent core comprises channels, which are areas substantially free of super absorbent material, and the core to backsheet attachment is provided only outside of the channels areas. This further improves the conformity of the absorbent article especially in loaded state.

However, when glued and unglued areas are present side to side between core and backsheet, boundary lines are inevitably created between the glued areas and the non-glued areas. The inventors observed that these boundary lines are the object of stress during the manufacturing of absorbent articles and can be at the origin of failures in the backsheet film. In particular when the boundary line is created by a discontinuous pattern of application of the glue (within the glue application area) like spirals or swirls this phenomenon is even more evident.

The backsheet materials for absorbent articles such as diapers are normally formed by a laminate of a very thin plastic film with a nonwoven where the nonwoven is oriented outside of the article (on the garment facing side) so to provide fluid barrier properties together with a soft touch. The two materials are called backsheet film and backsheet nonwoven respectively.

Thin plastic films are preferred as backsheet film because this reduces the environmental impact of the absorbent articles and increases the softness of the film, which is a very important feature for the consumers, however, in general, the thinner the backsheet film the lower its tensile strength. A low tensile strength increases the likelihood of failures during production or wear of the absorbent article. Moreover additional additives like Calcium Carbonate can be added to the backsheet film composition to produce porous backsheet films which enable water vapor transfer (also known as "breathable films"), and improve dryness of the skin during wear. Breathable backsheet films tend to have lower tensile strength and are in general more fragile than non-porous films of the same thickness. The lamination of the backsheet film with backsheet nonwoven enables to have a total tensile strength higher than the one of each individual layer. This lamination can be done for example with glue patterns like slots, spirals, or the like. Areas without glue between the backsheet film and backsheet nonwoven are desired to improve softness of the laminate, and the inventors have found that in those areas the backsheet film is more susceptible to fail and tear during manufacturing or wear of the absorbent article. Therefore a balance must be found between the film properties, the glue patterns used on the backsheet laminate between backsheet film and backsheet nonwoven, the glue distribution between the backsheet film and the core, each material tensile properties and the glue bonding strength to help withstand the stresses, especially on the boundary lines of the core to backsheet glue application area in high speed manufacturing.

Absorbent articles such as diapers are typically built on high speed lines which travel at speed that can be higher than 30 km/h, and at the end of the process, they are decelerated for folding and packaging from 30 km/h to 0 in a fraction of a second. This deceleration of the absorbent article is normally accomplished by nonmoving or low speed mechanical parts of the line, like plates, belts or fingers that holds the absorbent article by the outer layers, in particular the garment side of the backsheet. In the areas where core and backsheet are fully attached, the two components travel together and the kinetic energy of the product is dissipated along the full area in contact with the low speed or static parts of the production line. However the inventors observed that in areas where the core and backsheet are decoupled (i.e. not glued together), the absorbent core, which has a much higher mass and kinetic energy than the backsheet substrate, while decelerating releases a part of this energy on the boundary lines between glued and non-glued areas, so that backsheet film can tear along the attachment boundary lines. The inventors have also observed that in the areas where the backsheet is not fully glued to the nonwoven, small folds or pleats can be formed on the backsheet laminate.

The formation of folds or pleats on the backsheet negatively impact the quality appearance of the product, and, especially on the boundary lines separating glued and non glued areas between core and backsheet, can create "spot bonds" where the film stick to itself or to the absorbent core while folded. When the user of the absorbent article, e.g. of a diaper, picks it up from the package the article is normally folded. Before use the article is typically unfolded and stretched longitudinally, and stress can be concentrated on these spot bonds, and can originate tears on the backsheet, or the backsheet film.

Glues having a reduced bonding strength can of course reduce the occurrence of backsheet tearing, however the glue must ensure enough bonding strength between core and backsheet so to prevent collapse of the core once loaded with fluids. Also backsheet tearing could be reduced by increasing the thickness of the film or decreasing the manufacturing line speed, but both these solution are in general not acceptable as they reduce the efficiency of manufacturing and the environmental impact of the articles, also impacting manufacturing costs.

The present invention is directed to an improved core to backsheet gluing method and absorbent articles employing this improved gluing method. In the present invention the applicant has surprisingly identified a parameter range which provides a sufficient bonding strength while preventing the occurrence of backsheet rupture especially for absorbent articles with unglued areas between backsheet and core.

SUMMARY OF THE INVENTION

The present invention is directed to an absorbent article for personal hygiene having a wearer-facing side, a garment-facing side and a longitudinal axis, the article comprising:
- a topsheet on the wearer-facing side;
- a backsheet on the garment-facing side, said backsheet having a wearer facing surface and a garment facing surface,
- an absorbent core between the topsheet and the backsheet, the absorbent core having a wearer facing surface and a garment facing surface, said absorbent core comprising an absorbent material said absorbent material comprising a superabsorbent polymer;
- said backsheet comprising a plastic film on said wearer facing surface, said plastic film having a longitudinal tear strength measured in N/cm;
- said absorbent core being attached to said backsheet by a first glue having a first glue application area and a first glue application pattern, such that at least a continuous area of 10 mm in longitudinal direction and 25 mm in transversal direction of the core surface is unattached to said backsheet by said first glue or by any other means of attachment,
- said absorbent article having, in said first glue application area, a core-to-backsheet peel strength measured in N/cm,
- said article being characterized by having a core-to-backsheet peel strength in the range between 10 and 40% of said longitudinal tear strength of said plastic film.

The present invention is also directed to a process for making an absorbent article according to the invention. In particular, such process comprises the following steps for attaching the absorbent core to the backsheet:
- applying a first glue on the surface of the backsheet or of the absorbent core on a first glue application area such that at least at least a continuous area of 10 mm in longitudinal direction and 25 mm in transversal direction of the core surface is unattached to said backsheet by said first glue or by any other means of attachment,
- bringing the core of the absorbent article and the backsheet in contact so that core-to-backsheet peel strength in the range between 10 and 40% of said longitudinal tear strength of said plastic film.

For "unattached" it is meant not only that there is no glue applied between core and backsheet but also that in these areas there are no other bonding means such as mechanical bindings, stitches, fusion bonding, ultrasound bonding or any other bonding means. As a result in the unattached areas core and backsheet are free to move one with respect to the other.

In absorbent articles according to the present invention at least 20% of the core surface may be unattached to the backsheet.

The inventors have found that in an absorbent article wherein the core and the backsheet are not entirely attached to each other, and especially wherein the first glue is applied with a discontinuous pattern within the first glue application area, the occurrence of backsheet ruptures during manufacturing and usage can be prevented by controlling the core-to-backsheet peel strength (i.e. the peak of the force required to separate core and backsheet) at a level between 10 and 40%, preferably 10 to 30% of the longitudinal tear strength of the backsheet film (i.e. the tensile strength of the backsheet film measured along the longitudinal direction of the absorbent article). This can be achieved for example by selecting the pattern of application of the first glue within the first glue application area so to deliver more numerous but less strong bonding points between the core and the backsheet (e.g. increasing the density of the pattern while maintaining the same average amount of glue within the application area). This solution in particular also allows maximizing the shear bonding strength between the core and backsheet substrate to prevent the core from collapsing when loaded with fluids.

In general a skilled person can modify peel strength and tear strength acting on known variables such as selecting glues and film materials, optimizing the glue basis weight and modifying the glue application pattern within the glued areas.

In particular when the absorbent core of the absorbent article includes core channels, an additional second glue having a second glue application area, different from the first glue application area can be advantageously used. Preferably the first glue application area and the second glue application area do not overlap.

When used in the presence of channels the second glue application area is at least partially present between the channels whereas the first glue application area described above is at least partially outside the area between the channels. The first channel and the second channel are at least partially not attached by the first glue and second glue, or otherwise, to the backsheet. Advantageously, the absorbent core and the backsheet may only be attached by the first glue and the second glue.

As mentioned the inventors have surprisingly found that during the article making process, shearing forces on the backsheet or the core can concentrate along the boundary of the first glue application area and rupture the backsheet substrate. The inventors have found that in presence of the first and second glue, the forces over the backsheet substrate are better distributed, improving not only the anchoring of the core but also reducing failures or fatigue on the backsheet during the making or wear of the absorbent article, however backsheet failures have still been observed even in the presence of a second glue unless the first glue is selected according to the present invention.

The gluing method of the present invention may be particularly useful for absorbent articles comprising relatively high amount of SAP.

The channels may be in particular areas substantially free of absorbent material and which are surrounded by absorbent material. If the absorbent core has a core wrap, the top layer of the core wrap can be bonded to the bottom layer of the core wrap through the channel areas. The first channel and the second channel may be longitudinally extending and have a length as projected on the longitudinal axis which is at least 25% of the length of the absorbent core.

The second glue, which is at least partially applied between the channels, may preferably have, within the second glue application area, a second glue application pattern which is continuous. By "continuous" it is meant that the glue forms a uniform layer or coating that covers substantially the whole surface of the area on which it is applied. A continuous pattern can be typically obtained by direct application of the glue on the substrate, such as by slot coating or printing of the glue. A continuous pattern in general allows a good distribution of stress over the glue boundary line and therefore the boundaries of the second glue application area, if applied in a continuous pattern, will not be the object of stresses which can cause backsheet tears.

The first glue application pattern may be advantageously discontinuous. "Discontinuous" refers to a glue pattern which does not form a continuous layer on the application area. A discontinuous pattern may for example comprise glue filaments, swirls, miniswirls, glue fibers or the like creating a more or less regular glue web with relatively large spaces, at a microscopic level, which are not covered by the glue between the glue filaments or fibers. Discontinuous glue patterns are typically obtained by non-contact application method such as spraying or spiral glue applications. For example a discontinuous glue pattern may comprise one and typically a plurality of large swirls, mini swirls or random patterns. If a second glue is present, the first glue application area may thus be larger than the second glue application area; in particular the first glue application area may be over 3 times larger, or over 5 times larger, than the second glue application area. A discontinuous first glue application pattern may advantageously be used to cover large areas of the core-to-backsheet interface as it typically requires less glue material per unit of surface. The inventors have however observed that discontinuous glue patterns increases the stress on the glue boundary area during manufacturing being at the origin of potential material failure.

The first glue application area may, at least portion-wise, extend substantially along the full length of the absorbent core. In particular there may be a first longitudinally extending portion on one side of the longitudinal axis and a second longitudinally extending portion on the other side of the longitudinal axis. This provides for a secure attachment of the absorbent core along its full length. The first glue application area may further more extend at least portion-wise along the full length of the backsheet, thus beyond the front and back edges of the core. This may be desirable for providing further attachment of the backsheet with other components of the article in particular the topsheet. The first glue application area may be also relatively large in the region of the front edge and the back edge of the core to provide for a stronger core-backsheet attachment in these areas, in particular to attach securely the corners of the core to the backsheet.

The first glue may be advantageously applied by a non-contact applicator, typically a glue spray nozzle providing at least one and typically a plurality of large swirls, mini swirls or random glue patterns. In particular it can applied by a plurality of nozzles disposed in parallel, wherein for each article, at least some of the nozzles are turned on and off to provide a first glue application areas comprising longitudinally extending glue application areas of different lengths (intermittent applications of the glue). This can allow reducing the consumption of the first glue by applying the glue only in the desired areas, in particular wherein the first glue application area generally defines a roman II numeral shape.

In the case where a second glue is present, the first glue can be applied as described above while the second glue, applied between the channels, can be applied in a continuous pattern for example by a contact applicator, such as a slot-coater.

BRIEF DESCRIPTION OF THE DRAWINGS

FIG. 10 is a transversal cross-section of the core of FIG. 9;

FIG. 11 is a schematic sketch of a process for applying the core to backsheet glue distribution;

FIG. 11a,b,c schematically illustrate three different applicators that may be used to apply a glue;

DETAILED DESCRIPTION OF THE INVENTION

Introduction

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular" and the likes also qualify features which are not intended to limit the scope of the claims unless specifically indicated to do so.

Unless indicated otherwise, the description and claims refer to the absorbent core and article before use (i.e. dry, and not loaded with a fluid) and conditioned at least 24 hours at 21° C.+/−2° C. and 50+/−20% Relative Humidity (RH).

The invention will now be further illustrated with reference to the embodiments as described in the Figures. For ease of discussion, the absorbent article and its components will be discussed with reference to the numerals referred to in these Figures. However it should be understood that these exemplary embodiments and the numerals are not intended to limit the scope of the claims, unless specifically indicated. Dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

When the term "basis weight" is used with reference to a glue application, this indicates the amount of glue present in a unit area, and in general (unless differently specified) is referenced to the area of application of the glue only (and not to the entire area of the article).

Figure 1A:
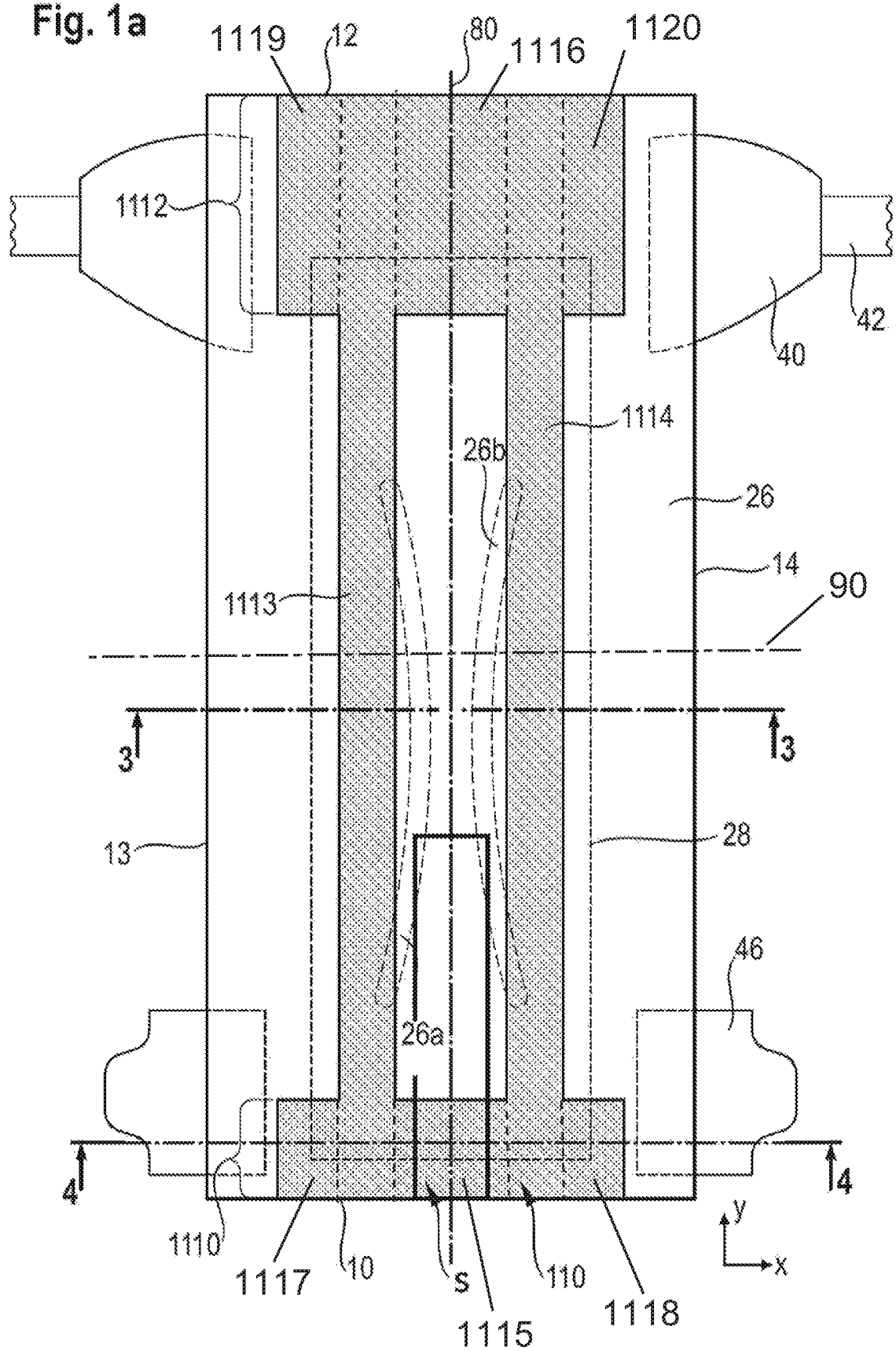
FIG. 1a shows a backsheet with a glue distribution according to the invention, with the outline of the absorbent core and its channels shown in dotted lines, the rest of the article being omitted for readability.
Figure 1B:
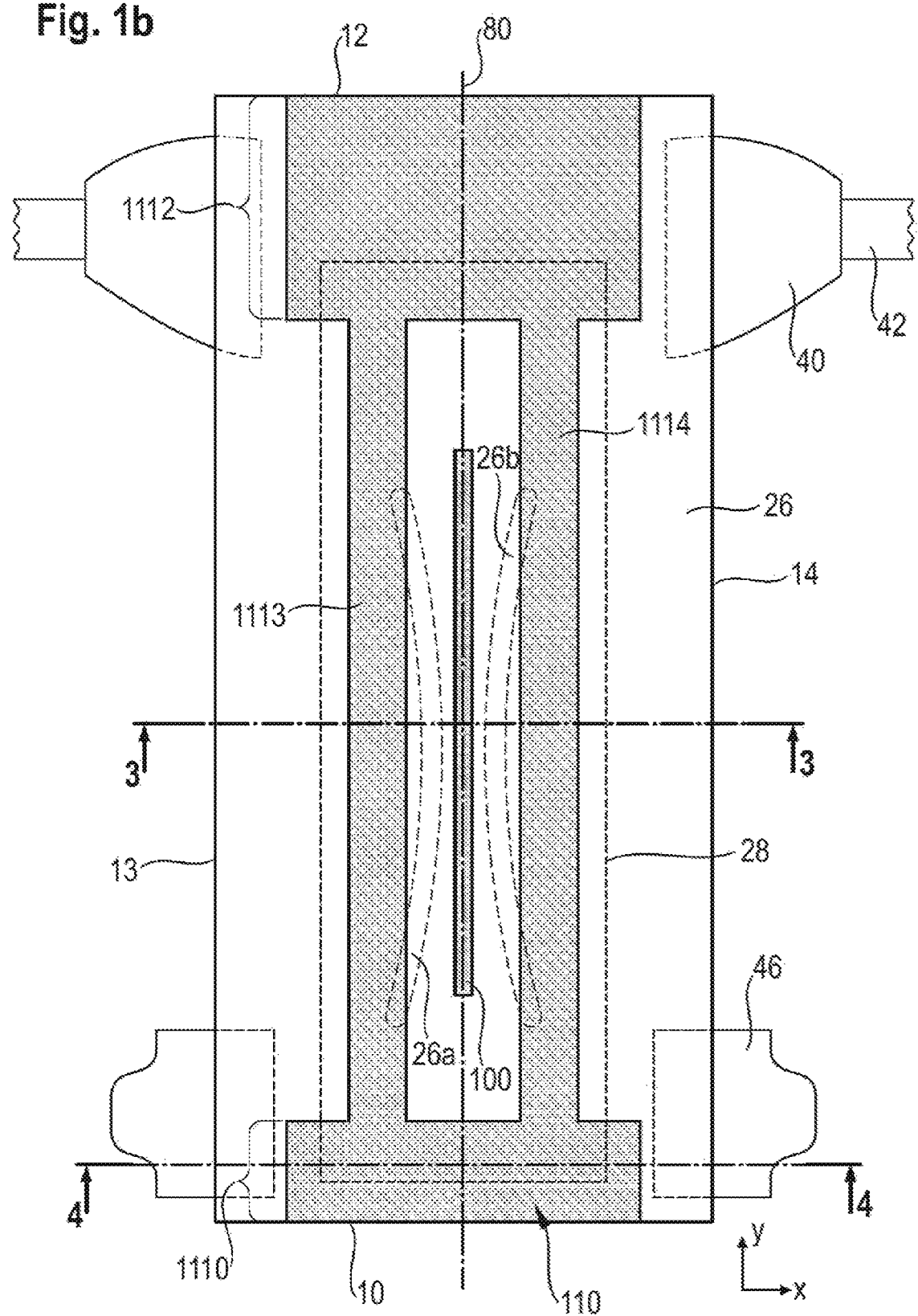
FIG. 1b shows a backsheet with a glue distribution according to the invention, with the outline of the absorbent core and its channels shown in dotted lines, and a strip of second glue between the channels, the rest of the article being omitted for readability.

General Description of FIGS. 1a and 1b

Figure 2:
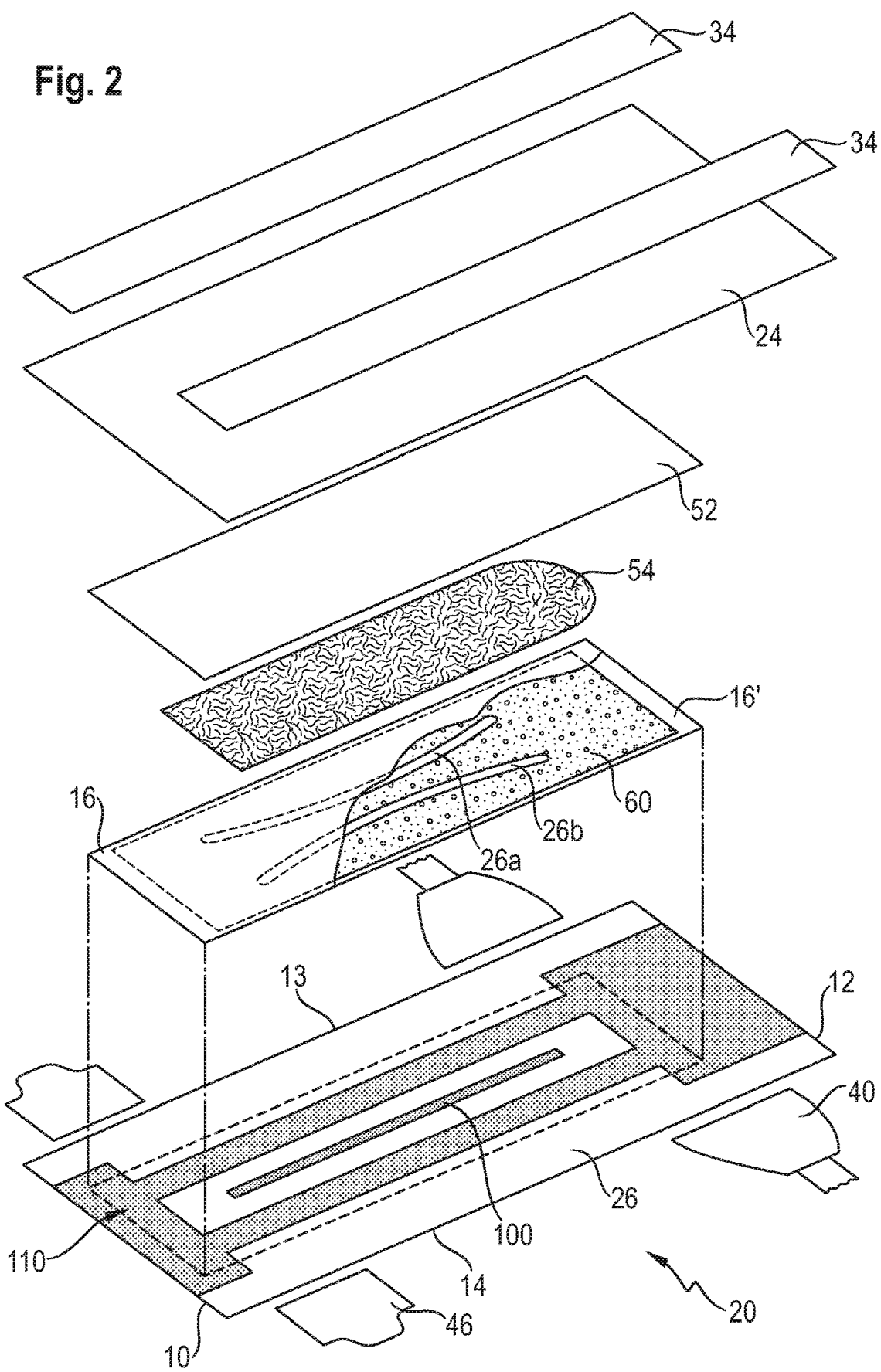
FIG. 2 shows a schematic exploded view of some of the main components of an absorbent article, including the backsheet of FIG. 1b.

FIG. 1a shows an exemplary core-to-backsheet gluing distribution usable in the present invention. The term "glue distribution" meaning the combination of glue application areas, not to be confused with the "glue application pattern" which is the pattern by which a glue is applied within a glue application area. For readability, the backsheet 26 is represented in continuous line and the contour of the absorbent core 28 and of the channels 26a, 26b in broken lines, with other layers of the articles such as the topsheet not displayed. The article represented is a so-called taped diaper, which comprise back ears 40 with releasable tapes 42 which can affixed to a so-called landing zone (not represented) on the front waist of the garment-facing side of the article. The article represented also comprises front ears 46 which provide a better coverage of the diaper along the front waist of the user. Of course, the same core-to-backsheet gluing distribution may also be used in so-called pant diapers which have pre-sealed side edges, in diapers where the core has no channels, or combined with a second glue pattern as exemplified by the article shown in FIG. 1b. Some additional layers and components of the article are shown in FIG. 2, as will be discussed further below.

The absorbent article 20 comprises a front edge 10, a back edge 12, and two longitudinally extending side (lateral) edges 13, 14. The front edge 10 is the edge of the article which is intended to be placed towards the front of the user when worn, and the back edge 12 is the opposite edge. The absorbent article is notionally (i.e. virtually) divided by a longitudinal axis 80 extending from the front edge to the back edge of the article and dividing the article in two substantially symmetrical halves relative to this axis, when viewing the core in the plane formed by the longitudinal direction (y) and the transversal direction (x) and by a transversal axis 90 dividing the article in two halves along the transverse direction. The longitudinal direction extends along the length of the article, and the transversal direction is perpendicular to the longitudinal direction.

For ease of discussion, the exemplary absorbent article is represented in a flat state extending in a transversal direction and a longitudinal direction. If some part of the article is under tension due to elasticized components, the article may be typically flattened using clamps along the periphery of the article and/or a sticky surface, so that the topsheet and backsheet can be pulled taut so as to be substantially flat. Closed articles such as training pant may be cut open along the side seams to apply them on a flat surface. Unless otherwise indicated, dimensions and areas disclosed herein apply to the article in this flat-out configuration. The article has a length L" as measured along the axis 80 from the back edge to the front edge.

The backsheet 26 may be generally rectangular as shown in the Figures. Shaped backsheets having a narrower waist thus forming an hour-glass shape are also known. The backsheet may then form front and back ears thus eliminating the need for additional material for these components. However this construction has other disadvantages such as having to cut-out materials resulting in waste and making it more difficult to elasticize the back ears for example.

Figure 9:
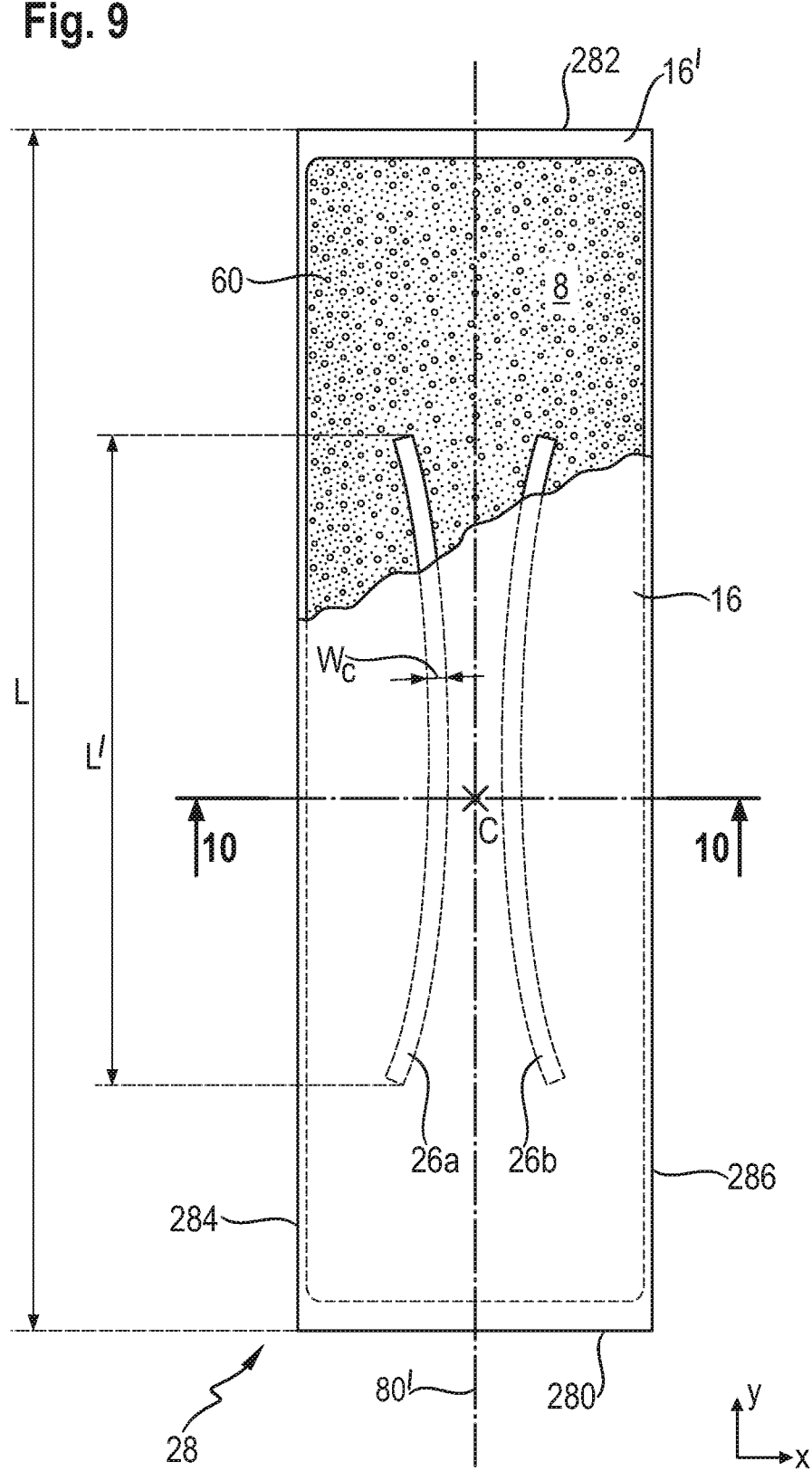
FIG. 9 is a top side view of an exemplary absorbent core in isolation.

The absorbent core 28 of this exemplary absorbent article includes channels 26a, 26b (which as mentioned above are an optional feature) shown in broken lines on FIG. 1a and FIG. 1b, and in isolation on FIG. 9. The channels 26a, 26b when present are generally longitudinally extending and may be mirror image of each other relative to the longitudinal axis. The channels may be curved, as shown in FIG. 1a and FIG. 1b, but the channels may be also straight, in particular straight and orientated in the longitudinal direction. The same gluing method for core to backsheet attachment can clearly also be applied to absorbent articles having no channels in the absorbent core. The core-to-backsheet gluing distribution will now be described in details in the following paragraphs.

First Glue Application Area 110

This first glue application area is mainly required to provide the structural support of the loaded core while wearing and prevent the absorbent core from collapsing. The first glue application area is at least partially outside the area between the channels 26a,b, in particular, the first glue may be completely absent from the area between the channels. In presence of a second glue 100, the first glue 110 can have a different application area than the first glue 100. This allows providing the second glue area with different properties than the first glue area. As indicated previously, the second glue is entirely optional and can be excluded as shown by the example in FIG. 1a. When present, as in FIG. 1b, the second glue has an application area 100. The second glue may require a precise deposition on a relatively narrow area at a higher basis weight of glue. The first glue application area 110 covers a relatively large area, several times larger than the second glue application area (when present). By providing a large area of attachment the between the core and the backsheet, the first glue ensures the overall stability of the core within the chassis of the article when dry or loaded.

The first glue may be advantageously applied at a low basis weight within the application. For example, the first glue may be applied at a basis weight of between 0.5 to 9 gsm (grams per square meter), in particular 2 to 4 gsm in the application area.

Various designs for the first glue area 110 are possible to maximize the stability of the dry and wet core. The first glue area may be unitary, as illustrated on FIGS. 1*a* and 1*b*, 5-7 and 13, but it is not excluded that it comprises discrete macroscopic sub-areas or portions separated from another, as for example shown on FIG. 8 with two longitudinally extending discrete portions 1113, 1114.

Figure 13:
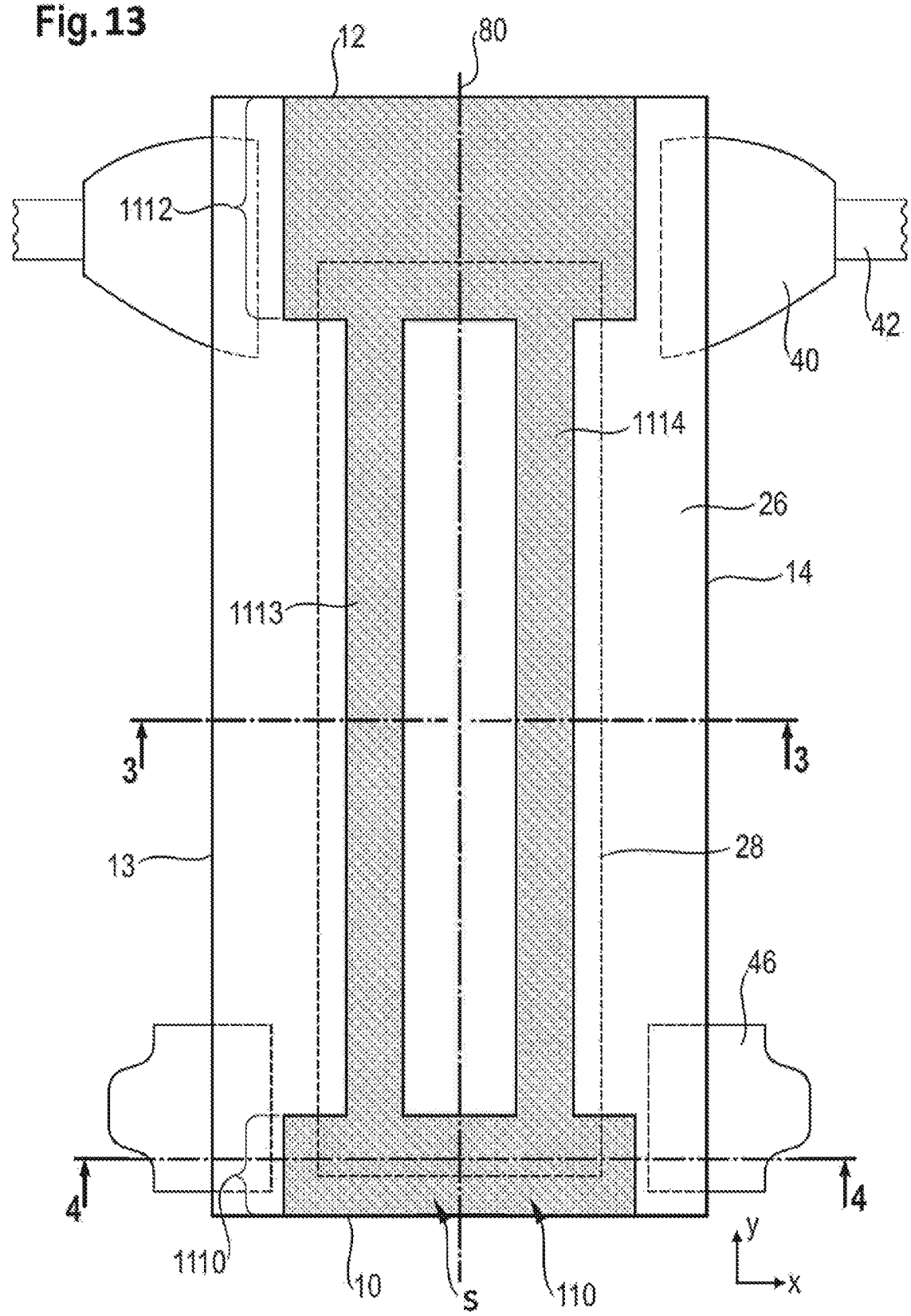
FIG. 13 shows a backsheet with a glue distribution according to the invention, with the outline of the absorbent core, the rest of the article being omitted for readability.

The first glue area may advantageously extend, at least portion-wise, across the full length of the core and furthermore along the full length of the backsheet. These longitudinally-extending portions are indicated by reference 1113, 1114 in the Figures. This provides for full length attachment of the core to the backsheet. When the first glue area extends longitudinally beyond the front and back edges of the core (10, 12), it can further provide for attachment of the topsheet to the backsheet in the areas beyond said front and back edges of the core. The first glue application area 110 may also comprise front and back portions 1110, 1112 which are relatively large in the transversal direction, in particular that overlap or cover the entire front edge 10 and back edge 12 of the core and backsheet to provide for a stronger attachment of the core in these areas 1110, 1112. These transversally extending sub-areas may provide that the absorbent core has no free corners which may be more easily subject to delamination. In summary, the first glue area as a whole may generally have a roman II numeral shape when seen from above, as shown in FIGS. 1*a*, 1*b* and 13, but other shapes are possible, see for example FIGS. 6 and 8.

As indicated previously, if channels are present in the absorbent core, the first channel and the second channel are at least partially not attached to the backsheet by the first or second glue, or otherwise. The channels may be advantageously not substantially attached by the first and second glue, or otherwise, to the backsheet. By "not substantially attached", it is meant that less than 25% of the surface of each channel is attached to the backsheet. For example, only the ends of the channels may be attached by the first glue as shown on FIGS. 1*a* and 1*b*.

Figure 12A:
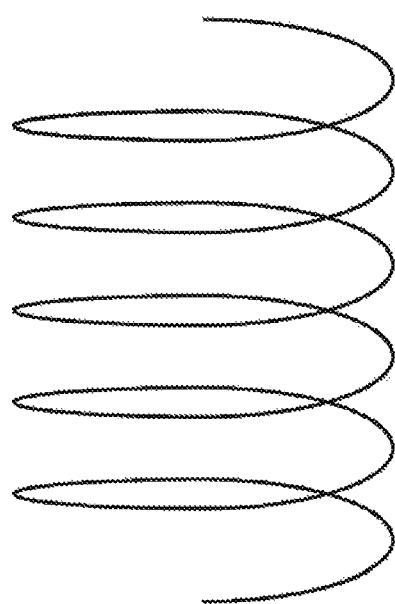
FIG. 12a,b,c illustrate three different discontinuous glue application pattern.
Figure 12B:
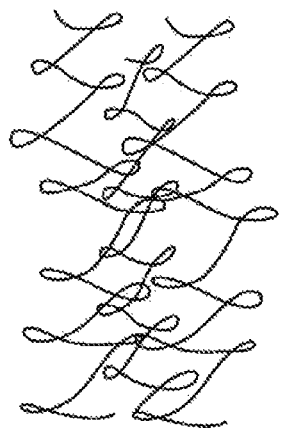
FIG. 12d illustrates a backsheet pleat or fold where a spot bonding of the film is formed.

Whereas the first and second glues may have the same or different compositions, the first glue application pattern is different from the second glue application pattern. The first glue application pattern may in particular be discontinuous. By discontinuous, it is meant that the second glue does not form a continuous layer on the application area (or each sub-areas if several sub-areas are present). The first glue application pattern may for example comprise filaments, fibers or the like creating a more or less regular web with relatively large areas between the glue filaments (or fibers) which are not covered by glue. Examples of these patterns are illustrated in FIG. 12*a-c* for example (spiral, mini swirls, and random pattern respectively).

The application pattern of the first glue will be typically determined by the application device used. A non-contact application method such as glue spraying is advantageous. Non-contact methods allow the coverage of relatively large areas for an economical use of glue material. The Nordson company published on Nonwovens report a good overview of usual non-contact glue applicators known in the art for gluing components of a diaper with an adhesive. The publication is available on the Nordson website at this web address: http://www.nordson.com/en-us/divisions/adhesive-dispensing/Literature/White_Paper/HoldingItTogetherBy-linefromNonwovensReport.pdf.

Figure 12C:
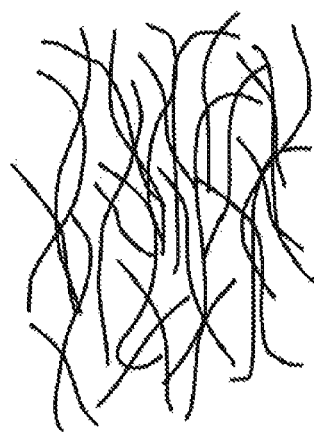

The first glue application pattern may in particular comprise a plurality of spray nozzles that spray large swirls (also called "spiral" glue pattern, and illustrated on FIG. 12*a*), mini swirls (illustrated in FIG. 12*b*) or random fibrous glue patterns (illustrated in FIG. 12*c*). The different application devices will be further illustrated below with reference to FIG. 11, which illustrates a process for applying the first and second glue between the backsheet and the core.

In general when the first glue is applied in a discontinuous pattern comprising glue filaments, such as swirls, miniswirls or randomly arranged fibers, it is preferred that each glue filament have a width of 0.05 to 0.3 mm wide or in particular 0.10 to 0.20 mm wide.

The basis weight of the first glue in said first glue application area may be between 0.5 and 9 gsm (grams per square meter), in particular 2 to 4 gsm.

The core-to-backsheet peel strength in the first glue application area can be comprised between 0.3 and 4 N/cm, or in particular 0.5 to 2N/cm.

Second Glue Application Area 100

The FIG. 1*b* represents a core-to-backsheet gluing distribution of an exemplary absorbent article having core channels and two different glues: a first glue on a first glue application area 110 (herein abbreviated as "first glue area") and a second glue, which is applied on a second glue application area 100 (herein abbreviated as "second glue area").

When channels are present the second glue area 100 can be at least partially present between the channels 26*a*, 26*b*. In the absence of channels is preferably applied along the longitudinal direction in the center of the absorbent core. Although there may be some overlap between the channels and the second glue area, it may be advantageous that the second glue area does not overlap with the channels. During use, the absorbent materials around the channels may swell as they absorb a fluid and the channels will become more tridimensional. If the second glue area overlaps the channels, there is a risk that the backsheet will follow the formation of these more pronounced three-dimensional channels. This may create stress in the backsheet and lead to rupture in the backsheet. Thus it may be advantageous that the width of the second glue area is smaller than or equal to the smallest distance separating the channels areas 26*a,b*. The second glue area 100 may be generally aligned with and may overlap the longitudinal axis 80 of the article, for example as a slot-coated glue stripe 100 as represented in the Figures.

The dimensions of the second glue area may generally vary and depend of the type of article considered, as well as the dimensions of the channels. The channels may generally extend more in the longitudinal direction than in the transversal direction. Thus the second glue area may also extend more in the longitudinal direction. For example, the second glue area may have a length which is at least 3 times, or at least 5 times longer than its width (as projected on the y and x axis respectively). The length of the second glue area 100 may for example range from 10% to 500% of the length L' of the channels 26*a,b*, for example from 5 cm to 30 cm for a diaper. The width of the second glue area may also vary, for example ranging from 0.5 mm to 10 mm for a diaper.

Although not illustrated in the Figures, it is also not excluded that the second glue area may comprise a plurality of macroscopic sub-areas separated from each other. This may be the case for example if the second glue is intermittently applied to provide a series of longitudinally aligned succeeding stripes, similar to intermittent road markings. It is also possible to print the second glue with sub-areas having diverse shapes including recreational shapes such as small characters or toys, in particular if the second glue comprises a pigment so that the second glue areas is visible through the backsheet on the garment-facing side of the article. More generally, one of the glues, in particular the second glue, may comprise a pigment or other colored substance so that it is visible through the backsheet. The second glue may also not comprise a pigment or another colored substance, so that the second glue is not particularly visible through the backsheet. The second glue may be also applied in a plurality (two or more) of parallel longitudinally extending stripes. In these other examples, the dimensions of the first area as indicated above apply to the sub-areas and the spaces between these sub-areas, taken as a whole.

The second glue has a second glue application pattern within the second glue application area 100. The application pattern is dependent of the method used to apply the second glue on the substrate. The second glue may be in particular applied continuously, meaning that the glue forms a two dimensional continuous layer within the glue application area. Typically the second glue may be applied by a contact method, where the applicator directly applies the glue on top of the substrate. Advantages of direct glue application and example are listed in the publication by the Nordson company mentioned above.

Because there is no distance or only a small distance between the nozzle and the substrate, contact deposition allows better control of the adhesive application. A typical contact applicator is a slot-coater. In slot coating, the adhesive exits the applicator through a thin, wide passageway—see FIG. 11*a*. Another well-known contact application technology is glue printing. These contact methods will be detailed in the process section below.

Using a contact method may typically provide the advantage of providing an accurate second glue application area 100. This may be advantageous because the distance between the channels may be relatively small, especially when the channels are curved at their closest positions relative to another. Since it may be advantageous to have no or a limited amount of glue in the areas of the channels, a contact method has the advantage of a more precise application than a non-contact method, such as adhesive spraying. A contact method also allows applying the glue continuously in the area of application. This may provide for a higher basis weight glue attachment per unit of surface, which may be an advantage as the second glue area may typically be smaller than the first glue area. The second glue area is generally limited on its side edges by the channels.

The second glue may be applied at a basis weight of between 5 to 100 gsm, in particular 10-50 gsm.

Alternative Designs (FIGS. 5-8)

Figure 5:
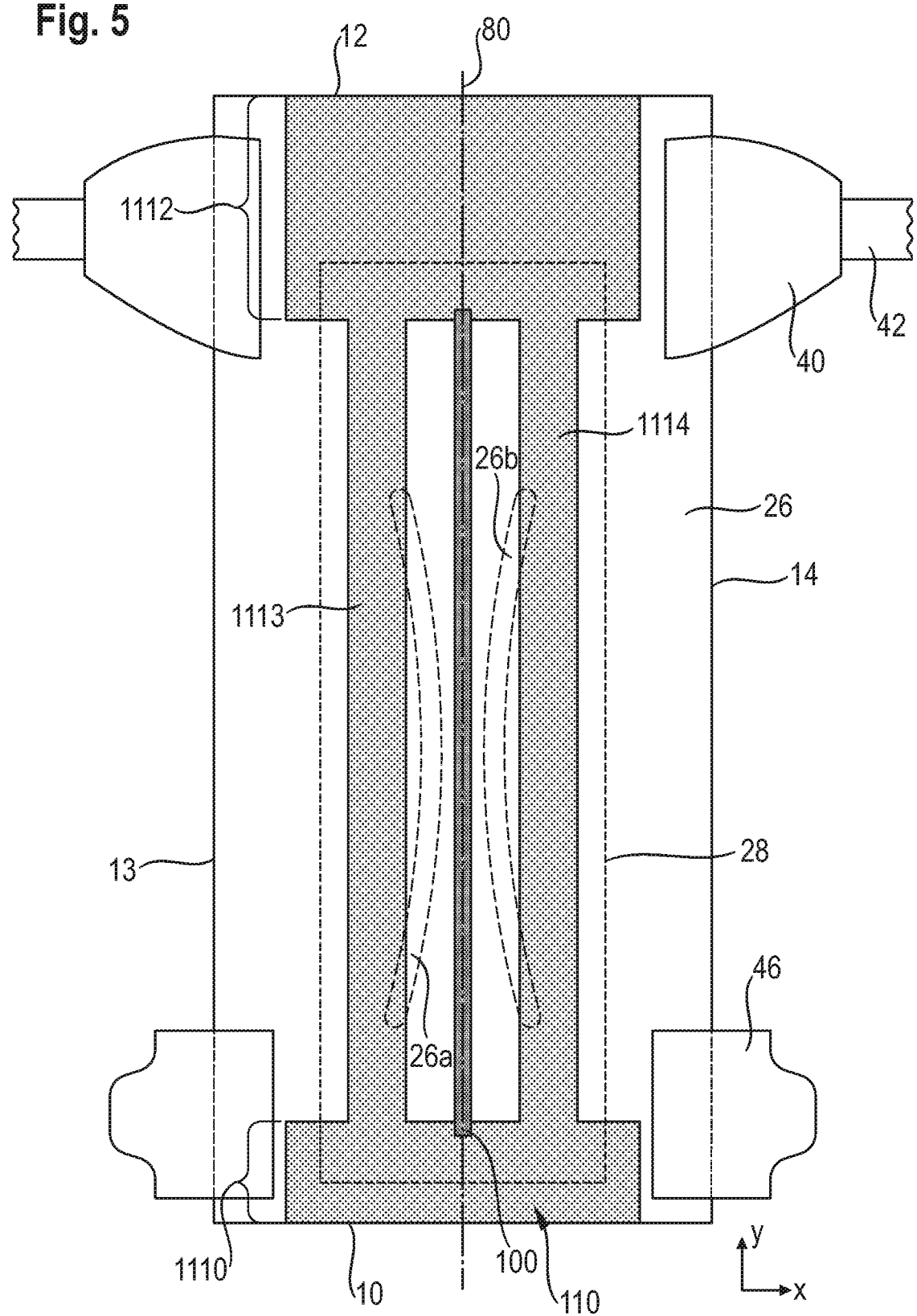
FIG. 5 shows an alternative core-to-backsheet glue distribution.
Figure 6:
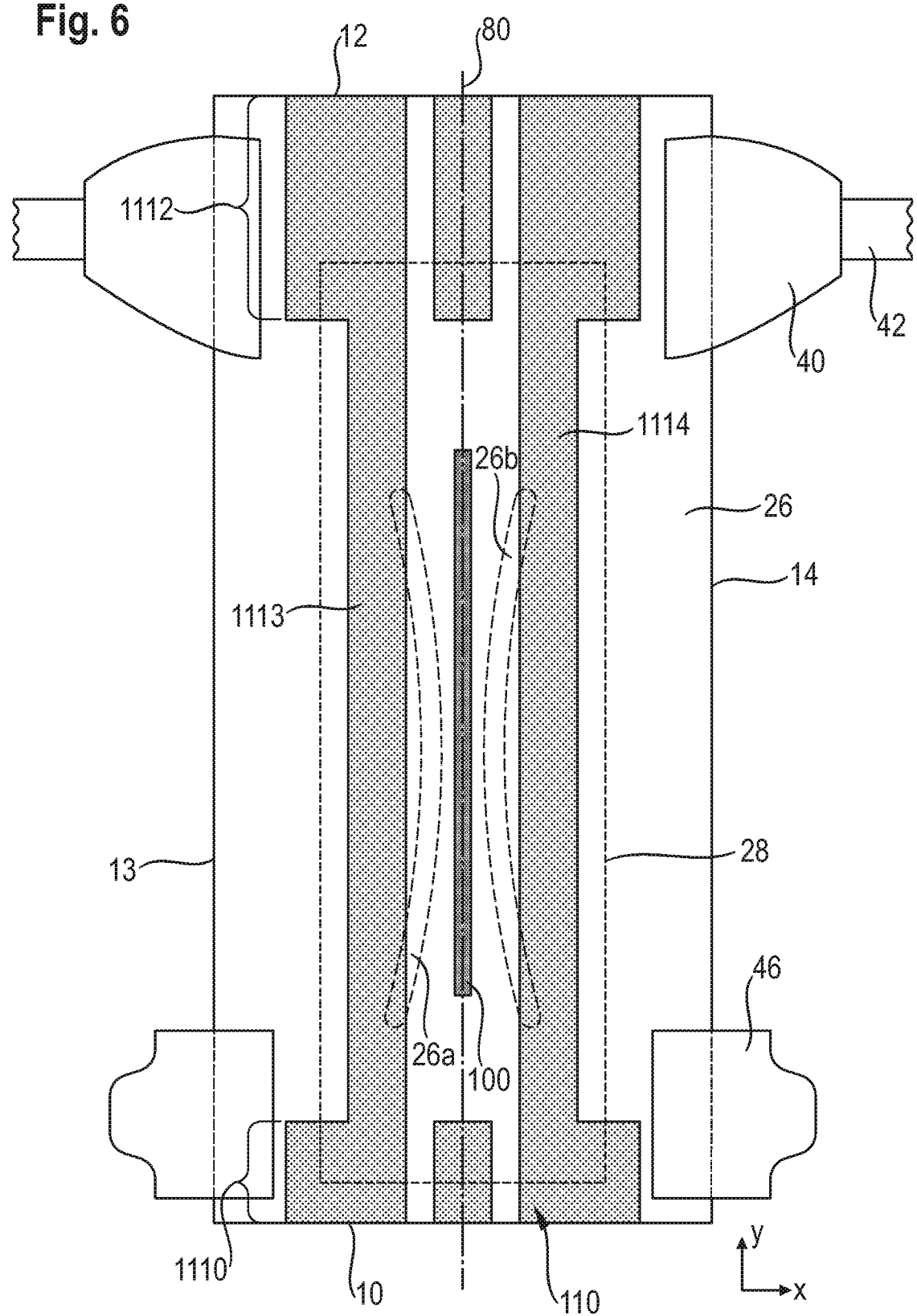
FIG. 6 shows another alternative core-to-backsheet glue distribution.

FIG. 1*b* discloses a core-to-backsheet gluing distribution having a second glue application area in the form of a stripe between the channels and a first glue application area generally resembling a roman II numeral outline. Alternative gluing areas distribution are of course possible, some of which are disclosed in FIGS. 5 to 8. FIG. 5 for example show an alternative glue distribution wherein the glue stripe of the second glue area is longer than in FIG. 1 and overlap towards its extremities with the first glue area. FIG. 6 shows another alternative design wherein the front and back portions 1110, 1112 of the first glue area are not unitary but comprise a separate central sub-area. This design allows reducing the amount of first glue used while still providing the benefits of gluing all four corners of the absorbent core to the backsheet.

Figure 7:
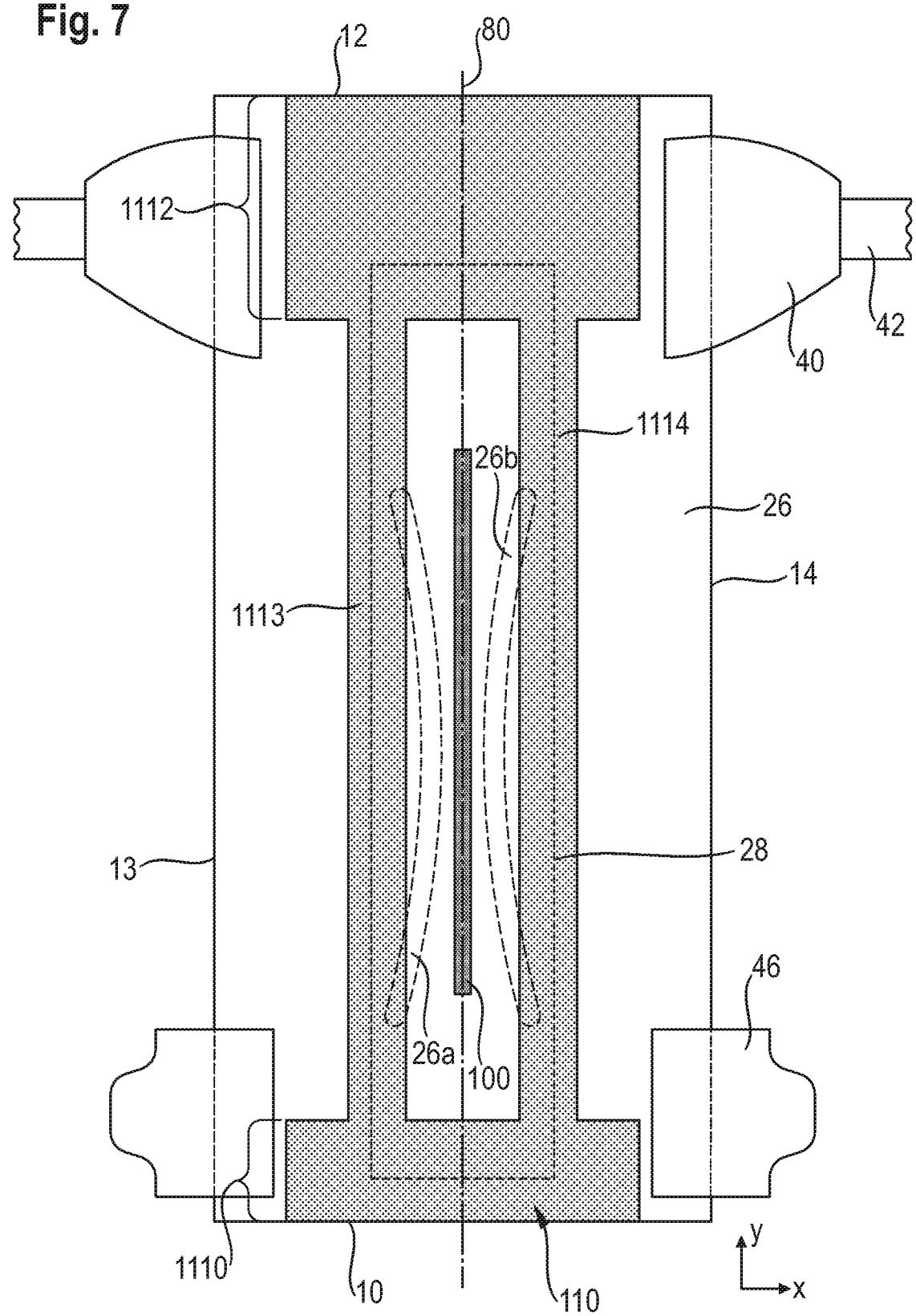
FIG. 7 shows another alternative core-to-backsheet glue distribution.

The longitudinally extending portions 1113, 1114 of the absorbent core may be typically present inwardly of the longitudinal side edges 284, 286 of the core as shown in FIGS. 1*a* and 1*b*, but it is not excluded that these portions 1113, 1114 overlap with the side edges 284,286 of the core, as illustrated in FIG. 7.

Figure 8:
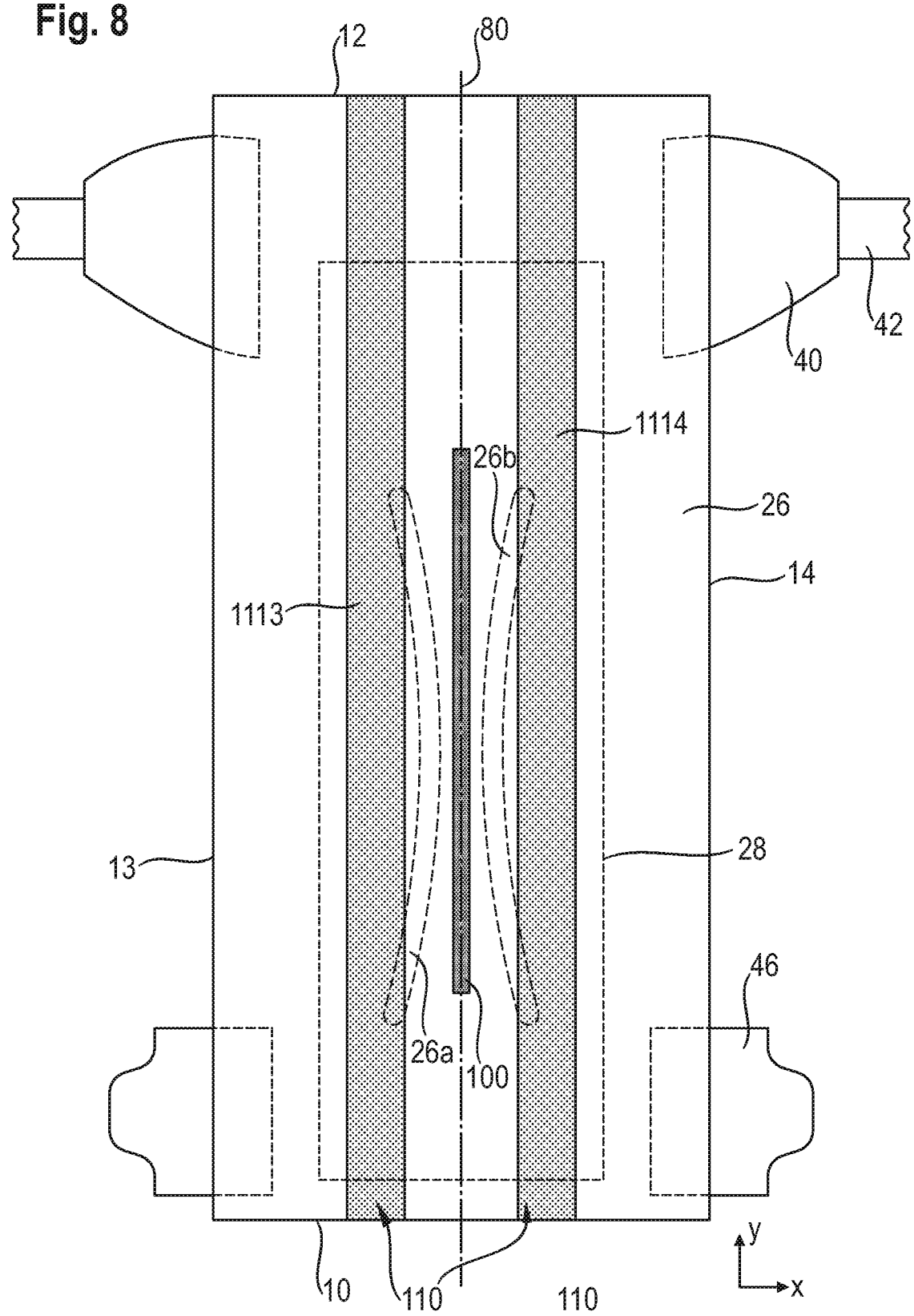
FIG. 8 shows another alternative core-to-backsheet glue distribution.

In a simplified design as illustrated on FIG. 8, the first glue area may be comprised of only two separate portions 1113, 1114 extending along the full length of the core and the backsheet. These portions may be placed inwardly of the side edges of the core (as shown in FIG. 8) or may be placed further outwardly transversally to also cover the side edges of the cores along their whole length, including the four corners of the core (not represented).

To note, in absorbent articles without core channels, the second glue might be absent and only the first glue might be present as shown in the example of FIG. 13. In addition, the first and second glue application areas may fully or partially overlap between the channel 26*a* and 26*b* or in absence of channels, although it is preferred that the application areas of the first and second glue do not overlap.

In general as explained above, the presence of a second glue is an advantageous feature but not a necessary one. So that absorbent articles with or without core channels and only featuring a "first glue" or, in other words, a single glue are within the scope of the invention.

An exemplary article featuring a single glue is depicted in FIGS. 1*a* and 13.

Process for Applying the First Glue and the Second Glue

The first glue and the second glue may be applied as schematically represented on FIG. 11, although other processes and variations thereof may of course be used. The process for making and assembling the rest of the absorbent article may be according any known processes in the art and will not be further detailed herein. The exemplary process of FIG. 11 shows the backsheet coming as a first continuous web feed 26 from the left side of the Figure and passing successively through two glue applicators. The second glue applicator 102 applies the second glue on the second glue application area 100. As indicated previously, this second glue applicator is advantageously a contact glue applicator, in particular for simplicity and cost a slot-coater 102 comprising a slot coating nozzle 104 (FIG. 11*a*) through which the slot glue is applied directly onto the backsheet. In slot coating, the adhesive exits the applicator through a thin, wide passageway—the nozzle laying the adhesive directly down on top of the substrate. The glue stripe can vary in width and pattern, depending on the application needs.

Other contact methods exist, for example as disclosed in US2011/0274834 (Brown). This document discloses a method and apparatus for the application of viscous fluids, such as adhesives, in pre-determined patterns to an advancing substrate. The fluid application apparatus may include a slot die applicator and a substrate carrier. The substrate carrier may include one or more pattern elements and may be adapted to advance the substrate past the slot die applicator as the slot die applicator discharges adhesive onto the substrate. In operation, the substrate is disposed on the substrate carrier; the substrate carrier advances the substrate past the slot opening of the slot die applicator. In turn, the substrate is intermittently compressed between the slot die applicator and the pattern surface of the pattern element. As the substrate is intermittently compressed, adhesive discharged from the slot die applicator is applied onto the substrate in an area having a shape substantially the same as a shape defined by the pattern surface. US2008/221543 (Wilkes) discloses another contact method for applying a colored hot-melt adhesive which may be used as a graphic. U.S. Pat. No. 6,033,513 (Nakamura) discloses an improved roll transfer coating method for hot melt adhesive as well as some roll transfer process of the prior art, all of which may also be used herein.

Directly after this second glue application, a first glue applicator 112 applies the first glue on the desired first glue application area 110 according to the first glue application pattern. The first glue applicator may be in particular a non-contact applicator. The first glue applicator 112 may comprise a plurality of nozzles 114b, 114c installed in parallel as represented on FIGS. 11b and 11c. In the example described, the second applicator 112 comprises 6 nozzles which can be independently controlled and turned on and off to form the desired first glue area such as the roman numeral II of FIGS. 1a, 1b, 5,7 and 13. In another example, the second applicator device may comprise 5 such nozzles, with the third nozzles separated by a gap from the two neighboring nozzles, to provide for a first glue application are as shown on FIG. 6. In another example, the second applicator 102 may for example comprise only two nozzles on each side of the longitudinal axis to provide a first glue application area as shown on FIG. 8.

Figure 12D:
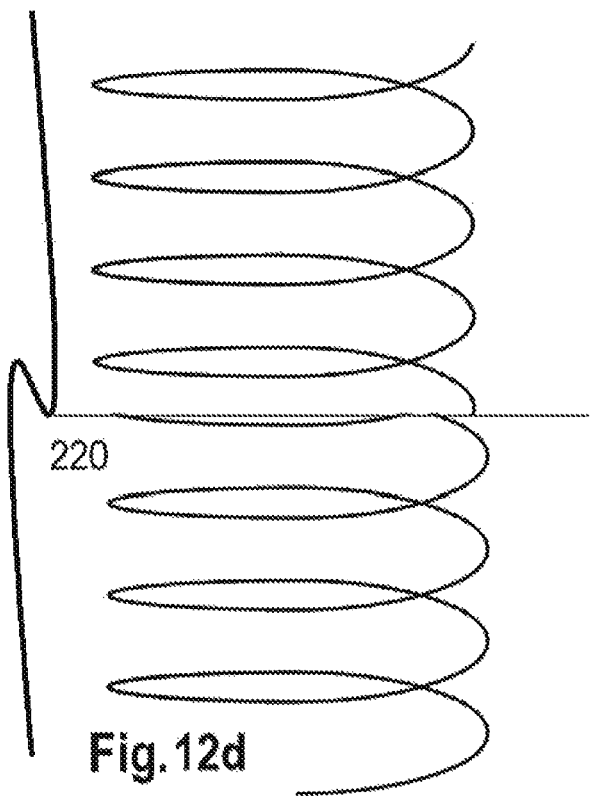

The individual spray nozzles of the first glue applicator may be of any type known in the art. In a first applicator example 112b, the nozzles may be for example as available from Nordson under the designation "CF applicator". These nozzles each deliver a single large swirl (also called spiral) from each nozzle 114b, as illustrated on FIG. 12a. The width of such large spiral may for example range from 10 mm to 30 mm. In the case of 6 such nozzles 114b installed in parallel, by intermittently turning on and off some of the nozzles (for example nozzles 1, 3, 4 and 6) and leaving two nozzles (2 and 5) continuously on, a roman II pattern can be repeatedly applied on an substrate such as the backsheet web feed. The same principle, placing in parallel a plurality of nozzles, can be used to apply the desired pattern for other applicators. The first glue may be in particular applied by an applicator 114c comprising several nozzle units 114c with a plurality of so-called mini-swirl nozzles, for example available from Nordson under the "Summit" designation. Each of these nozzle units 114c has a plurality, in particular three as represented for nozzle 114c, of sub-nozzles that together distribute several small swirls of adhesive (as illustrated on FIG. 12b). Each unit may apply a plurality of swirls having together the same width as indicated previously for one large swirl/spiral pattern. These nozzle units may also be independently turned on and off to provide the desired area of coverage and glue pattern. Mini-swirls can be used at a faster speed than large swirl/spiral and have a better edge definition of the boundary of the glue pattern, while not being as precise as slot application. Large and mini swirls may appear macroscopically as defining a boundary which is linear and longitudinally aligned, however, this pattern creates gaps between the tips of the loops where pleats or folds on the backsheet created during the deceleration on manufacturing can bond forming a "spot bond" 220 (see illustration of FIG. 12d). These spot bonds 220 can create tears or slit on the backsheet when the product is open and extended during application or usage. By increasing the number of loops per linear meter or overlapping the swirl or spiral glue pattern, it is possible to obtain better definition of the boundary edge of the glue pattern thus decreasing the concentration of stress on the most external areas of the loops and reducing spot bonds.

Of course any other known spraying nozzle type may be used, for example nozzle spraying a random pattern of glue, such as those supplied by Nordson under the "Signature" spray nozzle designation. These nozzles may produce random pattern of glue in fibrous form with relatively low peel forces for each individual glue fiber but high shear forces due to the plurality of bonding points. Although randomly sprayed, the adhesive filaments may appear as being generally longitudinally aligned (see illustration of FIG. 12c) due to the movement of the web at high speed, helping better distribute the stress along the boundary of the glue pattern and prevent spot bonding of the film between the gaps of the glue filament. An air flow may be used in conjunction with a spray nozzle to direct or disperse the glue filaments.

In addition, the first glue application area may advantageously extend forwards and backwards of the absorbent core to provide for extended areas of gluing of the backsheet with the topsheet for example. The front and back glue portions 1110, 1112 which may be relatively large to cover the front and back edges of the core may be separated by an intermediate area with a lesser amount of first glue coverage. The intermittently functioning nozzles (numbers 1, 3, 4 and 6 in this example) may be turned off for the intermediate area between the areas 1110, 1112. This allows material savings, as well as giving more freedom of movement of the core relative to the backsheet in this intermediate area. The intermittently functioning nozzles may be switched on and off only once for each individual core-to-backsheet gluing distribution. For example, the intermittent nozzles are switched on to form the larger back first glue portion 1112, and remain on to form the front larger first glue portion 1110 of the following gluing distribution, before being switched off for the intermediate middle region of this following gluing distribution.

It may be advantageous, as represented, to apply the second glue before the first glue, in particular when the second glue is applied with a contact applicator and first glue is applied with a non-contact applicator. Otherwise, there could be a risk of smearing the first glue on the contact applicator of the second glue. Similarly, it may be advantageous to apply the first and first glue onto the backsheet rather than the absorbent core, as the backsheet is a continuous web of material that will be typically easier to handle and can provide for a continuous application of the first glue over two succeeding core-to-backsheet gluing distributions.

After the glues have been applied, the feed of absorbent cores, as shown coming from the right, is then synchronized with the glue application patterns of the backsheet so that when the backsheet and absorbent core are brought in face-to-face contact with some pressure, they are attached by the first glue and, if present, by the second glue. The feed of absorbent cores may be supported on a continuous substrate which may be a component of the article. The supporting substrate for the absorbent cores may be in particular the remaining components of the article which have been pre-assembled on the line, with the topsheet 24 being the largest of these components on which the other have been assembled. The articles are then individualized for example by die cutting. Of course, other glues or attachment means, such as a chassis side slots on each of the longitudinal edges 13, 14 may be added to form the longitudinal seals between the backsheet and the topsheet and/or barrier leg cuffs of the final articles. These additional glues or other attachment means are not represented in the Figures for simplicity but may be as is known from any conventional absorbent articles.

Composition of the First Glue and the Second Glue

The first glue and second glue may be any type of glue known in the art and suitable to be applied according to the desired application pattern. The first glue and the second glue composition may be the same or different. In particular, any kind of thermoplastic hot-melt adhesives used in the field of absorbent article making may be suitable. Such an adhesive generally includes one or more polymers to provide cohesive strength (e.g., aliphatic polyolefins such as ethylene-propylene copolymers, polyetheramides, polyetheresters, and combinations thereof; ethylene vinyl acetate copolymers; styrene-butadiene or styrene-isoprene block copolymers; etc.), a resin or analogous material (sometimes called a tackifier) to provide adhesive strength (e.g., hydrocarbons distilled from petroleum distillates; rosins and/or rosin esters; terpenes derived, for example, from wood or citrus, etc.); and optional waxes, plasticizers or other materials to modify viscosity (e.g., mineral oil, polybutene, paraffin oils, ester oils, and the like), and/or other additives including, but not limited to, antioxidants or other stabilizers. Further information about hotmelt adhesive chemistry is discussed below for the fibrous thermoplastic adhesive layer that may be used in the absorbent core.

Exemplary suitable commercial adhesives for the first and/or second glue are available from Fuller under reference number 1286 or 1358, or from National Starch & Chemical under reference number DM 526, DM538 or DM3800.

The first glue can be applied e.g. using a swirl applicator delivering 50 to 300 loops per linear meter, in particular 80 to 150 loops per meter.

Loaded absorbent articles typically weight between of 100 and 210 g, but can be as heavy as 500 g or more. To support the weight of the absorbent core during wear, it is desired to have a core to backsheet laminate shear Strength in the range of 3 to 20N/cm, in particular 5 to 10N/cm.

General Description of the Absorbent Core 28

As used herein, the term "absorbent core" refers to a component of the absorbent article which comprises an absorbent material enclosed in a core wrap. As used herein, the term "absorbent core" does not include the topsheet, the backsheet and (if present) an acquisition-distribution layer or multilayer system, which is not integral part of the absorbent core, in particular which is not placed within the core wrap. The absorbent core is typically the component of an absorbent article that has the most absorbent capacity of all the components of the absorbent article and which comprises all, or at least the majority of, superabsorbent polymer (SAP). The core may consist essentially of, or consist of, the core wrap, the absorbent material and adhesives. The terms "absorbent core" and "core" are herein used interchangeably.

An exemplary core 28 that can be used in the invention is represented in FIGS. 9-10. The absorbent cores can typically be laid flat on a surface as shown on FIG. 9. The absorbent cores may also be typically thin and conformable, so that they can also be laid on a non-flat surface for example a drum during their making process or stored as a continuous roll of stock material before being converted into an absorbent article. For ease of discussion, the exemplarily absorbent core of FIG. 9 is represented in a flat state and extending in a transversal direction and a longitudinal direction. Unless otherwise indicated, dimensions and areas disclosed herein apply to the core in this flat-out configuration. The same applies to the absorbent article in which the core is integrated.

The absorbent core can typically be generally rectangular with a width W in the transversal direction and a length L in the longitudinal direction as measured from edge to edge, including the region of the core wrap which does not enclose the absorbent material, in particular at the front and back ends 280, 282, which may be sealed. In case the core is not rectangular, the maximum dimension measured along the transversal and longitudinal direction can be used to report the length and width of the core. The width and length of the core may vary depending on the intended usage. For baby and infant diapers, the width L may for example in the range from 40 mm to 200 mm and the length from 100 mm to 500 mm, as measured along the longitudinal axis 80' of the core. The longitudinal axis 80' of the core may be contiguous with the longitudinal axis 80 of the article. The article further comprises a liquid permeable topsheet 24 and a liquid impermeable backsheet 25 with the absorbent core 28 positioned between the topsheet and the backsheet.

The absorbent core comprises a front edge 280, a back edge 282 and two longitudinally extending side edges 284, 286 joining the front edge and the back edge. The front edge of the core is the edge of the core intended to be placed towards the front edge of the absorbent article. Typically the absorbent material 60 of the core may be advantageously distributed in somewhat higher amount towards the front edge than towards the back edge as more absorbency is typically required towards the front half of the article. Typically the front and back edges 280, 282 of the core may be shorter than the side edges 284, 286 of the core. The absorbent core may also comprise a top side 288 and a bottom side 290. The top side of the core is the side placed or intended to be placed towards the topsheet 24 of the article and the bottom side is the side placed or intended to be placed towards the backsheet 25 in the finished article. The top side of the core wrap is typically more hydrophilic than the bottom side.

The transversal axis of the core (herein also referred to as "crotch line"), is defined as the virtual line perpendicular to the longitudinal axis and passing through the crotch point C of the core. The crotch point C is defined as the point of the absorbent core placed at a distance of 0.45 of L from the front edge of the absorbent core, L being the length of the core as measured from the front edge 280 in direction of the back edge 282, as shown on FIG. 9.

The following will provide an exemplary description of possible core components. Further details are described for example in WO2012/170778 (Rosati et al.), WO2014/93311A1 (Arizti et al), WO2014/093310 (Ehrnsperger et al.), which disclose absorbent structures that comprise superabsorbent polymers, optionally a cellulosic material, and at least a pair of substantially longitudinally extending channels.

Core Wrap 16, 16'

The core wrap may comprise a first substrate 16 generally forming the top side of the core and a second substrate 16' generally forming the bottom side of the core wrap. The first and second substrates may be formed by two different materials, as shown in FIG. 10, but any other known core wrap constructions may also be used, for example wherein the core wrap is formed of a single material with one single longitudinal seal. The first and second substrates can be attached by gluing or otherwise to form at least one C-wrap seal 72 along each of the side edges 284, 286 of the core. The first and second substrates may be a nonwoven web, such as a laminate comprising spunbond ("S") or meltblown ("M") layer. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US 2011/0268932 A1, US 2011/0319848 A1 and US 2011/0250413 A1. The bottom substrate 16' may be inherently hydrophobic but air-permeable, and the top substrate 16 may be hydrophillically treated. There may be a seal along the front edge 282 and back edge 280 of the core wrap.

Combining the auxiliary glue layer with a C-wrap seal along at least one and preferably two longitudinal edges of the core, and optionally a further fibrous adhesive web (not represented), can provide an immobilization of the absorbent material in dry and wet state. The absorbent core may in general advantageously achieve an SAP loss of no more than about 70%, 60%, 50%, 40%, 30%, 20%, or 10% according to the Wet Immobilization Test described in US2010/0051166A1.

Absorbent Material 60

The absorbent material in the core can comprise a relatively high proportion of superabsorbent polymer (herein abbreviated as "SAP") enclosed within the core wrap. The SAP content may represent in particular at least 85%, 90%, 95% and up to 100%, of superabsorbent polymer by weight of the absorbent material. The absorbent material may in particular comprise no or only small amount of cellulose fibers, such as less than 20%, in particular less than 10%, 5% or even 0% of cellulose fibers by weight of the absorbent material. The absorbent material may thus advantageously consist or consist essentially of SAP. The SAP may be typically in particulate forms (superabsorbent polymer particles), but it not excluded that other form of SAP may be used such as a superabsorbent polymer foam for example. The absorbent core may thus be relatively thin, in particular thinner than conventional cores comprising cellulosic fibers. In particular, the caliper of the core (before use) as measured at the crotch point (C) or at any other points of the surface of the core according to the Core Caliper Test as described herein may be from 0.25 mm to 5.0 mm, in particular from 0.5 mm to 4.0 mm.

The term "superabsorbent polymer" refers herein to absorbent materials, which may be cross-linked polymer, and that can typically absorb at least 10 times their weight of an aqueous 0.9% saline solution as measured using the Centrifuge Retention Capacity (CRC) test (EDANA method WSP 241.2-05E). The SAP may in particular have a CRC value of more than 20 g/g, or more than 24 g/g, or of from 20 to 50 g/g, or from 20 to 40 g/g, or 24 to 30 g/g. The fluid permeability of a superabsorbent polymer can be quantified using its Urine Permeability Measurement (UPM) value, as measured in the test disclosed European patent application EP2,679,209. The UPM of the SAP may for example be of at least $10 \times 10^{-7}$ cm$^3$·sec/g, or at least $30 \times 10^{-7}$ cm$^3$·sec/g, or at least $50 \times 10^{-7}$ cm$^3$·sec/g, or more, e.g. at least 80 or $100 \times 10^{-7}$ cm$^3$·sec/g.

Absorbent Material Deposition Area 8

The absorbent material 60 defines an absorbent material deposition area 8, as seen from above within the plane of the core. The absorbent material deposition area 8 is defined by the periphery of the layer of absorbent material 60 within the core wrap, as seen from the top side of the absorbent core as shown on FIG. 9, and comprises the channel areas 26a,b encompassed within. The absorbent material deposition area 8 can be generally rectangular, for example as shown in FIG. 9, but other shapes can also be used such as a "T" or "Y" or "sand-hour" or "dog-bone" shape. In particular the deposition area may show a tapering along its width at the crotch region of the core. In this way, the absorbent material deposition area may have a relatively narrow width in an area of the core intended to be placed in the crotch region of the absorbent article. This may provide for example better wearing comfort.

Channels 26a,b

The absorbent cores can comprise one or more channels, typically at least two channels 26a,b (also referred to herein as "channel areas"). The term "channel" designates a longitudinally extending area of the core comprising less absorbent material than the surrounding areas so that an insulting fluid can be quickly distributed along the channel towards the front and back of the core. The channels may be in particular substantially free of absorbent material. By "substantially free" it is meant that in each of these areas the basis weight of the absorbent material is at least less than 25%, in particular less than 20%, less than 10%, of the average basis weight of the absorbent material in the rest of the absorbent material deposition area of the core. In particular there can be no absorbent material in these areas 26a,b. Minimal amount such as involuntary contaminations with absorbent material particles that may occur during the making process are not considered as absorbent material. The channels 26 are advantageously surrounded by the absorbent material, when considering the plane of the core, which means that the areas 26 do not extend to any of the edges of the deposition area 8 of the absorbent material 60.

The top layer 16 and the bottom layer 16' of the core wrap may be bonded to each other through these channel 26a,b. The bond 27 between the substrates in these area may be at least partially formed by an auxiliary glue 71 applied directly to the inner surface of at least one of the substrate, but other bonding methods are not excluded. This bonding allows the channels 26 to form more pronounced three-dimensional channels 26' as the absorbent material swells when it absorbs a liquid such as urine. Examples of channels according to the invention are described in details for example in WO2012/170778 (Rosati et al.), WO2014/93311A1 (Arizti et al), WO2014/093310 (Ehrnsperger et al.) which disclose absorbent structures that comprise superabsorbent polymers, optionally a cellulosic material, and at least a pair of substantially longitudinally extending channels.

When the absorbent material 60 swells upon absorbing a liquid, the core wrap bonds 27 remain at least initially attached in the channel areas 26. The absorbent material 60 swells in the rest of the core when it absorbs a liquid, so that the core wrap forms one or more pronounced channels along the core wrap bond 27. These channels are three dimensional and can serve to distribute an insulting fluid along their length to a wider area of the core. They may provide a quicker fluid acquisition speed and a better utilization of the absorbent capacity of the core.

The absorbent core 28 shown in figure comprise a first and second channels 26a,b disposed on each side of the longitudinal axis 80'. It is not excluded that the core may also comprise more than two channels. Shorter channel areas substantially free of absorbent material may also be present, for example in the back region or the front region of the core, as seen for example in the Figures of WO2012/170778.

The channels may extend substantially longitudinally, which means typically that each area extends at least as much in the longitudinal direction (y) than in the transversal direction (x), and typically at least twice as much in the longitudinal direction than in the transverse direction (as measured after projection on the respective axis). The channels 26 may have a length L' projected on the longitudinal axis 80 of the core that is at least 10% of the length L of the absorbent core, in particular from 20% to 80%. The channels may have an area substantially free of absorbent material having a width Wc along at least part of their length which is at least 2 mm, or at least 3 mm or at least 4 mm, up to for example 20 mm, or 16 mm or 12 mm. The width Wc may be constant through substantially the whole length or may vary along the length of the channels.

The channels 26 may be curved as shown in the Figures but they may be also straight and parallel to the longitudinal axis. It may be advantageous that there is no channels that coincide with the longitudinal axis 80' of the core. When present as a pair of channels 26a,b, these may be spaced apart from one another over their whole longitudinal dimension. The smallest spacing distance may be for example at least 5 mm, or at least 10 mm, or at least 16 mm.

Process for Making the Core

The absorbent material 60 may be deposited on any of the substrates 16, 16' using known techniques. In particular the SAP printing technology as disclosed for example in US2006/024433 (Blessing), US2008/0312617 and US2010/0051166A1 (both to Hundorf et al.), which allow relatively precise deposition of SAP at relatively high speed may be used. This technique uses a transfer device such as a printing roll to deposit SAP onto a substrate disposed on a grid of a support which may include a plurality of cross bars extending substantially parallel to and spaced from one another. Channel areas 26 substantially free of absorbent material can be formed for example by modifying the pattern of the grid and receiving drums so that no SAP is applied in the selected areas, as exemplary disclosed in US2012/0312491 (Jackels). This technology allows high-speed and precise deposition of SAP on a substrate in particular to provide one or more area(s) 26 substantially free of absorbent material surrounded by absorbent material. US2014/027066 (Jackels) further discloses specific raised strips and mating strips on the equipment for bonding the core substrates through the channel areas.

The absorbent material may be substantially continuously distributed in the deposition area 8. By "substantially continuous" it is meant that at least 50%, or at least to 70% and up to 100% of the deposition area comprises a continuous layer of absorbent material as seen from the top side of the core. The absorbent material may be for example applied as a single continuous layer on one of the substrate, the layer thus directly forming the material deposition area 8. A continuous layer of absorbent material, in particular of SAP, may also be obtained by combining two absorbent layers having matching discontinuous absorbent material application pattern wherein the resulting layer is substantially continuously distributed across the absorbent material deposition area, as exemplarily taught in US2008/0312622A1 (Hundorf).

Microfiber Glue

The absorbent core 28 may also comprise a fibrous thermoplastic adhesive material, to further immobilize the absorbent material 60 during the making process of the core and usage of the article. The fibrous thermoplastic adhesive material may be in particular useful to immobilize a dual layers of absorbent material to their respective substrate 16, 16'. Each of these absorbent layers may comprise land areas separated by junction areas and the fibrous thermoplastic adhesive material may then be at least partially in contact with the absorbent material in the land areas and at least partially in contact with the substrate layer 16, 16' in the junction areas. This imparts an essentially three-dimensional net-like structure to the fibrous layer of thermoplastic adhesive material, which in itself is essentially a two-dimensional structure of relatively small thickness, as compared to the dimension in length and width directions. Thereby, the fibrous thermoplastic adhesive material may provide cavities to cover the absorbent material in the land areas, and thereby immobilizes this absorbent material. The fibrous adhesive may be for example sprayed on an absorbent layer after it has been deposited on its substrate during the core making process.

The fibrous thermoplastic adhesive material may typically have a molecular weight (Mw) of more than 10,000 and a glass transition temperature (Tg) usually below room temperature or $-6°$ C.$<$Tg$<16°$ C. Typical concentrations of the polymer in a hotmelt are in the range of about 20% to about 40% by weight. The thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The tackifying resin may exemplarily have a Mw below 5,000 and a Tg usually above room temperature, typical concentrations of the resin in a hotmelt are in the range of about 30 to about 60%, and the plasticizer has a low Mw of typically less than 1,000 and a Tg below room temperature, with a typical concentration of about 0 to about 15%.

The thermoplastic adhesive used for the fibrous layer preferably has elastomeric properties, such that the web formed by the fibers on the SAP layer is able to be stretched as the SAP swell. Exemplary elastomeric, hotmelt adhesives include thermoplastic elastomers such as ethylene vinyl acetates, polyurethanes, polyolefin blends of a hard component (generally a crystalline polyolefin such as polypropylene or polyethylene) and a Soft component (such as ethylene-propylene rubber); copolyesters such as poly (ethylene terephthalate-co-ethylene azelate); and thermoplastic elastomeric block copolymers having thermoplastic end blocks and rubbery mid blocks designated as A-B-A block copolymers: mixtures of structurally different homopolymers or copolymers, e.g., a mixture of polyethylene or polystyrene with an A-B-A block copolymer; mixtures of a thermoplastic elastomer and a low molecular weight resin modifier, e.g., a mixture of a styrene-isoprenestyrene block copolymer with polystyrene; and the elastomeric, hot-melt, pressure-sensitive adhesives described herein. Elastomeric, hot-melt adhesives of these types are described in more detail in U.S. Pat. No. 4,731,066 (Korpman).

The thermoplastic adhesive material fibers may exemplarily have an average thickness of about 1 to about 50 micrometers or about 1 to about 35 micrometers and an average length of about 5 mm to about 50 mm or about 5 mm to about 30 mm. The auxiliary glue may improve the adhesion of the thermoplastic adhesive material to the substrate. The fibers adhere to each other to form a fibrous layer, which can also be described as a mesh. This is further detailed in the Rosati and Jackels references previously indicated.

General Description of the Absorbent Article 20

The absorbent article 20 comprises a liquid permeable topsheet 24, a liquid impermeable backsheet 25 and an absorbent core 28 according to the invention between the topsheet 24 and the backsheet 25. Some typical components of a baby taped diaper 20 are further represented in FIG. 2 in exploded view, and in cross-section view in FIGS. 3-4. Typically all components will be attached to the other neighboring components by glue, heat and pressure bonding, or otherwise, but only the core-to-backsheet gluing distribution is represented in these Figures for readability. The absorbent article may also comprise further typical components such as an acquisition layer 52 and/or a distribution layer 54, elasticized gasketing cuffs 32 within the chassis and partially upstanding barrier leg cuffs 34. The Figures also show other typical taped diaper components such as a fastening system comprising fastening tabs 42 attached towards the back edge 12 of the article and cooperating with a landing zone towards the front edge 10 of the article. The absorbent article may also comprise other typical components, which are not represented in the Figures, such as a back elastic waist feature, a front elastic waist feature, transverse barrier cuffs, a lotion application, a wetness indicator that reacts with urine such as a pH indicator which may be incorporated in the first or second glues, in particular the second glue, etc.

The topsheet 24, the backsheet 25, the absorbent core 28 and the other article components may be assembled in a variety of well-known configurations, in particular by gluing and/or heat embossing. Exemplary diaper assemblies are for example generally described in U.S. Pat. Nos. 3,860,003, 5,221,274, 5,554,145, 5,569,234, 5,580,411, and 6,004,306. The absorbent article is preferably thin. The article may be advantageously thin at the intersection of the longitudinal and transversal axes, for example with a caliper of from 1.0 mm to 8.0 mm, in particular from 1.5 mm to 6.0 mm, as measured using the Absorbent Article Caliper Test described below.

These and other components of the article will now be discussed in more detail.

Topsheet 24

The topsheet 24 forms at least a part of wearer-facing side of the absorbent article and is directly in contact with the wearer's skin. The topsheet 24 can be joined to the backsheet 25, the absorbent core 28 and/or any other layers as is known in the art (as used herein, the term "joined" encompasses configurations whereby an element is directly secured to another element by affixing the element directly to the other element, and configurations whereby an element is indirectly secured to another element by affixing the element to intermediate member(s) which in turn are affixed to the other element). Usually, the topsheet 24 and the backsheet 25 are joined directly to each other in some locations (e.g. on or close to the periphery of the article) and are indirectly joined together in other locations by directly joining them to one or more other elements of the article 20.

The topsheet 24 is preferably compliant, soft-feeling, and non-irritating to the wearer's skin. Further, at least a portion of the topsheet 24 is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. Typical diaper topsheets have a basis weight of from about 10 to about 28 gsm, in particular between from about 12 to about 18 gsm but other basis weights are possible.

Suitable formed film topsheets are also described in U.S. Pat. Nos. 3,929,135, 4,324,246, 4,342,314, 4,463,045, and 5,006,394. Other suitable topsheets may be made in accordance with U.S. Pat. Nos. 4,609,518 and 4,629,643. Such formed films are available from The Procter & Gamble Company of Cincinnati, Ohio as "DRI-WEAVE" and from Tredegar Corporation, based in Richmond, VA, as "CLIFF-T".

Any portion of the topsheet may be coated with a lotion as is known in the art. Examples of suitable lotions include those described in U.S. Pat. Nos. 5,607,760, 5,609,587, 5,643,588, 5,968,025 and 6,716,441. The topsheet 24 may also include or be treated with antibacterial agents, some examples of which are disclosed in WO 95/24173. Further, the topsheet, the backsheet or any portion of the topsheet or backsheet may be embossed and/or matte finished to provide a more cloth like appearance.

The topsheet 24 may comprise one or more apertures to ease penetration of exudates there-through, such as urine and/or feces (solid, semi-solid, or liquid). Examples of apertured topsheet are disclosed in U.S. Pat. No. 6,632,504. WO 2011/163582 also discloses suitable colored topsheet having a basis weight of from 12 to 18 gsm and comprising a plurality of bonded points. Each of the bonded points has a surface area of from 2 $mm^2$ to 5 $mm^2$ and the cumulated surface area of the plurality of bonded points is from 10 to 25% of the total surface area of the topsheet.

Backsheet 25

The backsheet 25 is generally that portion of the absorbent article 20 which forms the majority of the external surface of the article when worn by the user. The backsheet 25 is positioned towards the bottom side 290 of the absorbent core 28 and prevents the exudates absorbed and contained therein from soiling articles such as bed sheets and undergarments. The backsheet 25 is typically impermeable to liquids (e.g. urine). The backsheet 25 may for example be or comprise a thin plastic film, on the exterior surface of which a thin non-woven may be attached to improve the feel to the touch. Exemplary backsheet films include those manufactured by Tredegar Corporation, based in Richmond, VA, and sold under the trade name CPC2 film. Other suitable backsheet materials may include breathable materials which permit vapors to escape from the article 20 while still preventing exudates from passing through the backsheet 25. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, VA, and sold under the designation EXAIRE, and monolithic or Microporus films such as manufactured by Clopay Corporation, Cincinnati, OH under the name HYTREL blend P18-3097 or MicroPro. Some breathable composite materials are described in greater detail in WO 95/16746 (E. I. DuPont), U.S. Pat. No. 5,938,648 (LaVon et al.), U.S. Pat. No. 4,681,793 (Linman et al.), U.S. Pat. No. 5,865,823 (Curro), U.S. Pat. No. 5,571,096 (Dobrin et al.) and U.S. Pat. No. 6,946,585 (London Brown).

Typical films used for absorbent articles like diapers and pants are typically between 10 to 25 gsm and have longitudinal strength (also known as tensile strength) within 1 to 10N, specially between 2 and 6N. Preferred films for use in the backsheet of absorbent articles according to the invention have a basis weight between 10 and 20 gsm, because the improved glue pattern allows using thinner backsheet films which are preferred for reduced environmental impact, reduced cost and, and increased softness.

Acquisition and Distribution Layers 52, 54

The absorbent articles of the invention may comprise an acquisition layer 52, a distribution layer 54, both, or a single layer having both functions of acquiring and distributing the fluid. Typically, these layers do not comprise SAP as this may slow the acquisition and distribution of the fluid. The prior art discloses many type of acquisition-distribution system, see for example WO 2000/59430 (Daley), WO 95/10996 (Richards), U.S. Pat. No. 5,700,254 (McDowall), WO 02/067809 (Graef).

The function of an acquisition layer is to quickly acquire the fluid away from the topsheet so as to provide a good dryness for the wearer. The acquisition layer is typically placed directly under the topsheet. If present, the distribution layer may be at least partially disposed under the acquisition layer. The acquisition layer may typically be or comprise a non-woven material, for example a SMS or SMMS material, comprising a spunbonded, a melt-blown and a further spun-bonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (50/50 or 40/60 mix of 6 denier and 9 denier fibers). An exemplary binder is a butadiene/styrene latex. Nonwovens have the advantage that they can be manufactured outside the converting line and stored and used as a roll of material. Further useful nonwovens are described in U.S. Pat. No. 6,645,569 (Cramer et al.), U.S. Pat. No. 6,863,933 (Cramer et al.), U.S. Pat. No. 7,112,621 (Rohrbaugh et al.), US 2003/148684 (Cramer et al.) and US 2005/008839 (Cramer et al.).

The acquisition layer may be stabilized by a latex binder, for example a styrene-butadiene latex binder (SB latex). Processes for obtaining such latices are known, for example, from EP 149880 (Kwok) and US 2003/0105190 (Diehl et al.). In certain embodiments, the binder may be present in the acquisition layer 52 in excess of about 12%, about 14% or about 16% by weight. SB latex is available under the trade name GENFLO™ 3160 (OMNOVA Solutions Inc.; Akron, Ohio).

A distribution layer 54 may also be present. The function of a distribution layer is to spread the insulting fluid liquid over a larger surface within the article so that the absorbent capacity of the core can be more efficiently used. Typically the distribution layer is made of a nonwoven material based on synthetic or cellulosic fibers and having a relatively low density. The density of the distribution layer may vary depending on the compression of the article, but may typically range from 0.03 to 0.25 g/cm$^3$, in particular from 0.05 to 0.15 g/cm$^3$ measured at 0.30 psi (2.07 kPa). The distribution layer 54 may also be a material having a water retention value of from 25 to 60, preferably from 30 to 45, measured as indicated in the procedure disclosed in U.S. Pat. No. 5,137,537. The distribution layer 54 may typically have an average basis weight of from 30 to 400 g/m$^2$, in particular from 100 to 300 g/m$^2$. As shown in FIG. 2, the distribution layer may be rounded towards the back of the article. The distribution layer may be also profiled so that its basis weight towards the back of the article is lower than towards the front.

The distribution layer may for example comprise at least 50% by weight of crosslinked cellulose fibers. The crosslinked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf). The crosslinked cellulosic fibers provide higher resilience and therefore higher resistance against the compression in the product packaging or in use conditions, e.g. under baby weight.

Fastening System

The absorbent article may include a fastening system. The fastening system can be used to provide lateral tensions about the circumference of the absorbent article to hold the absorbent article on the wearer. This fastening system is not necessary for training pant article since the waist region of these articles is already bonded. The fastening system usually comprises a fastener 42 such as tape tabs, hook and loop fastening components, interlocking fasteners such as tabs & slots, buckles, buttons, snaps, and/or hermaphroditic fastening components, although any other known fastening means are generally acceptable. A landing zone is normally provided on the front waist region of the article for the fastener 42 to be releasably attached. Some exemplary surface fastening systems are disclosed in U.S. Pat. Nos. 3,848,594, 4,662,875, 4,846,815, 4,894,060, 4,946,527, 5,151,092 and 5,221,274 (Buell). An exemplary interlocking fastening system is disclosed in U.S. Pat. No. 6,432,098. The fastening system may also provide a means for holding the article in a disposal configuration as disclosed in U.S. Pat. No. 4,963,140 (Robertson et al.)

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499,978, 5,507,736, and 5,591,152.

Front and Back Ears 46, 40

The absorbent article may comprise front ears 46 and back ears 40 as is known in the art. The ears can be integral part of the chassis, for example formed from the topsheet and/or backsheet as side panel. Alternatively, as represented in FIG. 2, they may be separate elements attached by gluing and/or heat embossing. The back ears 40 are advantageously stretchable to facilitate the attachment of the tabs 42 on the landing zone 44 and maintain the taped diapers in place around the wearer's waist. The front ears 46 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Barrier Leg Cuffs 34 and Gasketing Cuffs 32

Absorbent articles such as diapers or training pants may typically further comprise components that improve the fit of the article around the legs of the wearer, in particular barrier leg cuffs 34 and gasketing cuffs 32. The barrier leg cuffs 32 may be formed by a piece of material, typically a nonwoven, which is partially bonded to the rest of the article and can be partially raised away and thus stand up from the plane defined by the topsheet, when the article is pulled flat as shown for example in FIG. 3. The barrier leg cuffs 34 can provide improved containment of liquids and other body exudates approximately at the junction of the torso and legs of the wearer. The barrier leg cuffs 34 extend at least partially between the front edge and the back edge of the absorbent article on opposite sides of the longitudinal axis and are at least present adjacent to the crotch point (C) of the core.

The barrier leg cuffs 34 may be delimited by a proximal edge 64 joined to the rest of the article, typically the topsheet and/or the backsheet, and a free terminal edge 66 intended to contact and forms a seal with the wearer's skin. The barrier leg cuffs 34 may be joined at the proximal edge 64 with the chassis of the article by a bond 65 which may be made for example by adhesive bonding, fusion bonding or combination of known bonding means. The bond 65 at the proximal edge 64 may be continuous or intermittent.

The barrier leg cuffs 34 can be integral with (i.e. formed from) the topsheet or the backsheet, or more typically be formed from a separate material joined to the rest of the article. Typically the material of the barrier leg cuffs may extend through the whole length of the article but is "tack bonded" to the topsheet towards the front edge and back edge of the article so that in these sections the barrier leg cuff material remains flush with the topsheet. Each barrier leg cuff 34 may comprise one, two or more elastic strings 35 close to this free terminal edge 66 to provide a better seal.

In addition to the barrier leg cuffs 34, the article may comprise gasketing cuffs 32, which are formed in the same plane as the chassis of absorbent article, in particular may be at least partially enclosed between the topsheet and the backsheet, and may be placed laterally outwardly relative to the barrier leg cuffs 34. The gasketing cuffs 32 can provide a better seal around the thighs of the wearer. Usually each gasketing leg cuff 32 will comprise one or more elastic string or elastic element 33 comprised in the chassis of the diaper for example between the topsheet and backsheet in the area of the leg openings.

U.S. Pat. No. 3,860,003 describes a disposable diaper which provides a contractible leg opening having a side flap and one or more elastic members to provide an elasticized leg cuff (a gasketing cuff). U.S. Pat. No. 4,808,178 (Aziz) and U.S. Pat. No. 4,909,803 (Aziz) describe disposable diapers having "stand-up" elasticized flaps (barrier leg cuffs) which improve the containment of the leg regions. U.S. Pat. No. 4,695,278 (Lawson) and U.S. Pat. No. 4,795,454 (Dragoo) describe disposable diapers having dual cuffs, including gasketing cuffs and barrier leg cuffs. All or a portion of the barrier leg and/or gasketing cuffs may be treated with a lotion.

Elastic Waist Feature

The absorbent article may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 28 and generally forms at least a portion of the back side of the absorbent article. Disposable diapers can be constructed so as to have two elastic waist features, one positioned in the front waist region and one positioned in the back waist region. The elastic waist feature may be constructed in a number of different configurations including those described in U.S. Pat. Nos. 4,515,595, 4,710,189, 5,151,092 and 5,221,274.

Relations Between the Layers and Components

Apart from the core-to-backsheet gluing distribution described in details previously, adjacent layers may be joined together using conventional bonding method such as adhesive coating via slot coating or spraying on the whole or part of the surface of the layer, or thermo-bonding, or pressure bonding or combinations thereof. Most of the bonding between components is for clarity and readability not represented in the Figure. Bonding between the layers of the article should be considered to be present unless specifically excluded. Adhesives may be typically used to improve the adhesion of the different layers, for example between the backsheet and the core wrap. The adhesives used may be any standard hotmelt glue as known in the art.

Method of Making

Apart from the method for applying the gluing distribution described in details previously, the absorbent article may be made otherwise by any conventional methods known in the art. In particular the articles may be hand-made or industrially produced at high speed on a modern converting line.

EXAMPLES

The following products according to the invention were prepared:

Inventive Example 1

Diapers having an absorbent material deposition area and two pair of channels similar to the one represented in FIG. 1a were prepared with the following specification:

One pair of channel extending from the front 25% of the longitudinal length of the absorbent core to the back 25% of the absorbent core. The channels were essentially absorbent material free and the top and bottom sides of the core wrap were attached together through these channels by the mean of the core glues described below. The width of the channels was about 8 mm and the projected length on the longitudinal axis of the article was about 230 mm. The channels were curved concave towards the longitudinal centerline of the article as shown in FIG. 1a, with a minimum separation of 20 mm and curved to reach out to 22 to 25 mm from the lateral edge of the core at front and back respectively.

Figure 3:
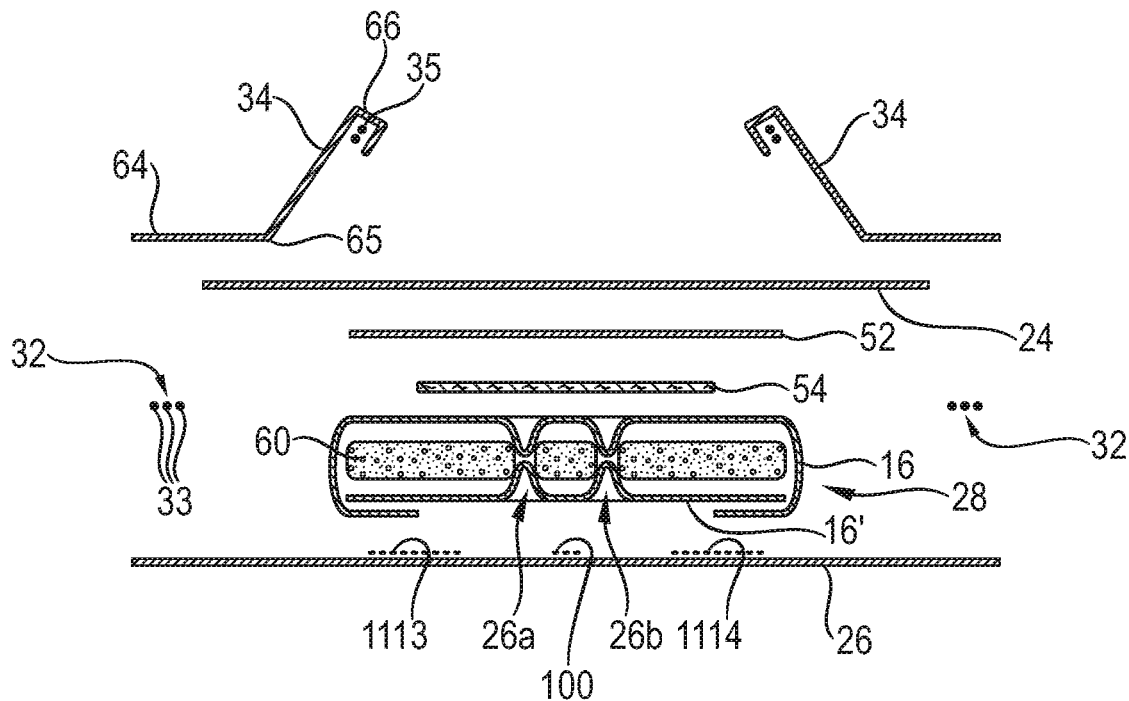
FIG. 3 shows a schematic cross-section of an absorbent article as in FIG. 2 in the center of the article.
Figure 4:
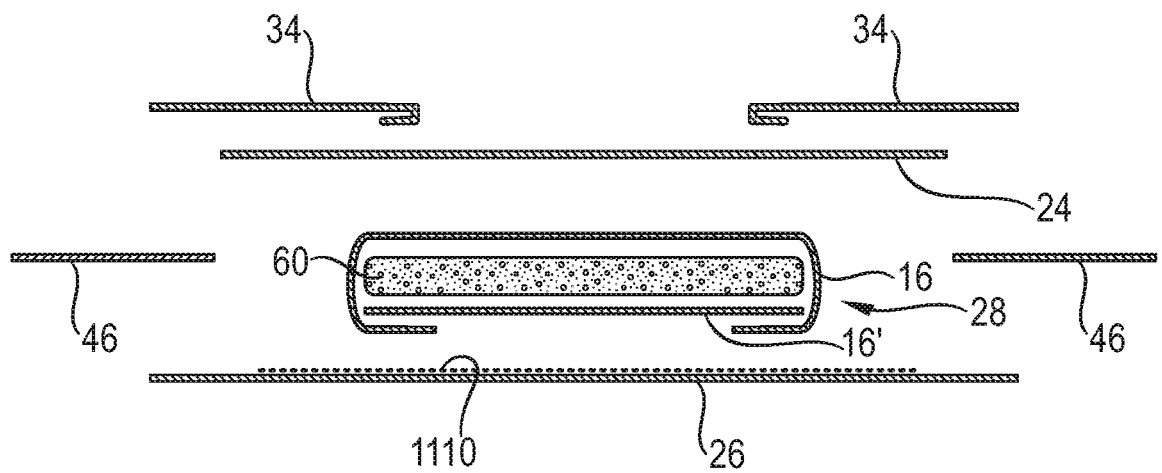
FIG. 4 shows a schematic cross-section of the absorbent article as in FIG. 2 towards the front edge of the article.

The absorbent core comprised in total 12.7 g of fast absorbing SAP (Nippon Shokubai NS CA 700) applied in an area of deposition having a length of 360 mm and a width of 110 mm. The SAP was distributed so that the basis weight of SAP was higher in the crotch region than at the front region and still lower towards the back region, in a ratio of about 0.25/0.40/0.3/0.1 of the total SAP along the longitudinal axis of the absorbent core (per quarter of the core length). SAP was distributed homogeneously in the transversal direction (no profiling in "cross-machine direction" or "CD"). The absorbent core was formed by SAP printing technology as disclosed in US2010/0051166A1, which combines two nonwoven substrates each supporting a SAP layer and microfiber elastic glue applied on each SAP layer which immobilizes the SAP layer on the substrate. These nonwoven substrates form the core wrap by C-wrapping the upper substrate onto the lower substrate as shown in FIG. 3. Auxiliary glue (from Henkel) was applied between the lower SAP layer and its respective lower substrate which was slot coated with 41 slots 1 mm wide with a distance of 1 mm between the slots along the whole length of the core wrap (390 mm), for a total Auxiliary glue application of 0.13 g. The microfiber glue (from H. B. Fuller) applied on each SAP layer was uniformly applied at width of 110 mm and length of 390 mm on each SAP layer, 0.17 g of microfiber glue was used on the core cover side and 0.13 g on the dusting layer side. The channels were formed by using a suitable printing drum delimiting the channels shape, further information on how to form channels can be found in EP application number EP12174117.7 using printed SAP technology.

The core wrap had a length of 390 mm with two end flaps free of absorbent material having a length of 15 mm at the back and at the front of the absorbent core. The front and back end seals of the core were slot glued together, the glue slots having a length of 30 mm from the front end seal and 20 mm from the back end seal using. The folded width of the core wrap was 120 mm. The core wrap comprised two nonwovens, the top substrate (16 in FIG. 3, referred further as "Core cover") was a 8 gsm SMMS nonwoven treated by a surfactant to be hydrophilic. The lower substrate (16' in FIG. 3, referred further as "Dusting layer") was a 10 gsm SMMS nonwoven. The core cover was cut at a length of 390 mm and a cut width of 165 mm. The dusting layer had a cut length of 390 mm and a cut width of 130 mm. The core cover was C-wrapped around the dusting layer on the lateral sides of the core and the lateral edges of the dusting layer slightly formed upwards on the edge of the absorbent material of the core so that the overall width of the folded core wrap was about 120 mm.

The core cover and dusting layer were bonded together through the channels. The bond was formed by the auxiliary and microfiber glue discussed hereinabove. The folded core cover around the dusting layer was bonded by the means of one slot per side, measuring 3 mm wide and 390 mm long. Henkel glue was used to bond the core cover to core dusting layer, applied at 4 mm from the lateral edge of the folded core cover at a total amount of 0.024 g.

The acquisition-distribution (52) system was formed by an acquisition layer of 43 gsm latex bonded nonwoven having a length of 318 mm and a width of 90 mm, and a distribution layer of cross-linked cellulose fibers (54) having a length of 298 mm and a width of 80 mm with a uniform basis weight of 195 gsm and centered on the acquisition layer area. The acquisition layer placed at 18 mm from the front of the absorbent core material and glued to the distribution layer using a Henkel hot melt adhesive on a printing glue pattern covering 15% of the area and having a length of 308 mm by 72 mm wide. The glue pattern was centered on the acquisition layer and had a total application area of 0.027 g.

The distribution layer was glued to nonwoven core cover using 7 slot coating glue applications, 3 mm wide each and separated by 8 mm. This pattern was 296 mm long and centered on the distribution layer using a total amount of 0.03 g of hot melt adhesive.

The topsheet (24) was 478 mm long formed by a 12 gsm carded nonwoven and the backsheet (26) was 478 mm long by 208 mm wide formed by laminating a Clopay 16 gsm film with a 15 gsm spunbond nonwoven. The topsheet was bonded to the acquisition layer by the means of 23 slot glue applications, 1 mm wide, separated 5 to 6 mm and 478 mm long for a total glue application of 0.098 g.

The backsheet film was glued to the backsheet nonwoven using 89 slots, 1 mm wide and about 1 mm apart from each other. The backsheet film to backsheet nonwoven glue application area covered the totality of the length of the backsheet (26) and was centered in transversal direction. The backsheet film used was a PP/PE breathable 16 gsm film, from Clopay, 478 mm long and 206 mm wide. The backsheet nonwoven was a 15 gsm Spundbond, 478 mm long by 212 mm wide.

The absorbent core was glued to the backsheet film using a first glue (110) from Henkel (DM3800) with the following areas of application.

1. A first center glue application area (1115), is formed by 8 summit spirals, 6 mm wide and equally spaced from each other to form an application area 50 mm wide by 45 mm long. The glue pattern was applied at the front edge of the product and centered in transversal direction. Two Nordson Summit applicators, 25 mm wide with 4 summits application per module were used to deliver this pattern. The front of the core was placed at 17 mm from the front edge of the absorbent article, and centered in transversal direction, overlapping the glue pattern by 28 mm in longitudinal direction. The same glue pattern was applied in the back of the absorbent article (second center glue application area 1116), covering an area 50 mm wide and 99 mm long (from the back edge of the absorbent article), and overlapping the core by 28 mm in longitudinal direction. The totality of the glue used for the first and second center glue application areas was 0.0177 g at the same glue basis weight in front and back of the product.
2. A first (1113) and a second (1114) lateral glue application areas, each formed by 4 summit spirals, 6 mm wide, equally spaced from each other, to form an application areas width of 25 mm; were applied at each of the lateral edge of the center glue application areas 1115 and 1116. These lateral glue application areas are 478 mm long by 25 mm wide each and bond the full longitudinal length of the core to the backsheet to provide the right support for the loaded core during wearing. A Nordson summit nozzle, 25 mm wide with 4 summit application per module was used to deliver these lateral application areas. The total amount of glue used on both lateral glue applications was 0.0588 g.
3. A first (1117), second (1118), third (1119) and fourth (1120) corner glue application areas are formed by 4 summit spirals, 6 mm wide, equally spaced from each other to form a pattern width of 25 mm and were applied at each lateral edge of the glues 1113 and 1114 so to cover the four corners of the core.

The combination of the center, lateral and corner glue application areas form the shape of a roman number "II" as shown in FIG. 1a.

The leg cuffs were commercial leg cuffs similar to those shown in FIG. 2, and comprised two 15 gsm, 478 mm long and 77 mm wide nonwovens on each side of the diaper. The leg cuffs were tackdown bonded to the topsheet with a 6 mm wide tool, for a distance of 100 mm from the front and 91 mm from the back of the edges of the diaper at a distance of 4 mm from the free edge. The nonwovens were fusion bonded along their length to the topsheet with a pair of continuous bond (65), 3 mm wide, along their bond line. Three, 1 mm wide with 2 mm spacing, slot glues were further applied along the continuous bond between the bonded leg cuff material and the topsheet, and the backsheet. The distance between the continuous bonds was 148 mm. The gasketing cuffs (the part of the cuffs not raised) were elasticized with three elastics in each side, attached to the diaper by adhesive glue (33 in the FIG. 3) on each side of the cuffs, starting at 85 mm from the front edge of the diaper and extending along a length of 281 mm. The raised barrier leg cuffs were elasticized with two elastics on each side (ref. 35 in the FIG. 3) each close to the terminal edge (ref 66 in the FIG. 3) of the barrier leg cuffs. The barrier cuff elastics were attached to the cuff material by the mean of glue, applied at 101 mm from the front of the absorbent article and a length of 302 mm. All elastics are formed by LYRCA® from DuPont and had a pre strain of 300%. The various components of the diapers were assembled in a conventional manner, typically by gluing or fusion bonding, unless indicated otherwise.

Inventive Example 2

The Inventive example 2 is made like Example 1 but using a different backsheet film: a 15 gsm PE/PP Breathable Backsheet film from Daedong.

Inventive Example 3

The Inventive Example 3 was made in the same way as example 2 but using National Starch (DM526) glue on the backsheet to core application maintaining the same pattern and glue amount, but increasing the backsheet to core bonding strength. The glue application and usage level remained unchanged.

COMPARATIVE EXAMPLE

The comparative example was made in the same way as example 1 with the following difference: National Starch (DM526) glue was used for the Backsheet to core applications. The absorbent core was bonded to the backsheet by the mean of 3 spiral summit glues per glue Nodson glue module versus 4 in the Inventive Examples. Each spiral summit was 7 mm wide equally spaced to form the total pattern (6 spirals on intermittent center application, 3 spirals per side on the lateral application, and 3 spirals per side on the most outer intermittent or corner glue application). In addition, the backsheet lamination glue pattern used was formed by 61 slots, 1 mm wide and about 2 mm spacing. The total amount of the backsheet film to backsheet nonwoven used was 0.072 g.

The total amount of glue per application on the backsheet to core glue was maintained the same across all Inventive Examples and the Comparative Example, while the glue design, usage and basis weights where adjusted to enable a reduction on Peel strength but not a large reduction on Shear force for the Inventive Examples versus the Comparative Example (see table below).

|  | Examples 1-2-3 | Comparative Example |
|---|---|---|
| Center glue applications (1115-1116) | | |
| # Summit spirals per application | 8 | 6 |
| Individual width of each spiral (mm) | 6 | 7 |
| Length at front (mm) | 45 | 45 |
| Length at back (mm) | 99 | 99 |
| Total length (mm) | 144 | 144 |
| Total glue applied (g) | 0.0177 | 0.0177 |
| Lateral glue applications (1113-1114) | | |
| # Summit spirals per application | 4 | 3 |
| Individual width of each spiral (mm) | 6 | 7 |
| Total length | 478 | 478 |
| Total glue applied | 0.0588 | 0.0588 |
| Corner glue applications (1117-1120) | | |
| # Summit spirals per application | 4 | 3 |
| Individual width of each spiral (mm) | 6 | 7 |
| Length at front | 45 | 45 |
| Length at back | 99 | 99 |
| Total length | 144 | 144 |
| Total glue applied | 0.0177 | 0.0177 |

Experimental Results

Measuring the comparative and Inventive examples described above, the following peel strengths, tear strengths were obtained (averaged on three replicates). The effectiveness of the reduction on the ratio peel strength/tear strength was proven to reduce backsheet failures or holes on standard manufacturing facilities.

|  | Comparative Example | Inventive Example 1 | Inventive Example 2 | Inventive Example 3 |
|---|---|---|---|---|
| Backsheet film material | Clopay 16 gsm | Clopay 16 gsm | Daedong 15 gsm | Daedong 15 gsm |
| Longitudinal Tear Strength of the Backsheet film (N/cm) | 3.38 | 3.38 | 4.77 | 4.77 |
| Core to backsheet peel strength (N/cm) | 1.70 | 0.88 | 0.90 | 1.29 |
| Peel/Tear strength | 50% | 26% | 19% | 27% |
| Observed diapers with holes over 3000 diapers | 13 (4333 ppm)* | 10 (3333 ppm) | 7 (2333 ppm) | 8 (2667 ppm) |

*Quality of the product reported in pad per million (number of observed defects/# total samples tested x 1.000.000)

Test Procedures

The values indicated herein are measured according to the methods indicated herein below, unless specified otherwise. All measurements are performed at 21° C.±2° C. and 50%±20% RH, unless specified otherwise. All samples should be kept at least 24 hours in these conditions to equilibrate before conducting the tests, unless indicated otherwise. All measurements should be reproduced on at least 4 samples and the average value obtained indicated, unless otherwise indicated.

Core to Backsheet Laminate Peel Strength

The "peel strength" method measures the peak amount of tensile force per unit of width required to pull a core to backsheet laminate apart during a 180° peel test using an tensile strength apparatus. The testing is conducted on samples of the laminate between the backsheet and the core in which the first glue (as defined above) is the only attachment means between core and backsheet. The laminate is prepared according to the definition provided in the present application respecting the intended orientation of the materials and of the glue applications within the absorbent article. The sample can be taken from an absorbent article following the instructions provided below.

The tensile tester must be calibrated according to the manufacturer's directions.

The sample to be tested must be a portion of core to backsheet laminate comprising a square area of 25.4 mm×20 mm which is part of the first glue application area. The sample must be oriented so that two edges of the square are oriented along the longitudinal direction of the backsheet film and of the application pattern.

In this area the first glue is applied according to the first glue application pattern. The "peel strength" measured by this method will depend on the core material, the backsheet film material, the type of glue and the pattern of application of the glue.

A sample of 25.4 mm wide by 200 mm long can be cut from the center front edge of a diaper as represented in the rectangle "S" in FIG. 1.

After the samples are cut, delaminate the backsheet from the core (starting from the un-bonded area if present) by hand for 50 mm in longitudinal direction, in order to create a portion of core and a portion of backsheet which can be securely clamped in the tensile instrument. In case the sample to be tested is smaller, the portions of material to be clamped can be created or made longer by attaching adhesive tape of appropriate size and strength to the core and backsheet in the sample so that the sample can be clamped in the tensile instrument and the adhesive tapes remain integral with core and backsheet respectively along the whole test. It must be ensured that the final sample when clamped at the start of the test has an area of at least 25.4×20 mm in transverse and longitudinal directions where the first glue (and only the first glue) connects core to backsheet. A freezing spray like IT Icer from Taerosol or the like or a solvent like dichloromethane can be used to facilitate manual delamination.

If a second glue or any other attachment means (other glues, mechanical bonding, fusion bonding etc.) are present in the 25.4×20 area to be measured the sample must be discarded.

Insert and clamp the backsheet material on the bottom jaw of the tensile equipment and the core on the upper jaw minimizing the slack on the sample and making sure the preload measured by the tensile instrument is not higher than 0.05N. Each jaw should have a suitable surface in contact with the sample to securely hold the backsheet and core without slipping as the laminate is pulled apart.

Test in a conditioned room maintained at 23° C.±2° C. and 50%±2% relative humidity. The jaws or clamps of the tensile tester are initially separated by 30 mm at the start of the test. Set the tensile tester to move the jaws apart at a speed of 305 mm/min. Start the test and record the maximum force (also called peak load) output starting when the jaw have moved a distance of 5 mm and continuing until the jaws has moved a distance of 200 mm apart from each other. The sample may be completely pulled apart at the end of the test.

The "peel strength" for each specimen is the maximum force measured for each sample during delamination reported to the nearest 0.01N and divided by the width of the first glue application on the sample, in cm (2.54 cm in the sample collected as directed). The final result is reported in N/cm to the nearest 0.01N/cm.

The results of the 3 samples are averaged; the average is reported in N/cm to the nearest 0.01N/cm.

Suitable tensile testers for use with this test, among others, include the Zwick Roell model BTC-FR2.5TH.D09 from Zwick GmbH & Co. KG. August-Nagel St 11, D89079 Ulm Germany, a Sintech tester, available from the Sintech Corporation, 1001 Sheldon Dr., Cary, N.C. 27513, an Instron tester available from the Instron Corporation, 2500 Washington St., Canton, Mass. 02021, or the alike.

Core to Backsheet Laminate Shear Strength

The "shear strength" method measures the peak amount of tensile force per unit of width required to pull a core to backsheet laminate apart in the plane of the laminate using a tensile strength apparatus. The testing is conducted on samples of the laminate between the backsheet and the core in which the first glue (as defined above) is the only attachment means between core and backsheet. The laminate is prepared according to the definition provided in the present application respecting the intended orientation of the materials and of the glue applications within the absorbent article. The sample can be taken from an absorbent article following the instructions provided below.

Calibrate the tensile tester according to the manufacturer's directions.

The sample to be tested must be a portion of core to backsheet laminate comprising a rectangular area of 25.4 mm in transversal direction×28 mm in longitudinal direction which is part of the first glue application area. The sample must be oriented so that two edges of the square are oriented along the longitudinal direction of the backsheet film and of the application pattern.

The sample needs to be provided with a portion of core and a portion of backsheet which can be clamped in the tensile instrument. To create these portions can be prepared like described for the peel strength measurement partially delaminating the sample or by using appropriate adhesive tape.

To note in this "shear strength" test the core and the backsheet will be clamped on opposite longitudinal ends of the sample so that the core to backsheet laminate is maintained in its plane (as opposed to the "peel strength" where the laminate is opened by pulling apart core and backsheet from the same longitudinal end of the sample.

A sample measuring 25.4 mm wide by at least 200 mm long can be cut from the center front edge of a diaper as represented in the rectangle "S" in FIG. 1a.

After the sample is cut, delaminate the backsheet from the core at both longitudinal edges to ensure that, after delamination, a 25.4 mm wide by a 28 mm long attached area is present where the first glue (and only the first glue) connects core to backsheet. If a second glue or any other attachment means (other glues, mechanical bonding, fusion bonding etc.) are present in the 20×20 area to be measured the sample must be discarded.

A freezing spray like IT Icer from Taerosol or the like or a solvent like dichloromethane can be used to facilitate manual delamination.

Insert and clamp the backsheet material from one longitudinal edge in the bottom jaw of the tensile equipment and the core (or rest of the diaper) from the opposite longitudinal edge in the upper jaw minimizing the slack on the sample but making sure the preload measured by the tensile instrument is not higher than 0.05N. Each jaw should have a suitable surface in contact with the sample to securely hold the backsheet and core without slipping as the laminate is pulled apart.

Test in a conditioned room maintained at 23° C.±2° C. and 50%±2% relative humidity. The jaws or clamps of the tensile tester are initially separated by 100 mm at the start of the test. Set the tensile tester to move the jaws apart at a speed of 305 mm/min. Start the test and record the maximum force (also called peak load) output starting when the jaw have moved a distance of 5 mm and continuing until the jaws has moved a distance of 200 mm apart from each other. The sample may be completely pulled apart, or the core or backsheet can completely be torn apart under strength at any time during the test. Even if this happens the measurement is considered valid.

The "shear strength" for each specimen is the maximum force measured for each sample during delamination reported to the nearest 0.01N and divided by the width of the first glue application on the sample, in cm (2.54 cm according to the instructions provided). The final result is reported in N/cm to the nearest 0.01N/cm.

The results of the 3 samples are averaged; the average is reported in N/cm to the nearest 0.01N/cm.

Suitable tensile testers for use with this test, among others, include the Zwick Roell model BTC-FR2.5TH.D09 from Zwick GmbH & Co. KG. August-Nagel St 11, D89079 Ulm Germany, a Sintech tester, available from the Sintech Corporation, 1001 Sheldon Dr., Cary, N.C. 27513, an Instron tester available from the Instron Corporation, 2500 Washington St., Canton, Mass. 02021, or the alike.

Backsheet Film "Longitudinal Tear Strength"

Cut a sample of backsheet film material of 25.4 mm across by 150 mm in the longitudinal direction of the winding direction of the raw material in the roll. Samples can be taken from an absorbent article at any point of the absorbent article which is free of a mechanical, fusion or similar bonding, elastics, stitches or other features which can alter the integrity and strength of the film. If the backsheet film sample is taken from the absorbent article, carefully delaminate the other components making sure the film is not damage. The orientation of the sample should be such that the longest dimension is along the longitudinal direction of the absorbent article. In case backsheet material is laminated to a nonwoven or to a core as typical in diapers, the nonwoven or core should be removed using dichloromethane or petroleum ether a solvent for the lamination glue or a Freezing spray as mentioned above.

Calibrate the tensile tester according to the manufacturer's directions.

Insert one end of the specimen into the upper jaw and close the jaw. Insert the other end into the lower jaw and close the jaw avoiding slack on the test sample but with the preload tension no larger than 0.05 N on the load cell.

Test in a conditioned room maintained at 23° C.±2° C. and 50%±2% relative humidity.

The jaws of the tensile tester are initially separated by 50.8 mm at the start of the test. Set the tensile tester to move the jaws apart at a speed of 508 mm/min, the break sensitivity at 50% (Break Sensitivity is the percent drop from peak where break is detected and the test stops).

Record the maximum peak load cell output starting when the jaws have moved a distance of 15 mm and continuing until the laws have moved a distance of 150 mm or the break sensitivity has been reached (sample tear). The sample may be completely pulled apart or torn apart at the end of the test.

Report the maximum peak load recorded for each sample and divide it by the width of the sample in cm. This number reported to the nearest 0.01 N/cm is the "longitudinal tear strength for that sample. The number is then averaged over 5 samples.

Suitable tensile testers for use with this test, among others, include the Zwick Roell model BTC-FR2.5TH.D09 from Zwick GmbH & Co. KG. August-Nagel St 11, D89079 Ulm Germany, a Sintech tester, available from the Sintech Corporation, 1001 Sheldon Dr., Cary, N.C. 27513, an Instron tester available from the Instron Corporation, 2500 Washington St., Canton, Mass. 02021, or the alike.

Centrifuge Retention Capacity (CRC)

The CRC measures the liquid absorbed by the superabsorbent polymer particles for free swelling in excess liquid. The CRC is measured according to EDANA method WSP 241.2-05.

Dry Absorbent Core Caliper Test

This test may be used to measure the caliper of the absorbent core (before use i.e. without fluid loading) in a standardized manner.

Equipment: Mitutoyo manual caliper gauge with a resolution of 0.01 mm, or equivalent instrument.

Contact Foot: Flat circular foot with a diameter of 17.0 mm (±0.2 mm). A circular weight may be applied to the foot (e.g., a weight with a slot to facilitate application around the instrument shaft) to achieve the target weight. The total weight of foot and added weight (including shaft) is selected to provide 2.07 kPa (0.30 psi) of pressure to the sample.

The caliper gauge is mounted with the lower surface of the contact foot in an horizontal plane so that the lower surface of the contact foot contacts the center of the flat horizontal upper surface of a base plate approximately 20×25 cm. The gauge is set to read zero with the contact foot resting on the base plate.

Ruler: Calibrated metal ruler graduated in mm.

Stopwatch: Accuracy 1 second.

Sample preparation: The core is conditioned at least 24 hours as indicated above.

Measurement procedure: The core is laid flat with the bottom side, i.e. the side intended to be placed towards the backsheet in the finished article facing down. The point of measurement (e.g. the crotch point C) is carefully drawn on the top side of the core taking care not to compress or deform the core.

The contact foot of the caliper gauge is raised and the core is placed flat on the base plate of the caliper gauge with the top side of the core up so that when lowered, the center of the foot is on the marked measuring point.

The foot is gently lowered onto the article and released (ensure calibration to "0" prior to the start of the measurement). The caliper value is read to the nearest 0.01 mm, 10 seconds after the foot is released.

The procedure is repeated for each measuring point. If there is a fold at the measuring point, the measurement is done in the closest area to this point but without any folds. Ten articles are measured in this manner for a given product and the average caliper is calculated and reported with an accuracy of one tenth mm.

Absorbent Article Caliper Test

The Absorbent Article Caliper Test can be performed as for the Dry Absorbent Core Caliper Test with the difference that the caliper of the finished absorbent article is measured instead of the caliper of the core. The point of measurement may correspond vertically with the crotch point of the core as defined earlier. If the absorbent articles were provided folded and/or in a package, the articles to be measured are unfolded and/or removed from the center area of the package. If the package contains more than 4 articles, the outer most two articles on each side of the package are not used in the testing. If the package contains more than 4 but fewer than 14 articles, then more than one package of articles is required to complete the testing. If the package contains 14 or more articles, then only one package of articles is required to perform the testing. If the package contains 4 or fewer articles then all articles in the package are measured and multiple packages are required to perform the measurement. Caliper readings should be taken 24±1 hours after the article is removed from the package, unfolded and conditioned. Physical manipulation of product should be minimal and restricted only to necessary sample preparation.

Any elastic components of the article that prevent the article from being laid flat under the caliper foot are cut or removed. These may include leg cuffs or waistbands. Pant-type articles are opened or cut along the side seams as necessary. Apply sufficient tension to flatten out any folds/wrinkles. Care is taken to avoid touching and/or compressing the area of measurement.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for personal hygiene having a wearer-facing side, a garment-facing side and a longitudinal axis and transversal axis, the article comprising:
    a topsheet on the wearer-facing side;
    a backsheet on the garment-facing side;
    an absorbent core between the topsheet and the backsheet, the absorbent core having a top side and a bottom side, the absorbent core comprising an absorbent material comprising a superabsorbent polymer;
    the backsheet comprising a plastic film, the plastic film having a longitudinal tear strength measured in N/cm;
    the absorbent core being partially attached to the plastic film of the backsheet in at least two glue application areas, the at least two glue applications areas comprising a first glue application area; and
    wherein at least a continuous area of about 10 mm in longitudinal direction and about 25 mm in transversal direction of the bottom side of the core is unattached to the backsheet;
    wherein in the first glue application area, the absorbent article comprises a core-to-backsheet peel strength measured in N/cm, and
    wherein the core-to-backsheet peel strength ranges from about 10% to about 40% of the longitudinal tear strength of the plastic film.

2. The absorbent article of claim 1, wherein the continuous area overlaps a lateral edge of the absorbent core.

3. The absorbent article of claim 2, wherein the continuous area overlaps both lateral edges of the absorbent core.

4. The absorbent article of claim 1, wherein the first glue application area comprises a pattern having glue filaments, swirls, miniswirls, and/or glue fibers.

5. The absorbent article of claim 1, wherein the core-to-backsheet peel strength in the first glue application area is from about 0.3 N/cm to about 4 N/cm.

6. The absorbent article of claim 1, wherein the continuous area is disposed between two of the at least two glue application areas.

7. The absorbent article of claim 1, wherein the absorbent core comprises a first channel disposed on one side of the longitudinal axis and a second channel disposed on the other side of the longitudinal axis.

8. The absorbent article of claim 7, wherein the first channel and second channel are at least partially unattached to the backsheet.

9. The absorbent article of claim 7, wherein a second glue application area is at least partially present between the channels.

10. The absorbent article of claim 1, wherein the core-to-backsheet peel strength is from about 3N/cm to about 20N/cm.

11. The absorbent article of claim 1, wherein the absorbent material of the absorbent core comprises less than about 20% of cellulosic fibers, by weight of the absorbent material.

12. The absorbent article of claim 1, wherein the continuous area overlaps a longitudinal edge of the absorbent core.

13. The absorbent article of claim 12, wherein the first glue application area comprises at least a first portion on one side of longitudinal axis and at least a second portion on the other side of the longitudinal axis, and both portions extends along the full length of the absorbent core.

* * * * *